(12) United States Patent
Simi et al.

(10) Patent No.: US 10,864,051 B2
(45) Date of Patent: Dec. 15, 2020

(54) ROBOTIC SURGICAL ASSEMBLY

(71) Applicant: MEDICAL MICROINSTRUMENTS S.P.A., Calci, Pisa (IT)

(72) Inventors: Massimiliano Simi, Pisa (IT); Giuseppe Maria Prisco, Pisa (IT)

(73) Assignee: MEDICAL MICROINSTRUMENTS S.P.A., Pisa (IT)

( * ) Notice: Subject to any disclaimer, the term of this patent is extended or adjusted under 35 U.S.C. 154(b) by 256 days.

(21) Appl. No.: 15/768,519

(22) PCT Filed: Oct. 14, 2016

(86) PCT No.: PCT/EP2016/074805
§ 371 (c)(1),
(2) Date: Apr. 13, 2018

(87) PCT Pub. No.: WO2017/064301
PCT Pub. Date: Apr. 20, 2017

(65) Prior Publication Data
US 2018/0303567 A1  Oct. 25, 2018

(30) Foreign Application Priority Data
Oct. 16, 2015 (IT) ........................ 102015000062500

(51) Int. Cl.
*A61B 34/37* (2016.01)
*B25J 9/16* (2006.01)
(Continued)

(52) U.S. Cl.
CPC ............ *A61B 34/37* (2016.02); *A61B 1/3132* (2013.01); *A61B 10/04* (2013.01);
(Continued)

(58) Field of Classification Search
CPC ......... A61B 34/30; A61B 30/00; A61B 34/37; A61B 90/20; A61B 1/3132; A61B 10/04;
(Continued)

(56) References Cited

U.S. PATENT DOCUMENTS 5,279,309 A   1/1994  Taylor et al.
5,876,325 A   3/1999  Mizuno et al.
(Continued)

FOREIGN PATENT DOCUMENTS

WO   2010/009221 A2   1/2010

OTHER PUBLICATIONS

International Search Report and Written Opinion of the International Searching Authority for International Patent Application No. PCT/EP2016/074805 dated Jan. 16, 2017, 16 pages.

*Primary Examiner* — George J Ulsh
(74) *Attorney, Agent, or Firm* — Merchant & Gould P.C.

(57) ABSTRACT

A robotic surgical assembly (100) includes a support (104), one macro-positioning arm (30), connected to the support (104) and having a plurality of degrees of freedom. The macro-positioning arm (30) includes a support member (38), at least two micro-positioning devices (41, 141, 241, 341), each having a plurality of motorized degrees of freedom, connected in cascade to the support member (38) of the macro-positioning arm (30), and at least two medical instruments (60, 160, 260, 360). Each instrument is connected in cascade to each of the micro-positioning device and includes a jointed device (70, 170, 270) having a plurality of motorized degrees of freedom including a plurality of rotational joints. Each of the at least two medical instruments (60, 160, 260, 360) has a shaft (65), suitable for distancing the jointed device from the micro-positioning devices by a predetermined distance in a shaft direction (X-X).

25 Claims, 24 Drawing Sheets

Figure 1B:
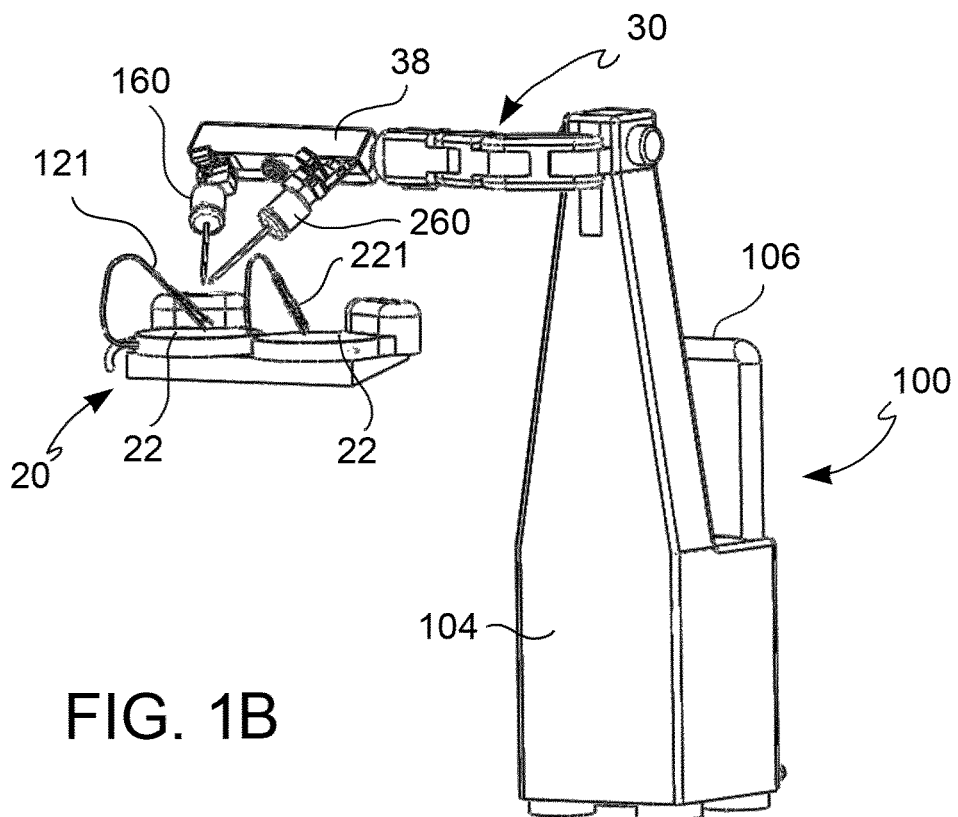

(51) Int. Cl.
  *A61B 34/00*   (2016.01)
  *A61B 90/20*   (2016.01)
  *B25J 3/04*   (2006.01)
  *B25J 9/10*   (2006.01)
  *B25J 15/00*   (2006.01)
  *A61B 17/062*   (2006.01)
  *A61B 90/00*   (2016.01)
  *A61B 34/30*   (2016.01)
  *A61B 34/35*   (2016.01)
  *A61B 1/313*   (2006.01)
  *A61B 10/04*   (2006.01)
  *A61B 17/00*   (2006.01)
  *G05B 19/402*   (2006.01)
  *A61B 90/25*   (2016.01)
  *A61B 34/20*   (2016.01)
  *A61B 17/29*   (2006.01)
  *A61B 17/32*   (2006.01)
  *A61B 17/3211*   (2006.01)
  *A61B 17/34*   (2006.01)

(52) U.S. Cl.
  CPC ...... *A61B 17/00234* (2013.01); *A61B 17/062* (2013.01); *A61B 34/30* (2016.02); *A61B 34/35* (2016.02); *A61B 34/71* (2016.02); *A61B 34/72* (2016.02); *A61B 90/20* (2016.02); *A61B 90/25* (2016.02); *A61B 90/361* (2016.02); *B25J 3/04* (2013.01); *B25J 9/1015* (2013.01); *B25J 9/1669* (2013.01); *B25J 15/0052* (2013.01); *G05B 19/402* (2013.01); *A61B 17/29* (2013.01); *A61B 17/3211* (2013.01); *A61B 17/320016* (2013.01); *A61B 17/34* (2013.01); *A61B 2017/00345* (2013.01); *A61B 2034/2048* (2016.02); *A61B 2034/2051* (2016.02); *A61B 2034/301* (2016.02); *A61B 2034/715* (2016.02); *A61B 2090/061* (2016.02); *A61B 2090/064* (2016.02); *G05B 2219/45117* (2013.01)

(58) Field of Classification Search
  CPC . A61B 17/00234; A61B 17/062; A61B 17/29; A61B 17/320016; A61B 17/3211; A61B 17/34; A61B 34/71; A61B 34/72; A61B 34/75; A61B 90/25; A61B 90/361; A61B 2017/00345; A61B 2034/301; A61B 2034/2048; A61B 2034/2051; A61B 2034/715; A61B 2090/061; A61B 2090/064; B25J 9/00; B25J 9/16; B25J 3/04; B25J 9/1015; B25J 9/1669; B25J 15/0052; G05B 19/402; G05B 2219/45117
  See application file for complete search history.

(56) References Cited

U.S. PATENT DOCUMENTS

| | | |
|---|---|---|
| 6,385,509 B2 | 5/2002 | Das et al. |
| 6,468,265 B1 | 10/2002 | Evans et al. |
| 6,731,988 B1 | 5/2004 | Green |
| 6,963,792 B1 | 11/2005 | Green |
| 7,155,316 B2 | 12/2006 | Sutherland et al. |
| 8,521,331 B2 | 8/2013 | Itkowitz |
| 2006/0087746 A1 | 4/2006 | Lipow |
| 2009/0171373 A1 | 7/2009 | Farritor et al. |
| 2014/0135794 A1 | 5/2014 | Cau |
| 2014/0179997 A1 | 6/2014 | Von Grunberg et al. |

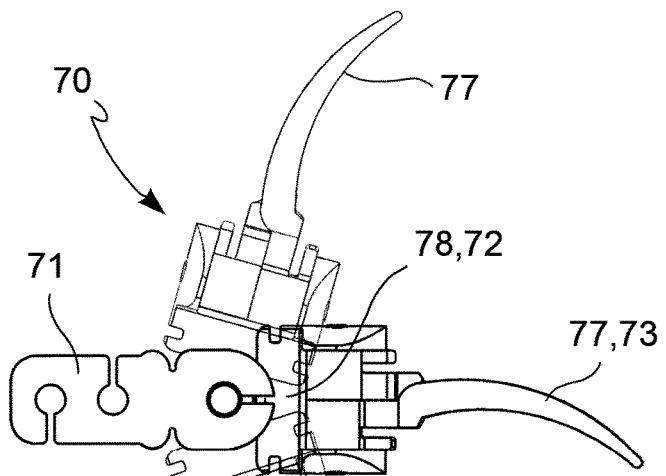
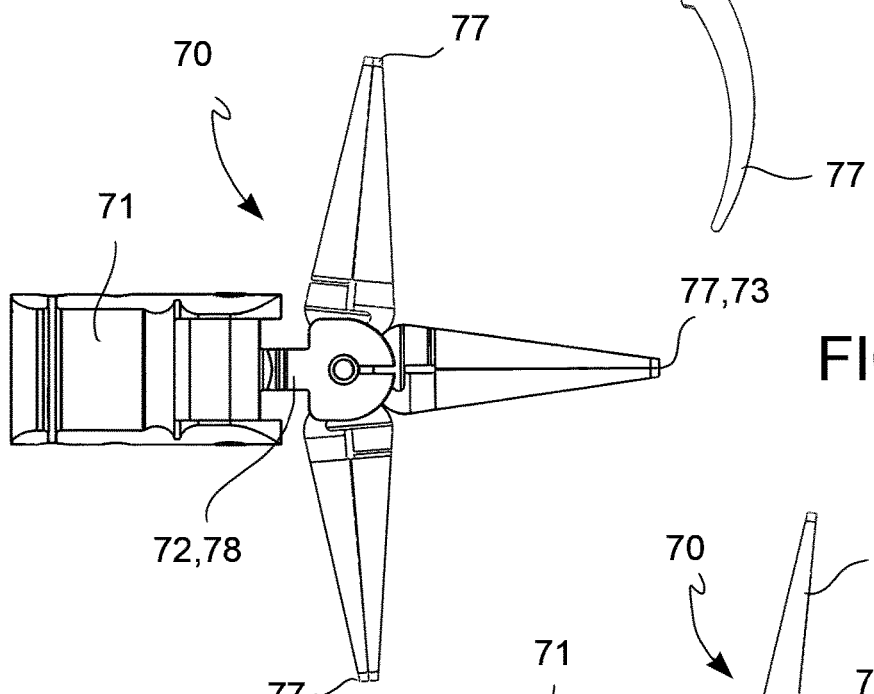
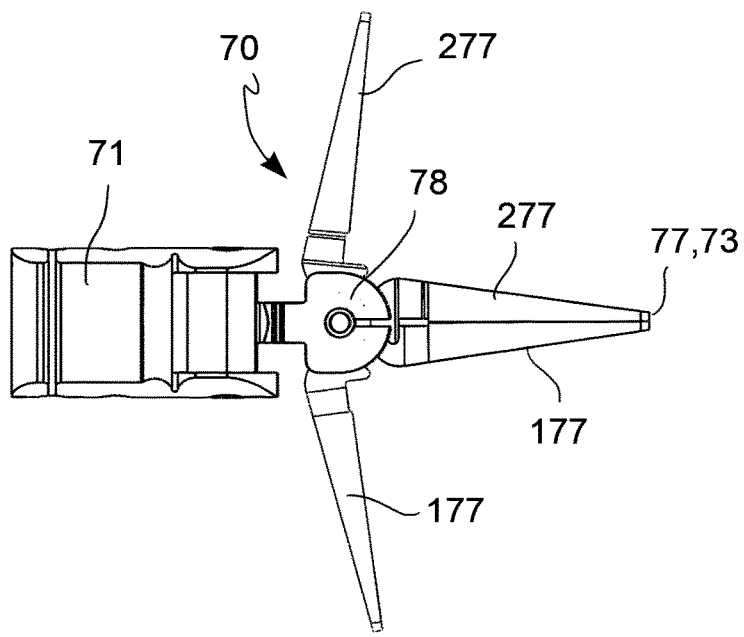

ROBOTIC SURGICAL ASSEMBLY

This application is a National Stage Application of PCT/EP2016/074805, filed 14 Oct. 2016, which claims benefit of Ser. No. 10/201,5000062500, filed 16 Oct. 2015 in Italy and which applications are incorporated herein by reference. To the extent appropriate, a claim of priority is made to each of the above-disclosed applications.

FIELD OF INVENTION

The present invention relates to a robotic assembly for surgery.

In addition, the present invention relates to a method of moving a robotic surgical assembly.

STATE-OF-THE-ART

Robotic assemblies for surgery or microsurgery comprising multi-joint robotic arms terminating with surgical instruments are known in the field. For instance, document US-71553116-B2 discloses a robotic assembly for performing brain microsurgery under MRI (Magnetic Resonance Imaging) guidance comprising an MRI-based image acquisition system and two multi-joint arms, each with three rotary joints with vertical axes to avoid direct gravity loads (as shown for instance in FIG. 7 of said document U.S. Pat. No. 7,155,316-B2), each connected to its respective end-effector endowed with an internal degree of freedom of motion for gripping.

Solutions available in the state-of-the-art, although offering partial advantages, require a motion strategy that simultaneously involves a plurality of independent movements even for small motions of the surgical instrument in the operating work-field, which results both in a difficult control of the kinematic accuracy and in a large encumbrance in the operating work-field, that in practice becomes inaccessible to the Surgeon. As a matter of fact, the application field of the majority of robotic assemblies for surgery that are based on the master-slave paradigm are dedicated to use in minimally invasive surgery (or MIS), such as laparoscopic or endoscopic surgery. In both such applications, the kinematics of the robotic assembly is aimed to optimize the access of the surgical instruments to the operating field through the surgical ports or orifices, a feat that requires the coordination of a plurality of degrees of freedom of movement. In contrast, surgical, and microsurgical, applications in open surgery require an accurate kinematic control of translational movements, over a workspace limited by the field of view of the operating microscope, without the limiting kinematic constraints represented by the surgical ports or natural orifices, and thus benefit hugely from the surgeon's ability to directly access the operating field.

It is also notable that the execution of the principal surgical primitives, such as tissue tensioning and anastomotic suturing, requires the ability to orient the surgical instrument tip in a large spatial cone of directions and to rotate the instrument around its longitudinal axis (roll), for example to guide the needle through the tissue with the tip of the needle holder instrument, in a similar manner as the human hand is jointed at the wrist and the elbow.

Robotic assemblies for surgery or microsurgery comprising a teleoperated master-slave system are generally known, as described, for example, in document U.S. Pat. No. 6,963,792-A and, more specifically for the microsurgical application by U.S. Pat. No. 6,385,509-B2, and US-2014-0135794-A1, that describe kinematic solutions for the movement of the surgical instrument tip that require coordination of a plurality of joints in a serial kinematic chain that clutter the operating field. Such encumbrance effect is increasingly pronounced as the joints articulating the tip of the instrument are further away from the tip itself. Moreover said micro-surgical systems do not allow adequate movement, and more specifically adeguate reorientation, of the instrument tip when in an operating site inside a lesion as little as 10 centimeters from the surface of the skin.

Generally, even a specialized operator requires long training to acquire mastery of the master command devices adopted in known master-slave systems. In fact, known master devices have a long learning curve, primarily because they are mechanically linked to motion recording stations, which necessarily limit their movement in an unfamiliar way and often are of large dimensions. Hence, know master devices are intrinsically unfit to replicate the function of traditional open surgery instruments and lack the ability to carry out a large spectrum of linear as well as angular movements in three dimensional space.

For example, document U.S. Pat. No. 8,521,331-B2 discloses a robotic device for laparoscopic surgery, where the master command device has a shape that allows the surgeon to wear it as a glove on his-her fingers. According to another embodiment shown in FIG. 2B of said patent, the master command device has a joystick shape, attached on one part to the surgeon's wrist and extends so that it is held with just one hand, comprising a cylindrical stem having a pair of lateral wings that can register the grip movement. A surgeon makes use of a laparoscopic display device integral to said command device.

The above solution, although partly advantageous for laparoscopic surgery, does not entirely solve the issue, making long training still necessary for the surgeon before becoming proficient at handling said command devices instead of the familiar open surgery instruments.

As is well known, the practice of microsurgery requires the use of either an optical microscope or magnifying loupes, demands an high level of dexterity and experience of the surgeon, who works at the limits of physiological tremor and the accuracy that human hand motions can reach at such dimensional scale.

The adoption of robotic technologies can bring about great benefits, allowing both a high degree of miniaturization of the instruments and scaling the size of the movements in the operating field, hence eliminating the effect of physiological tremor and easing the manual task. For example, microsurgical procedures are carried out in several phases of the reconstruction of biological tissues, such as for example in the execution of blood vessel anastomosis, comprising small diameter vessels, and nerves. Such procedures are carried out to reconstruct anatomy after the occurrence of traumatic lesions or of lesions produced by surgical removal of tissue, to reattach limbs and to revascularize tissues, all performed in an open surgery set-up given the pre-existence of a superficial lesion.

Others examples of application of microsurgical techniques are found in transplant surgery, neurosurgery or in vascular surgery, as well as in surgery around and inside the eye, and in the inner ear, as in the case of cochlear implants. Also the prominent surgical procedure of cardiac by-pass comprises the critical step of anastomosis of the coronary arteries. The need for instrument miniaturization is also felt in other surgical techniques, for example in minimal invasive surgery, such as laparoscopy and endoscopy, that are aimed at limiting the invasiveness of surgical instruments on biological tissue. With reference to laparoscopy, the technical solutions known in the art do not allow a satisfactory miniaturization of the diameter of the laparoscopic instruments employed in Single Incision Laparoscopic Surgery or Single Port Surgery. Moreover, it is worth noticing that the endoscopes typically employed in MIS have an instrument channel with a diameter between 1 mm and 3.2 mm. Such dimensions limit the functionality of current surgical instrumentation available through the endoscope instrument channel, which at present is typically just capable of gripping action.

Medical instruments comprising a jointed device suitable to work on the patient, are generally known in the art. For example, document WO-2010-009221-A2 shows a robotic surgical instrument comprising a distally jointed device, capable of providing three degrees of freedom of motion, respectively pitch, yaw and grip, employing just four actuation cables. Such cables slide inside guiding channels, or sheaths, present inside the body of the articulating device.

Said technical solution limits the miniaturization of the robotic articulating device, because friction between the guiding channels surfaces and the cables that slide inside them limits the positioning precision achievable by the articulating device. As it is known in the art, as the physical dimensions of a medical instruments are reduced, difficulties arise which are related to the increase of relevance of superficial forces, such as friction, that become dominant over volume forces. Such a phenomenon requires to resort to solutions that minimize friction forces, and at the same time reduce lost motions of mechanics to a minimum. The loss of positioning precision of an articulating device is a fundamental technological obstacle to further miniaturization of articulating instrument, since, with miniaturization, also the stiffness of the driving members (tendons) goes down with the second power of their diameter, making it even more difficult to overcome friction for the precise positioning of the instrument tip. Moreover such a solution requires a tendon guiding system comprising channels and guiding surfaces that surround the cables that make the pitch and yaw links, as well as the instrument shaft, very difficult to miniaturize using known fabrication methods, such as for example injection molding and machining, and would be prone to have several locations of mechanical weakness.

There is a felt need for a surgical robotic assembly able to carry out precise motions and simply control a wristed medical instrument within the surgical workspace, for example an anatomical district of a patient. At the same time, there is a need to develop a reliable robotic assembly characterized by a simple driving method without compromising its precision. Furthermore, there is a need for a robotic assembly that is more versatile than known assemblies and is able to carry out a wider variety of surgical procedures.

Therefore, the need is felt to provide a robotic surgical assembly suitable for positioning all the end effectors in a working volume with a unique movement, without increasing the encumber of such robotic surgical assembly.

For example, document U.S. Pat. No. 5,876,325-A shows a robotic surgical assembly having two opposite articulated arms for operating on a patient. This solution fails to show an accurate relative positioning of the end effectors and it requires a continuous monitoring of the relative position of the two end effectors. A similar solution is shown in document U.S. Pat. No. 6,731,988-B1, disclosing master-slave driven robotic surgical assembly having two end effectors.

The need is felt to provide a robotic surgical assembly having a kinematic structure suitable for positioning all the end effectors in the same working volume, in a reliable and precise manner yet rapid and simple.

For example, document US-2006-087746-A1 shows a robotic surgical assembly having two end effectors, wherein each end effector comprise a built-in motor compartment. The provision of a motor compartment located at the end effector causes an increase in temperature of the end effector, and thus results in an invasive tool for surgery.

Moreover, there is a felt need to provide a driver device for microsurgery, suitable to form a master interface in a robotic assembly for microsurgery that comprises a master-slave type teleoperation system which is simpler and more intuitive to manipulate for the microsurgeon than known solutions, without limiting its functionality. Equally, there is a felt need to provide a master interface, which can be mastered more quickly and easily by the surgeon. Furthermore, there is a felt need to provide a command device that is more versatile than the known solutions and can be applied to different types of microsurgical procedures.

Hence there is a felt need to provide a jointed or articulated medical instrument, or an assembly comprising an jointed or articulated device, which is structurally and functionally suitable for extreme miniaturization without compromising its reliability and safety. There is also a felt need to provide a jointed or articulted medical instrument, or an assembly comprising a jointed device, suitable for carrying out a wide variety of medical-surgical therapies. Finally, there is a felt need to provide a jointed or articulated medical instrument, or an assembly comprising an jointed or articulated device, that is durable and able to undergo periodic maintenance without compromising its sterility or reliability.

There is a felt need to provide a jointed or articulated medical instrument, or an assembly comprising a jointed device, that requires simplified manufacturing compared to known solutions.

There is a felt need to provide a driver device based on tendons, or actuation cables, for a medical instrument suitable to be subject to extreme miniaturization, without compromising its precision or reliability in use.

SOLUTION

One of the goals of the invention described here is to overcome the limitations of known solutions described above and to provide a solution to the needs mentioned with reference to the state of the art.

FIGURES

Figure 1A:
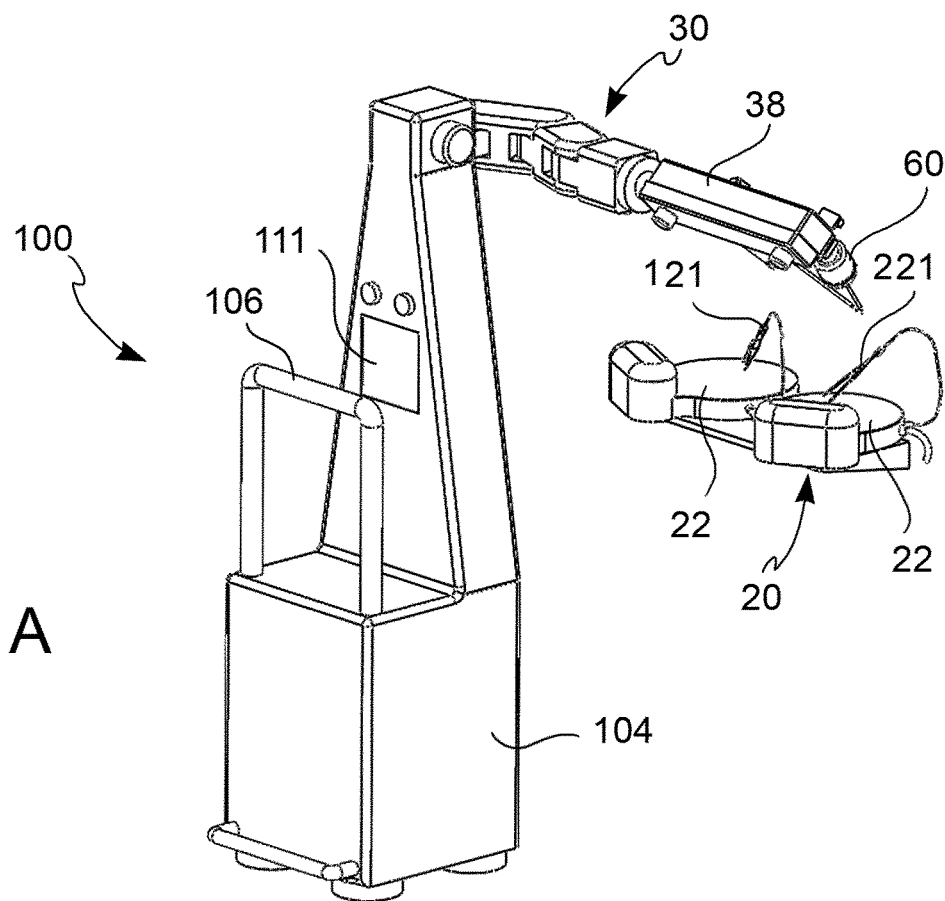
Figure 1C:
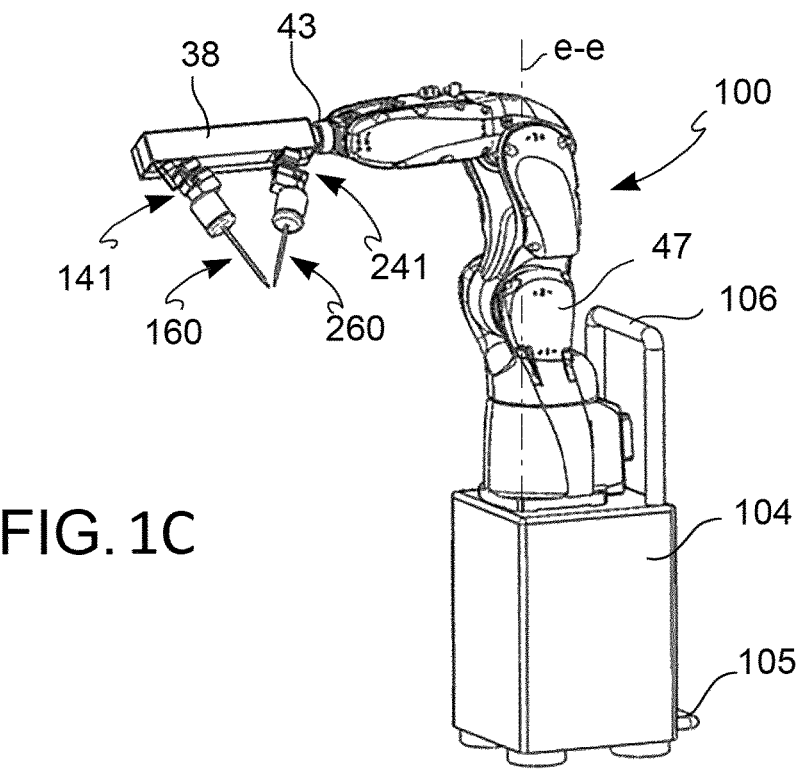
Figure 2A:
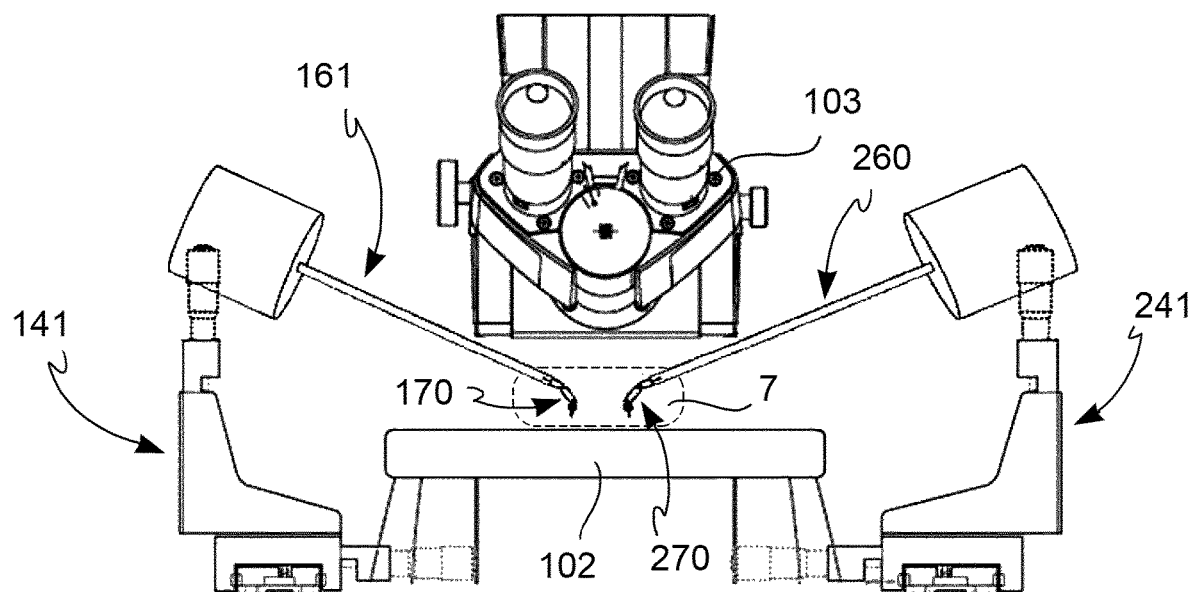
Figure 2B:
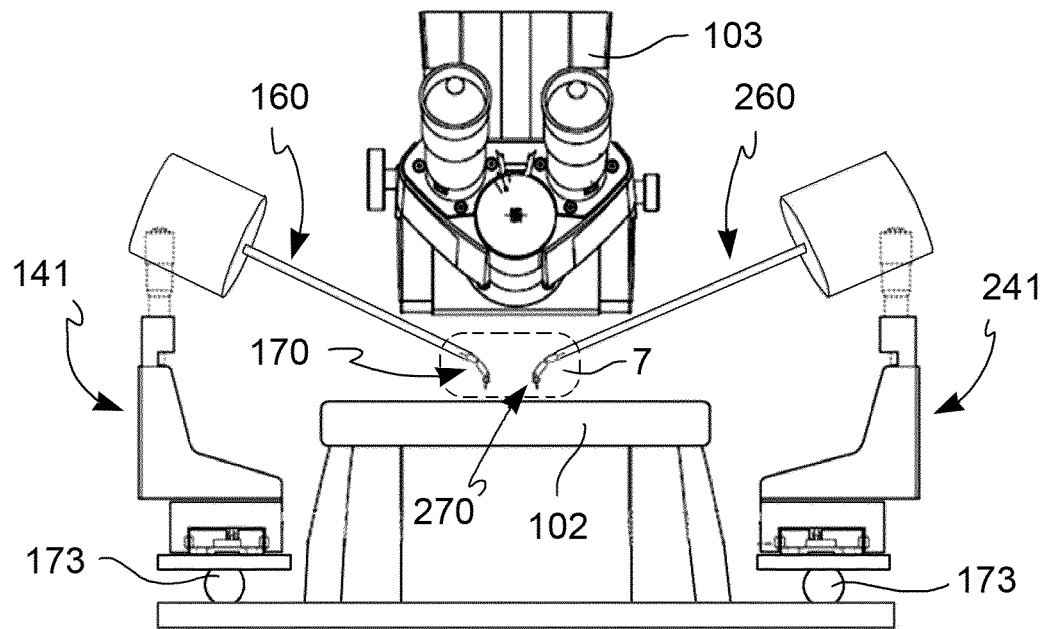
Figure 3:
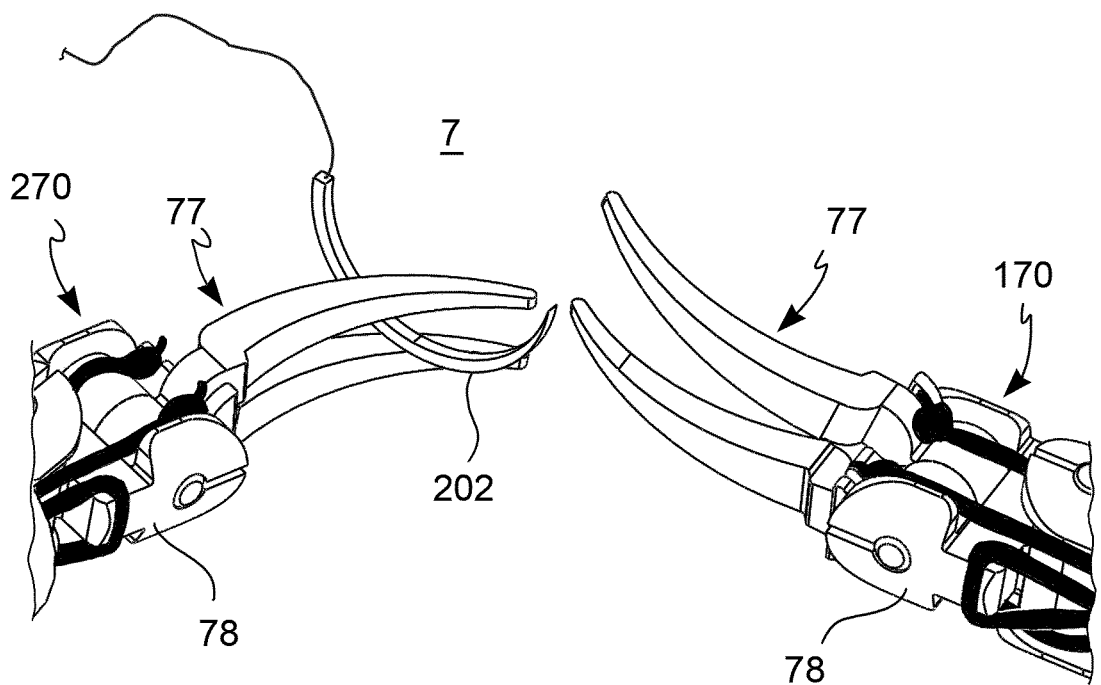
Figure 4B:
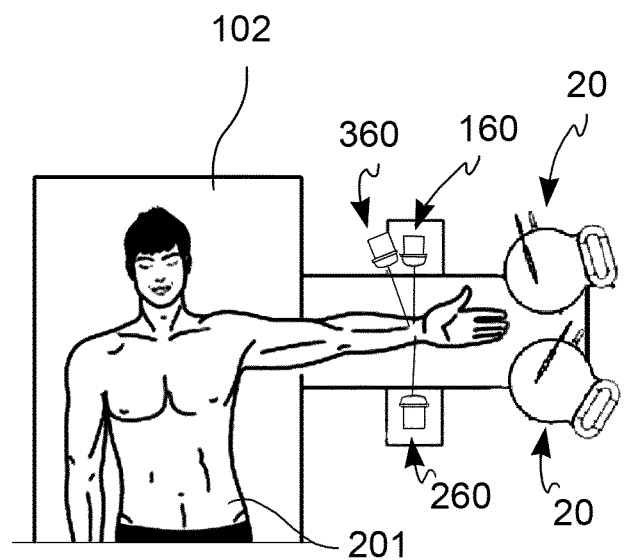
Figure 4A:
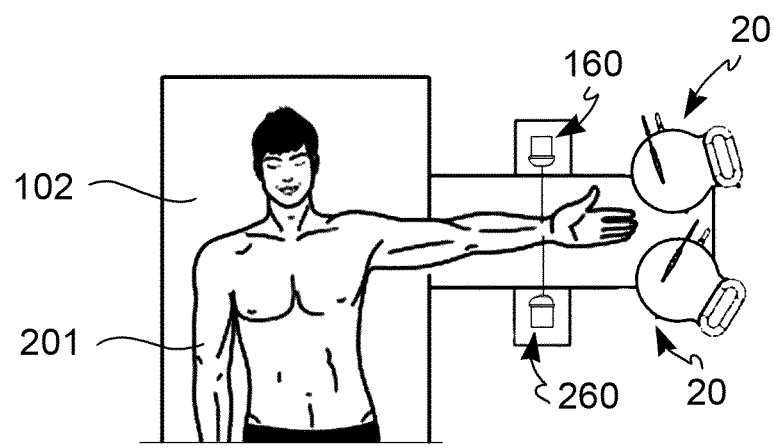
Figure 5:
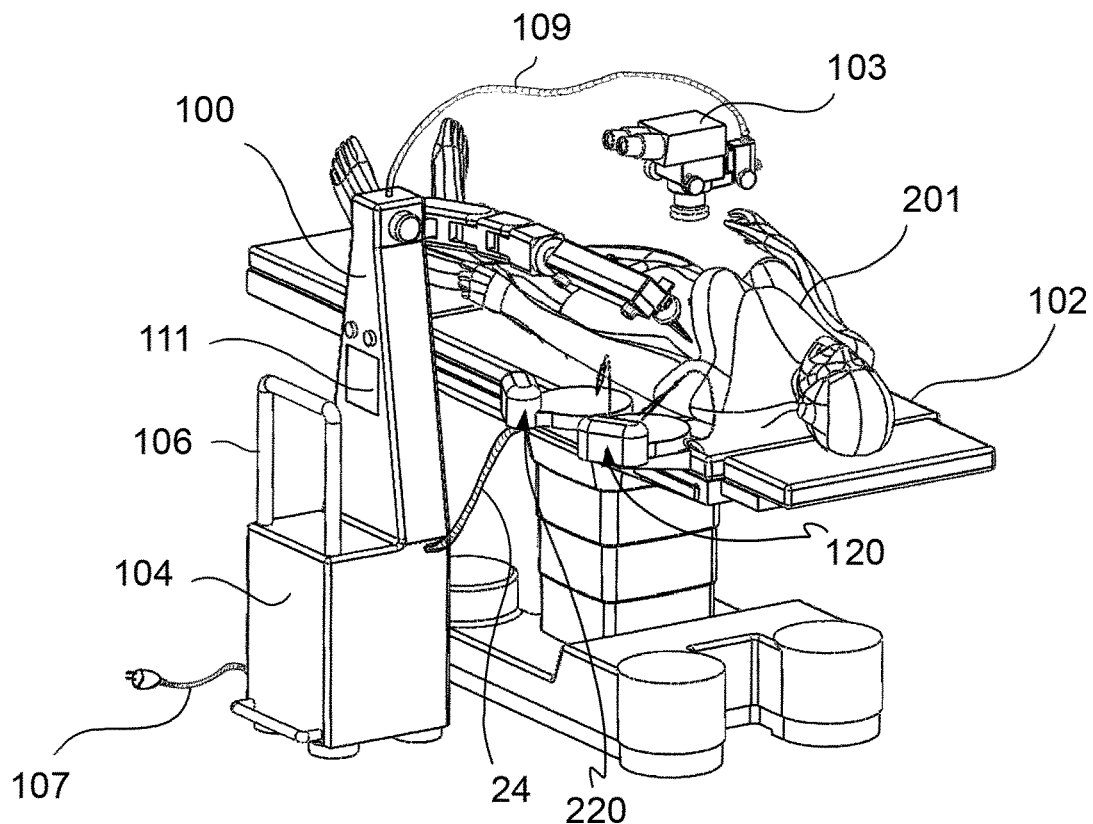
Figure 6:
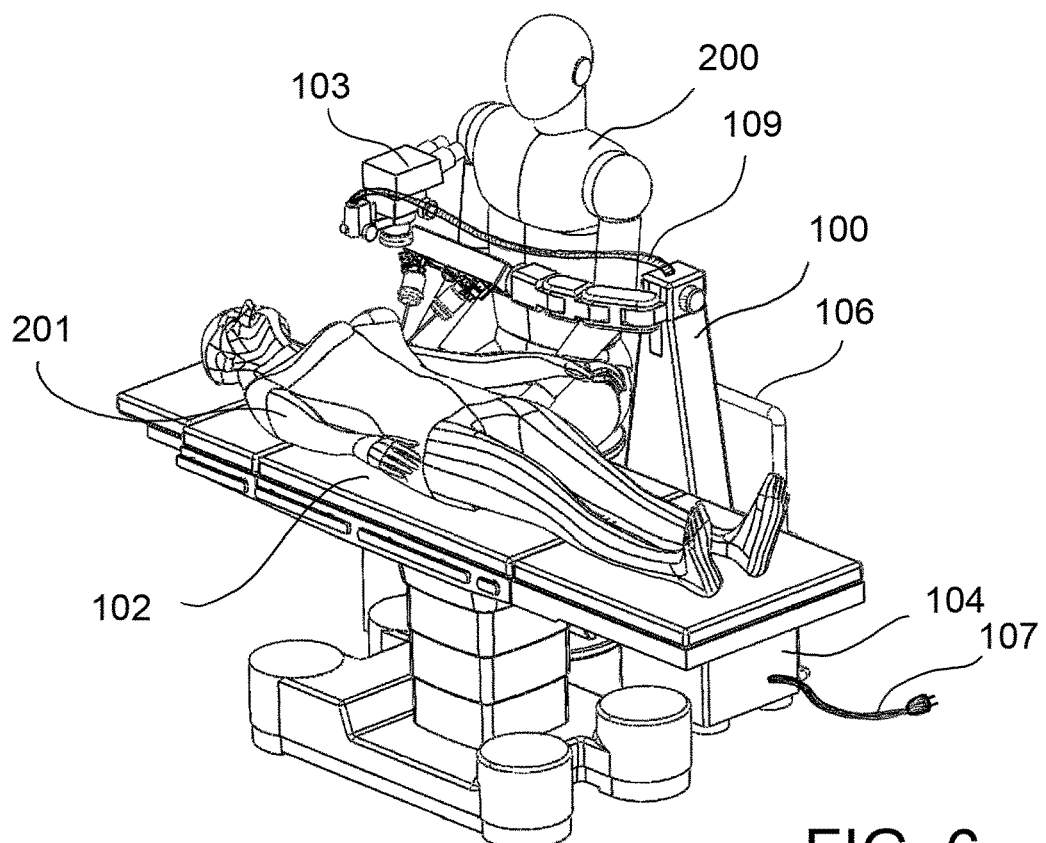
Figure 7:
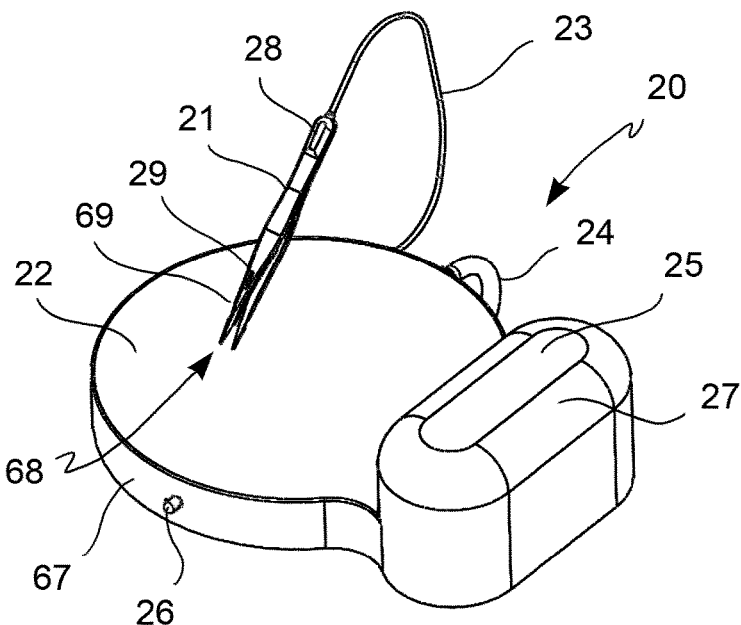
Figure 8:
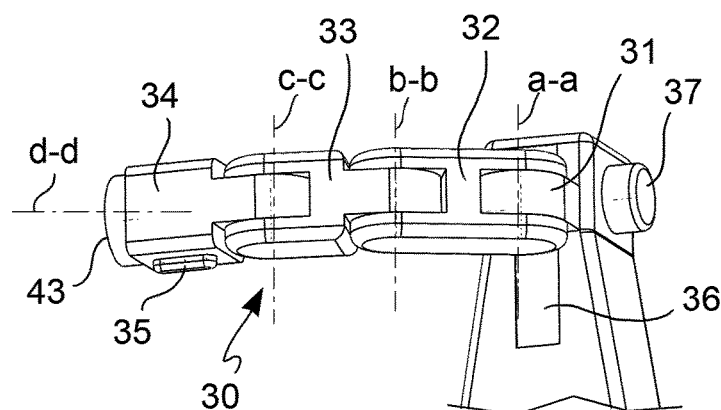
Figure 9A:
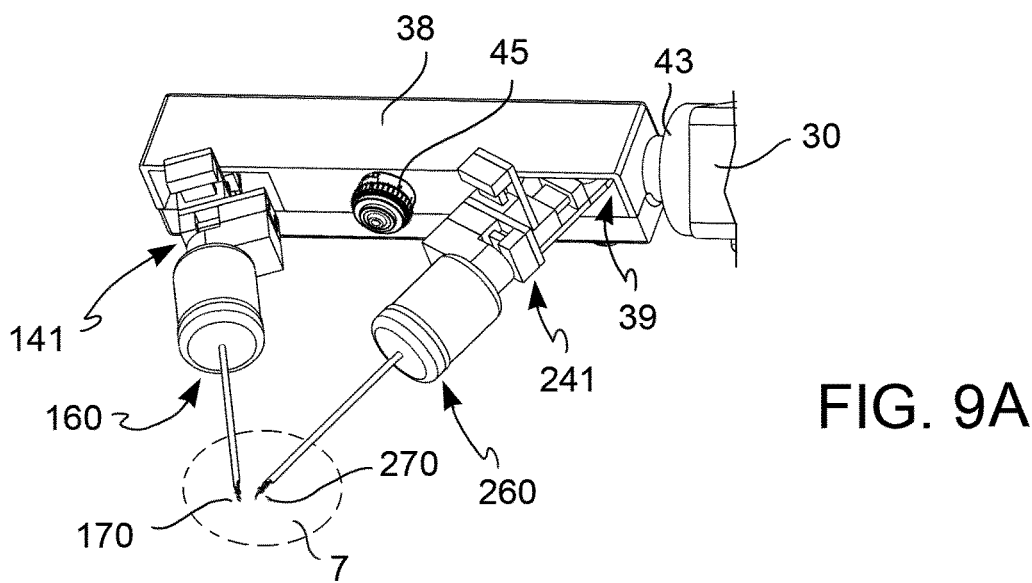
Figure 9B:
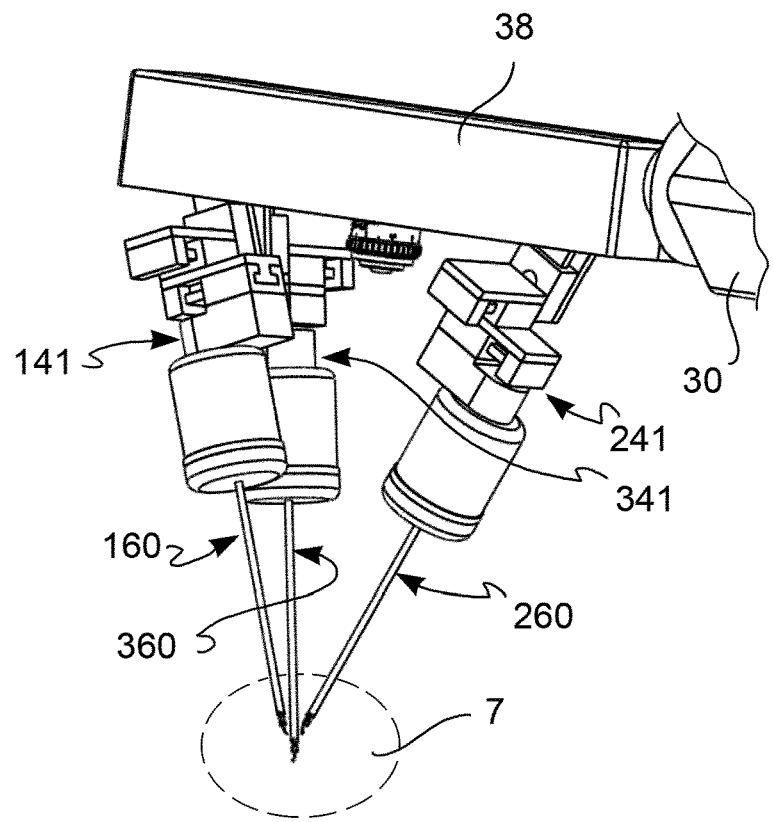
Figure 9C:
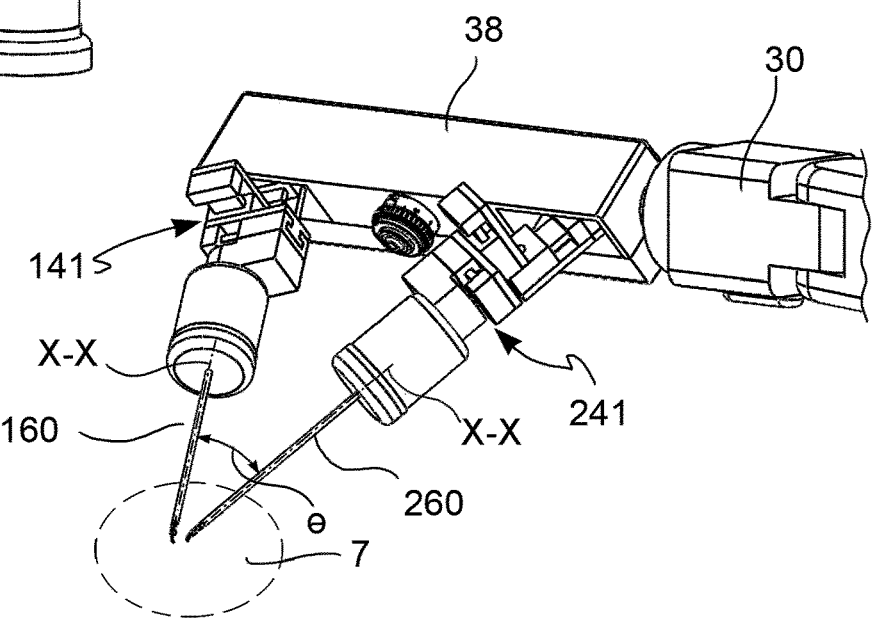
Figure 9D:
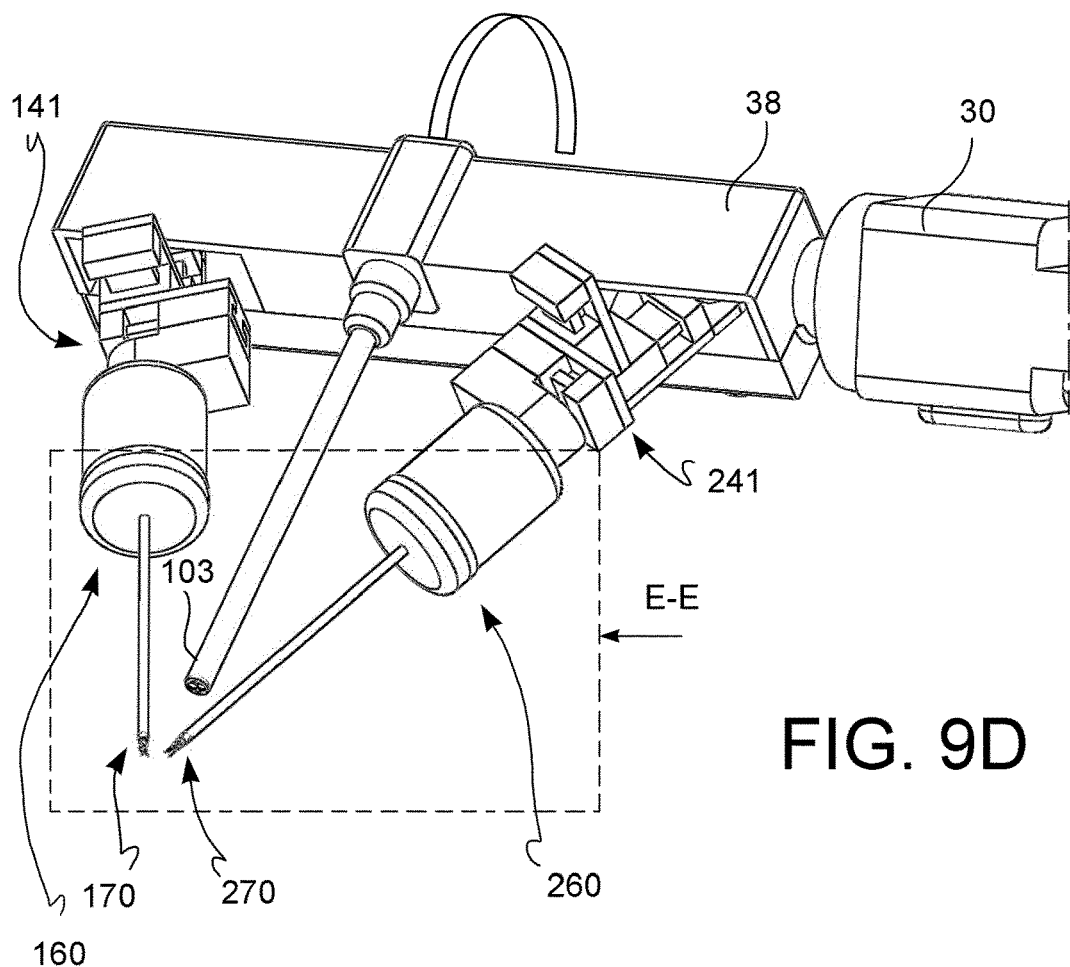
Figure 9E:
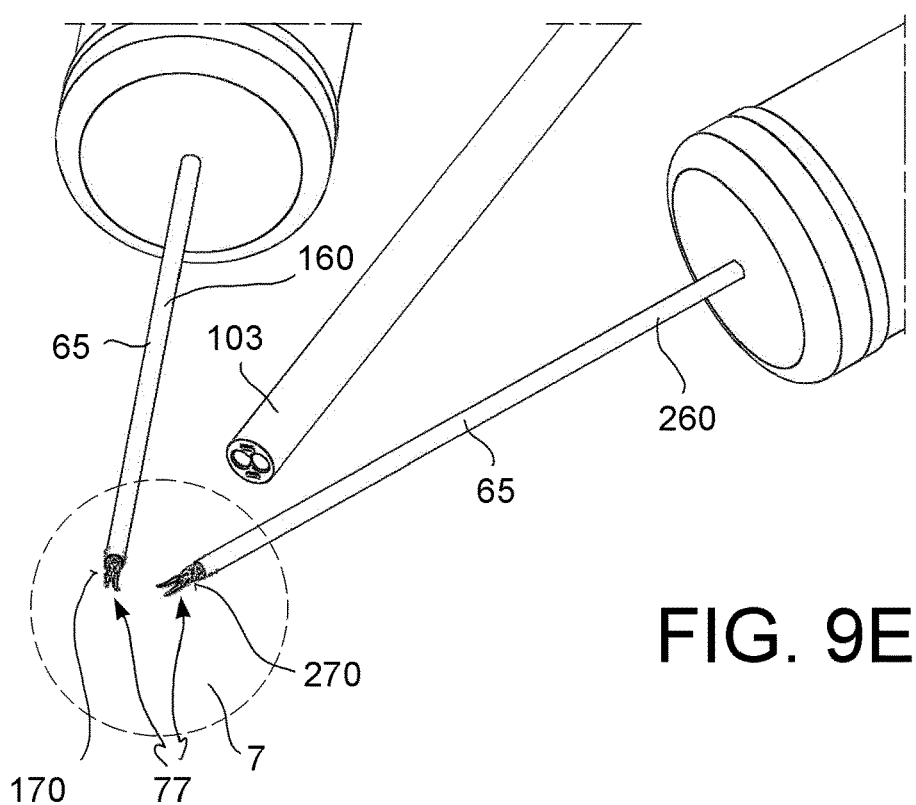
Figure 10:
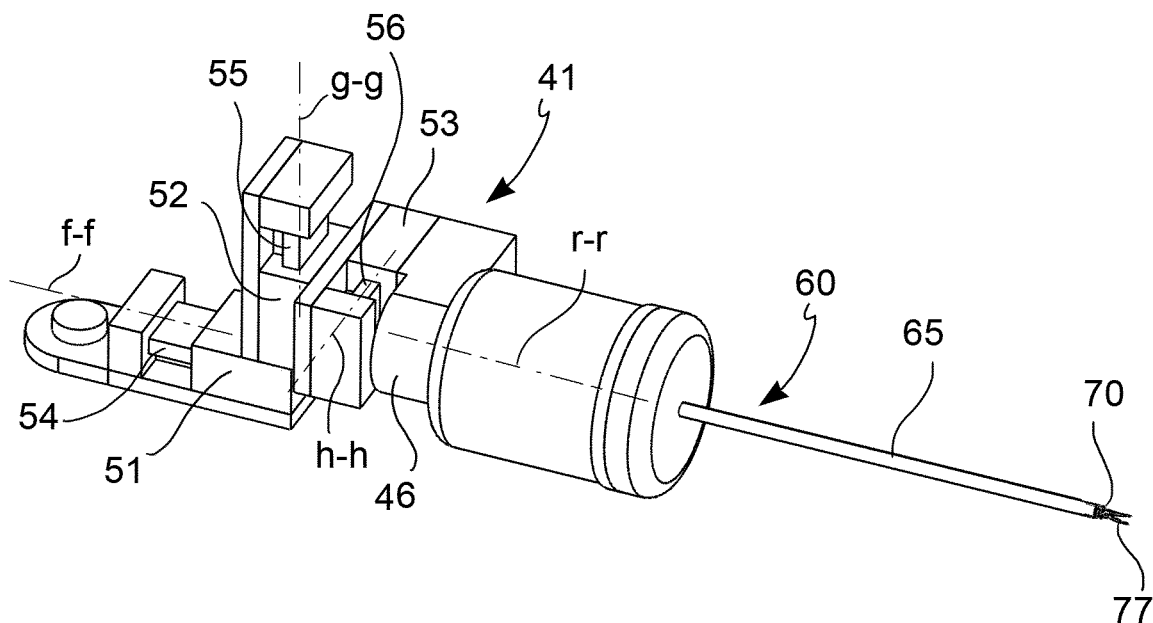
Figure 11:
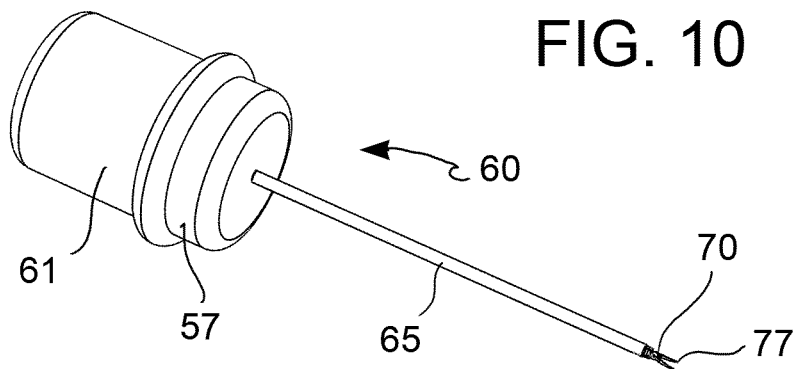
Figure 12:
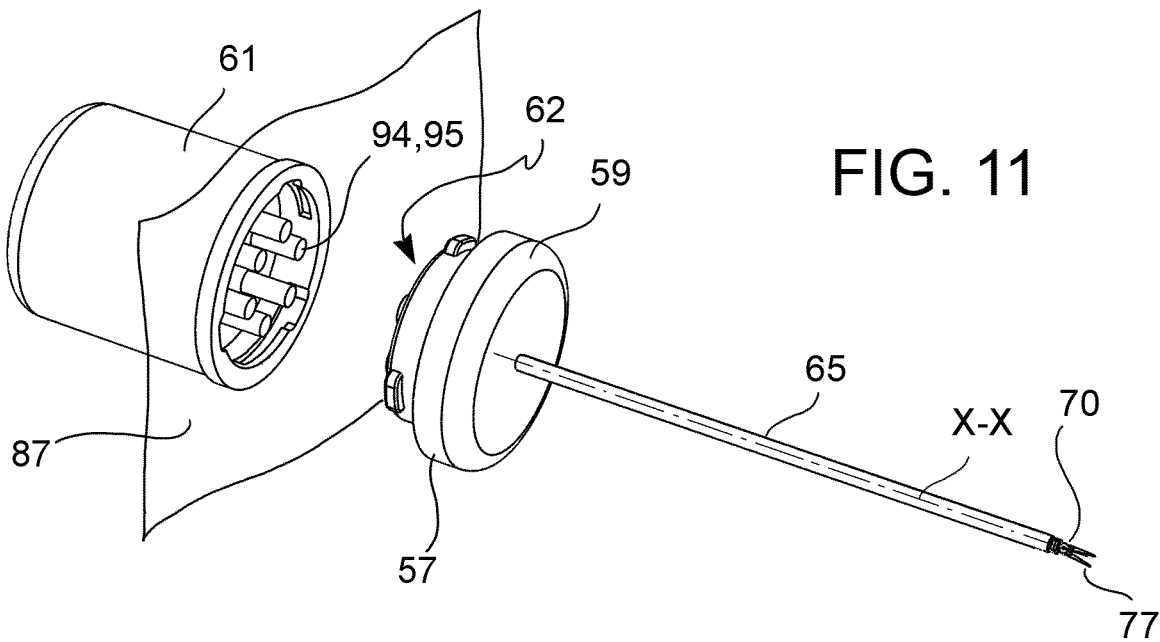
Figure 13A:
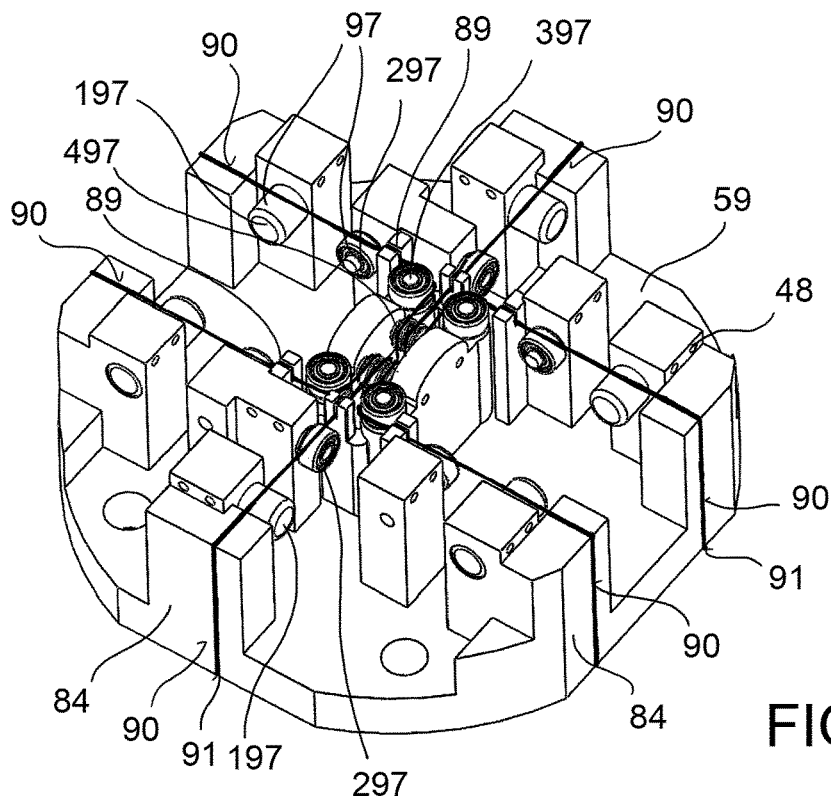
Figure 14A:
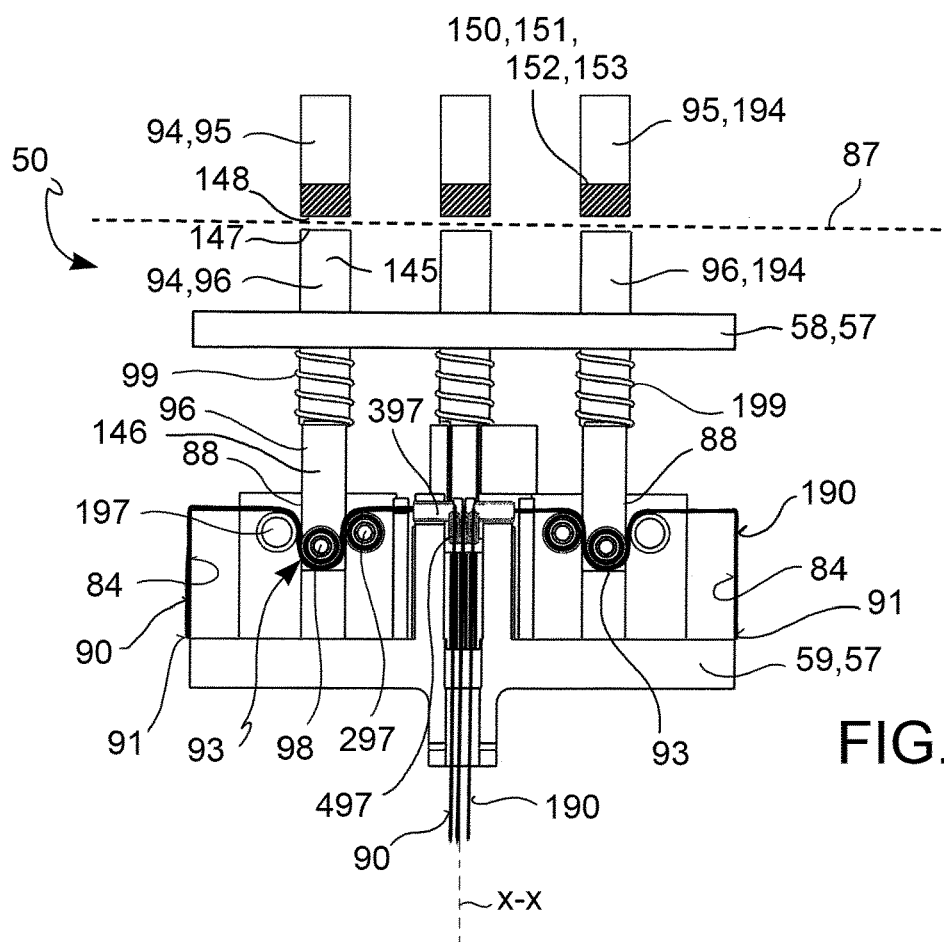
Figure 35:
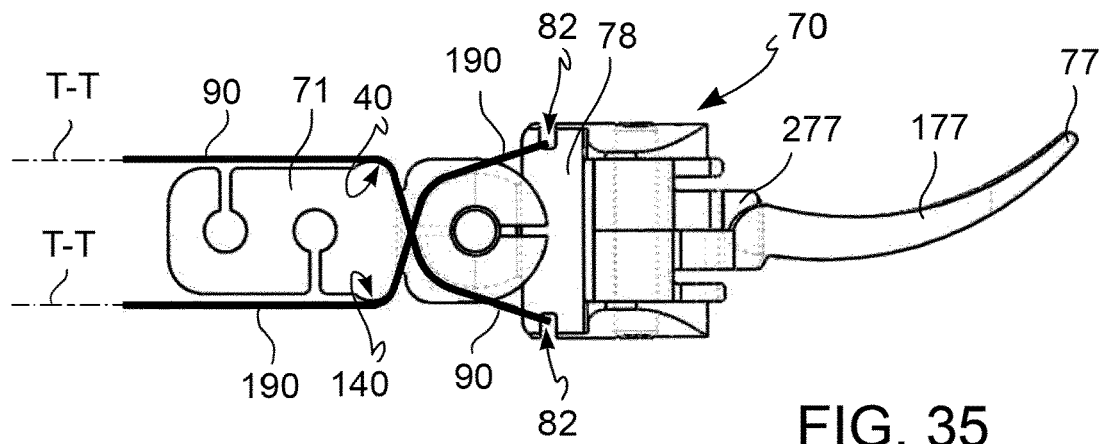
Figure 36:
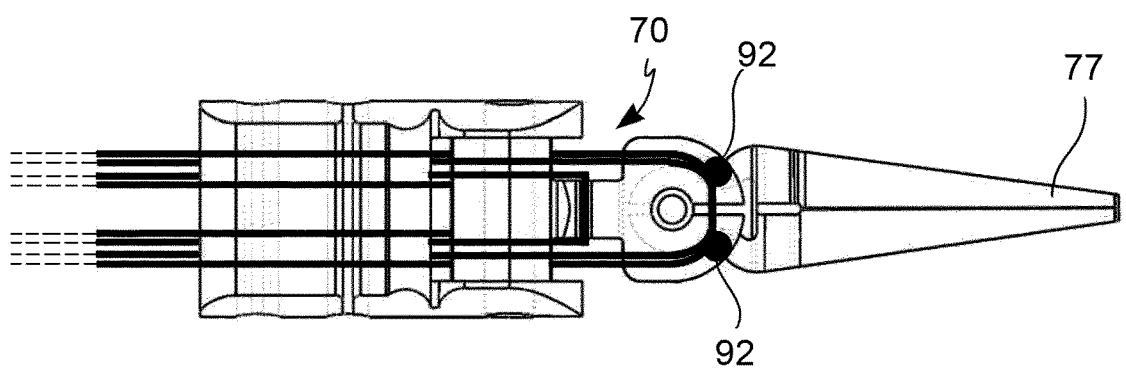
Figure 13B:
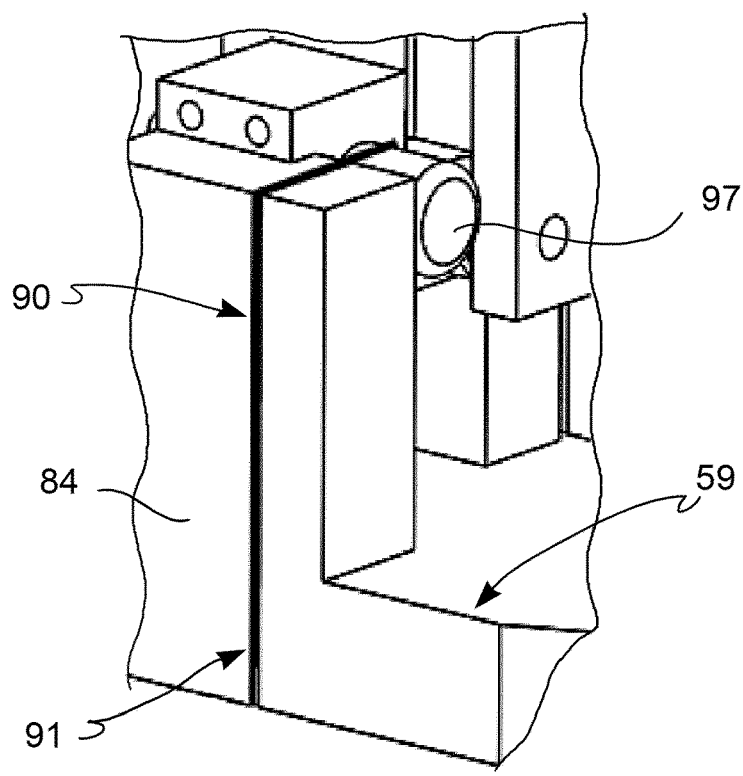
Figure 14B:
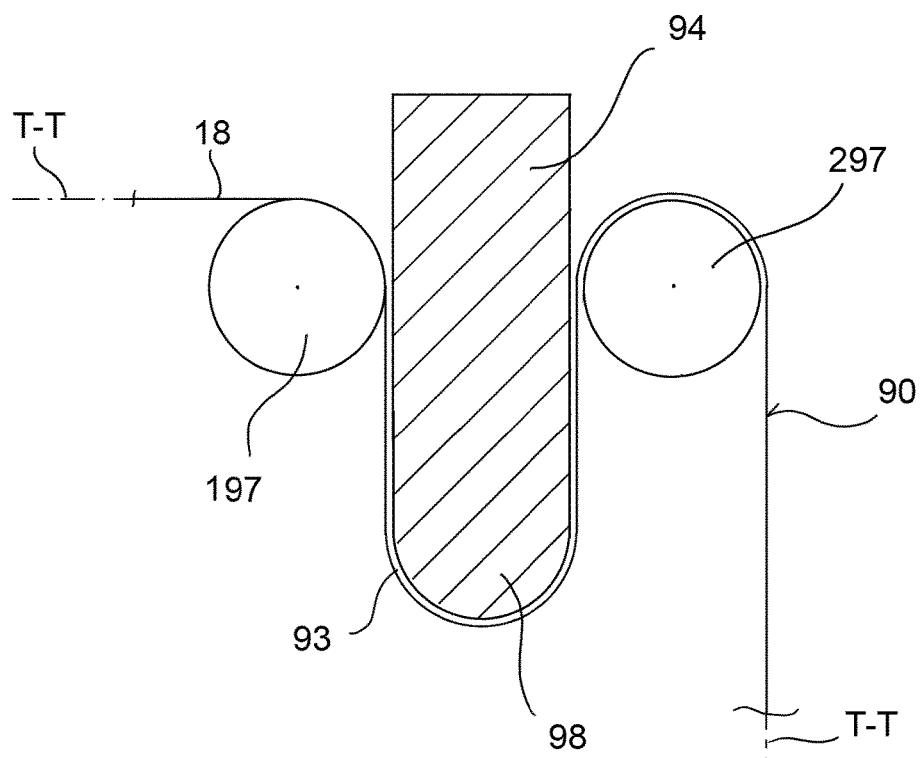
Figure 15A:
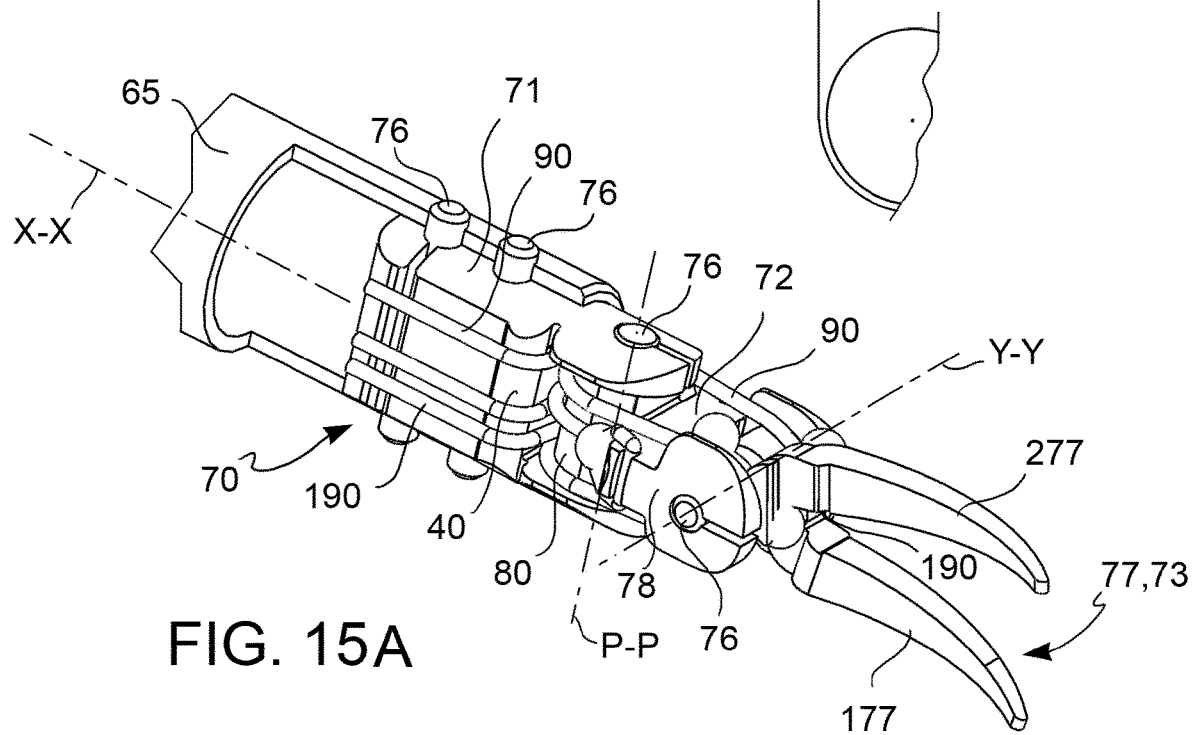
Figure 16:
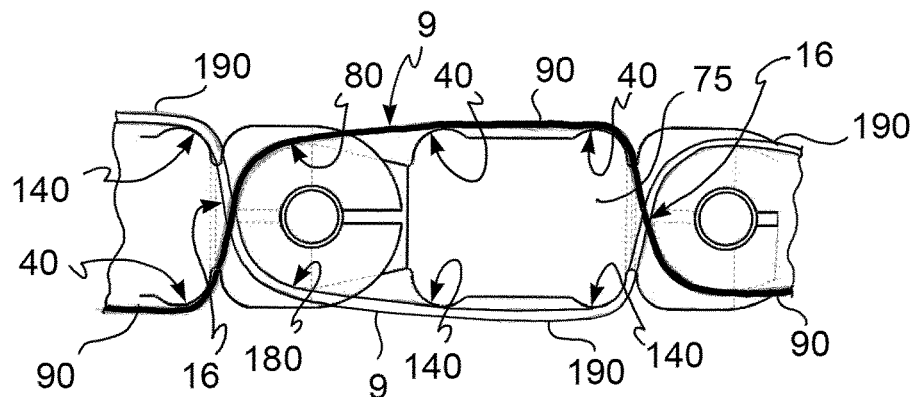
Figure 17:
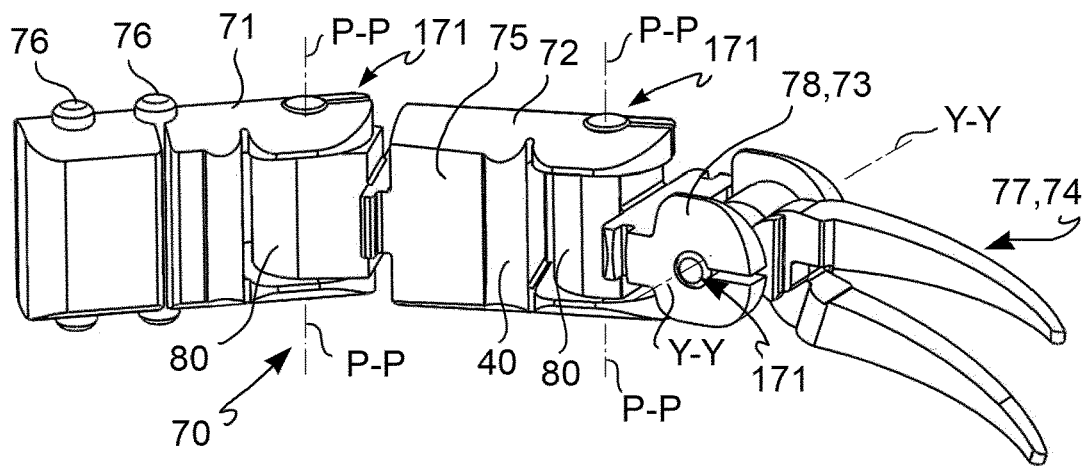
Figure 15B:
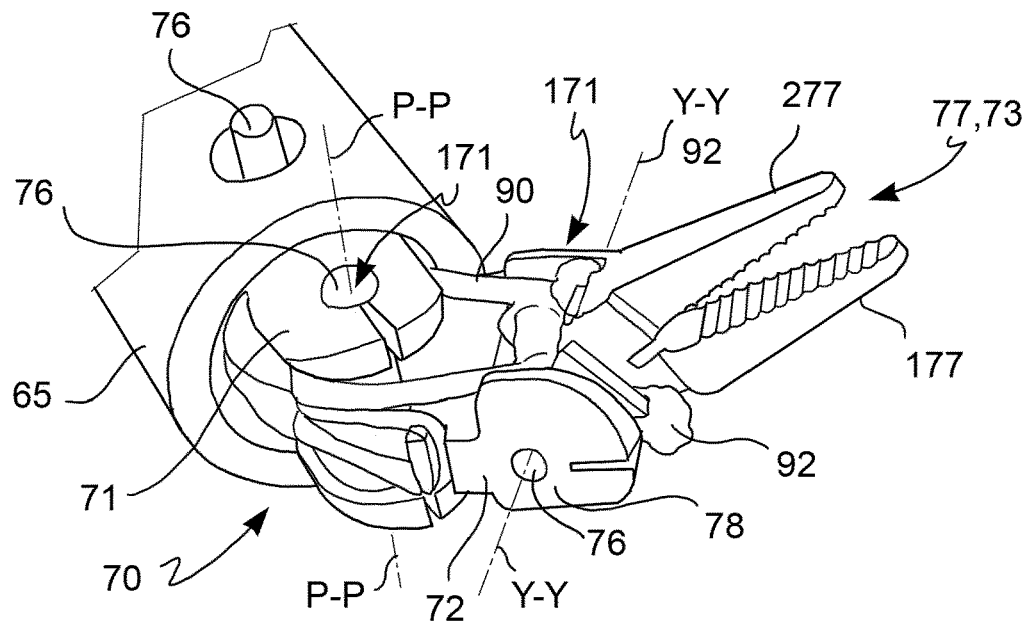
Figure 15C:
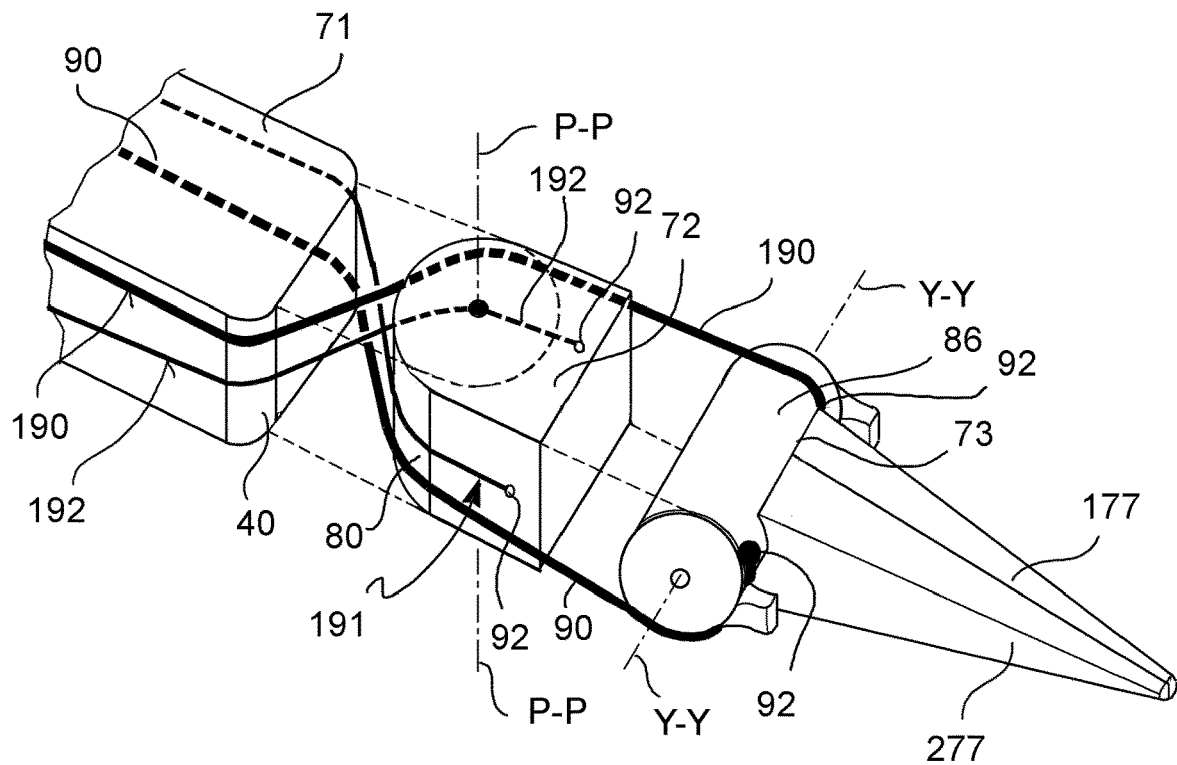
Figure 15D:
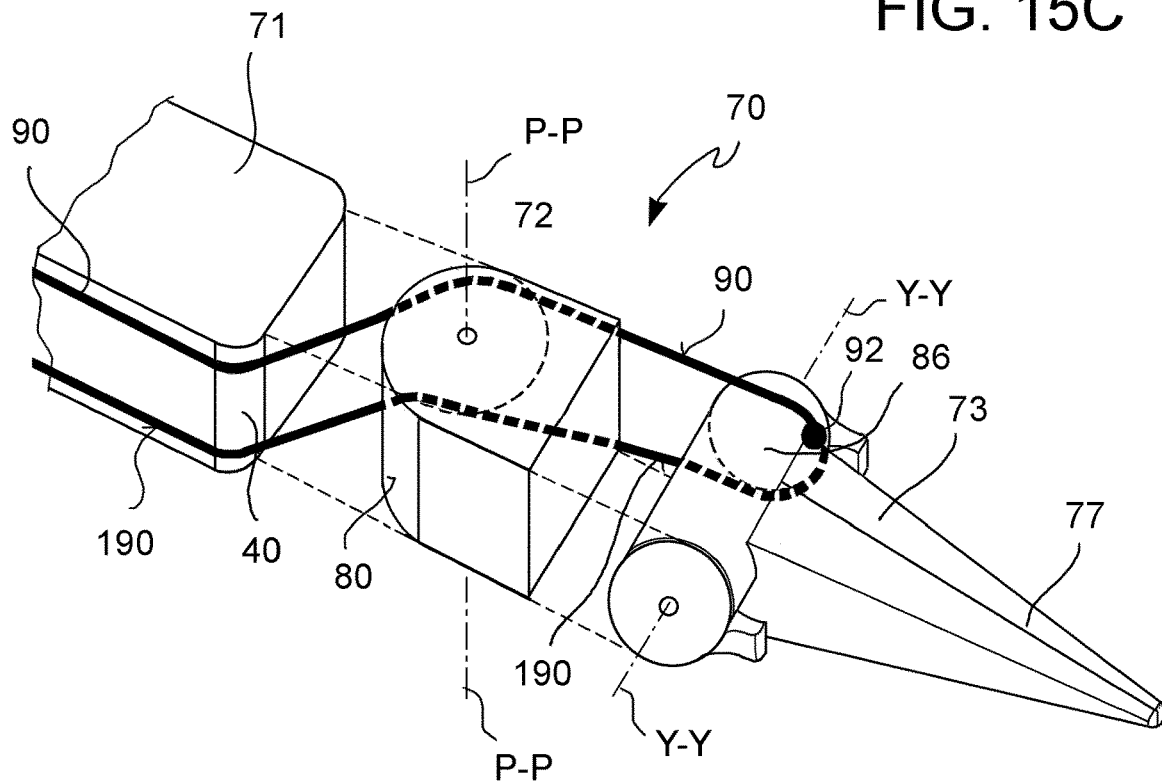
Figures 18, 19:
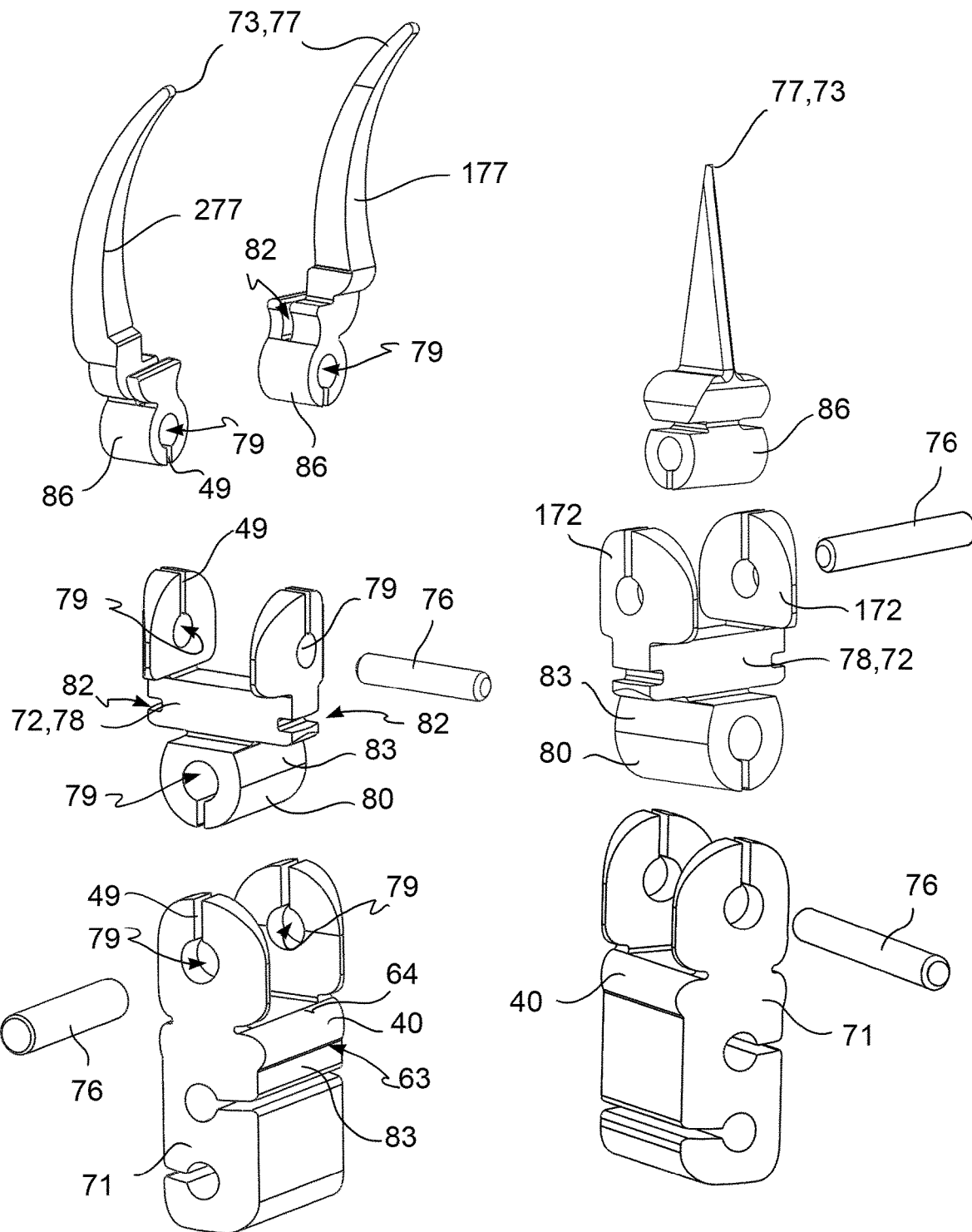
Figures 20, 21:
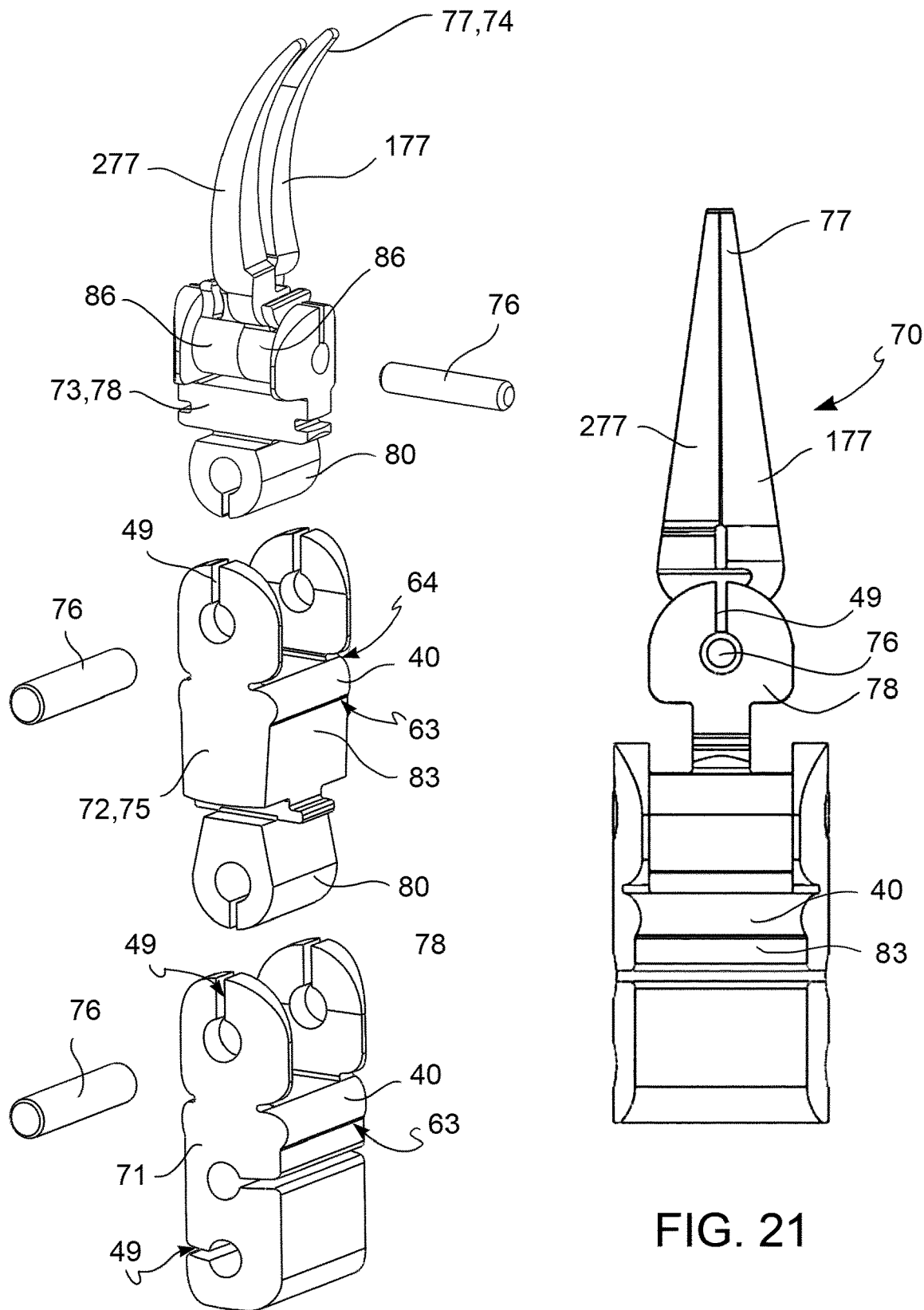
Figure 25:
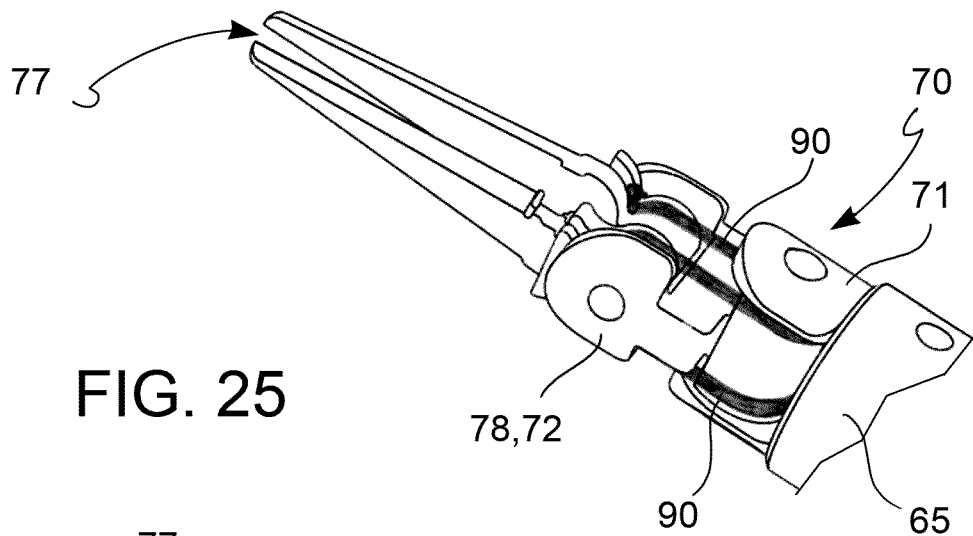
Figure 26:
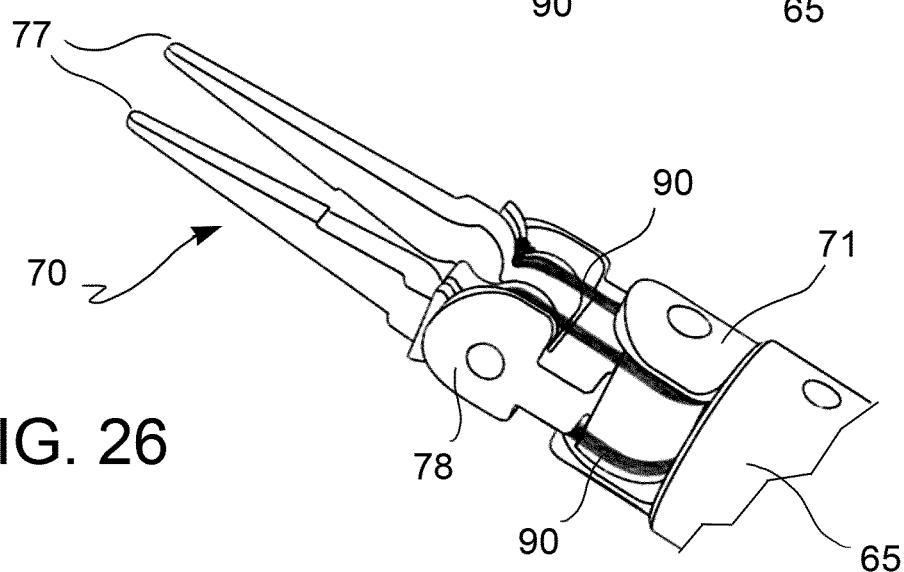
Figure 27:
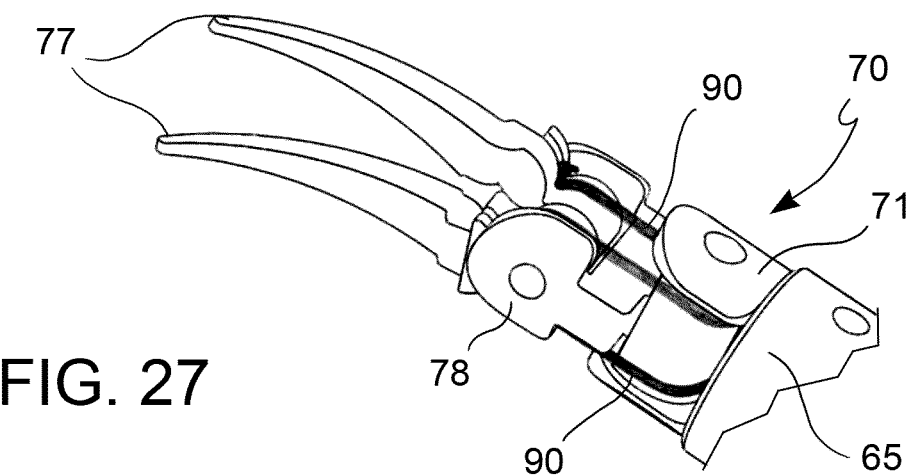
Figures 28, 29:
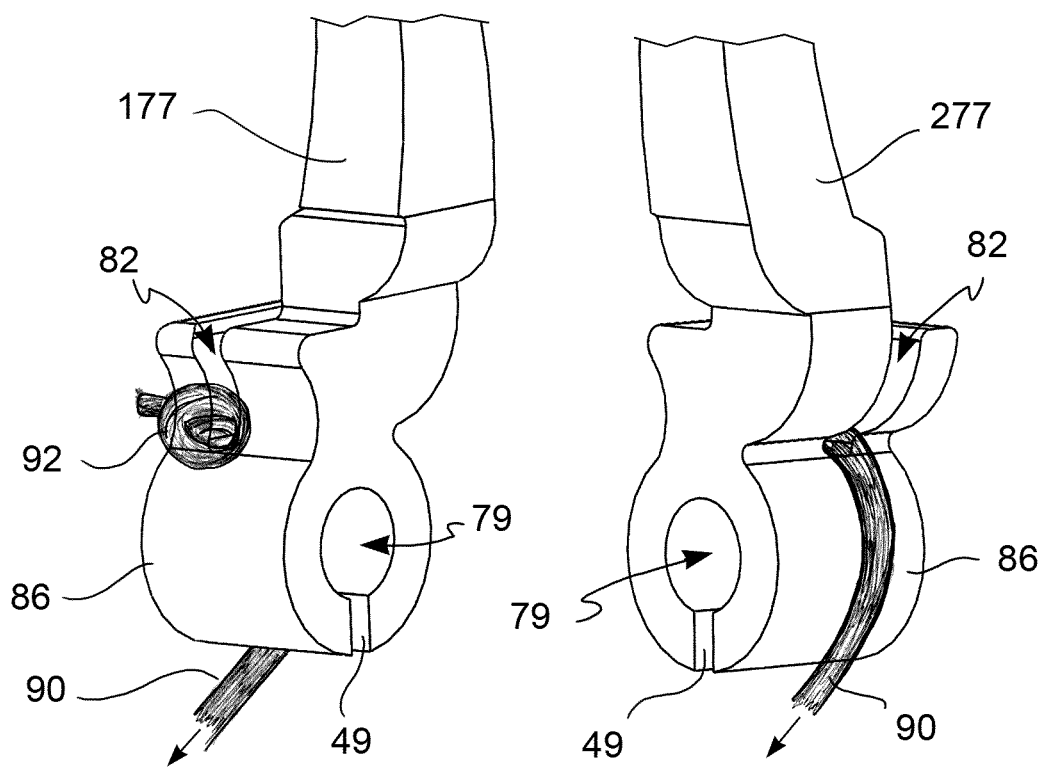
Figure 30:
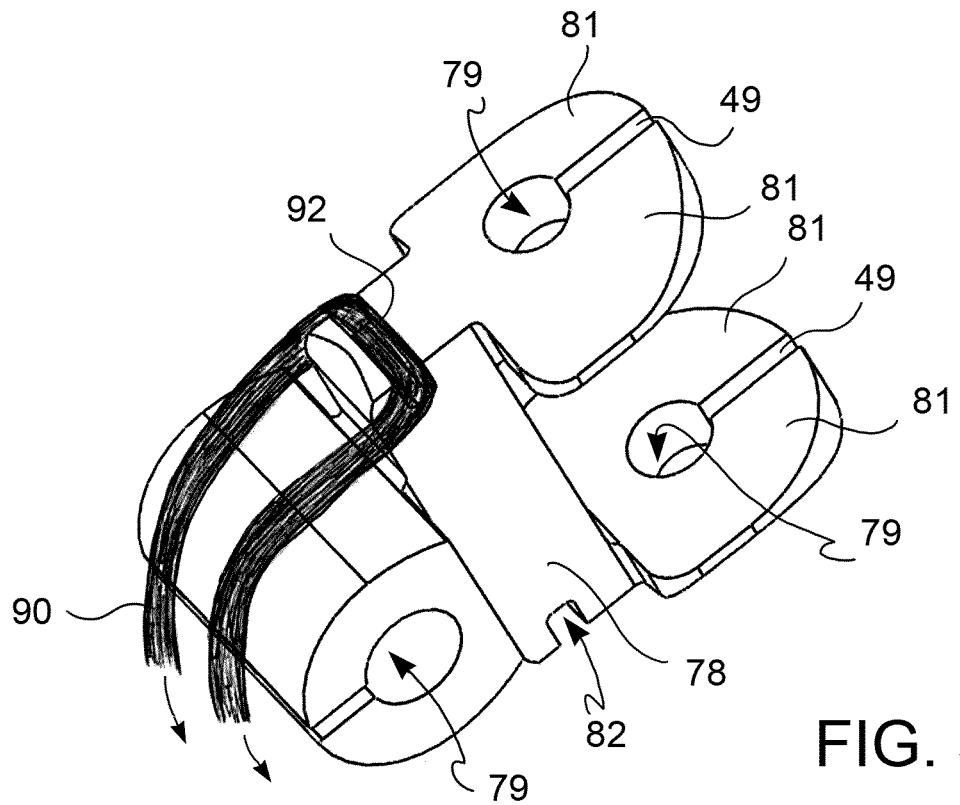
Figure 31:
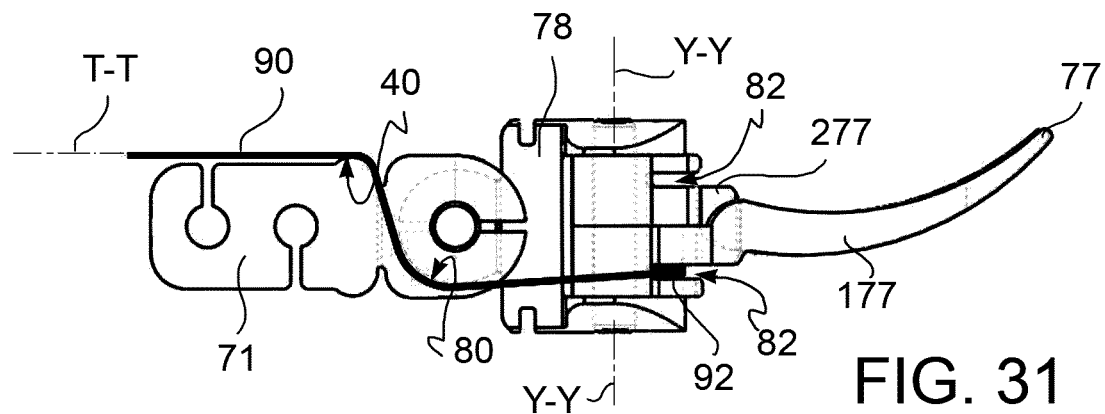
Figure 32:
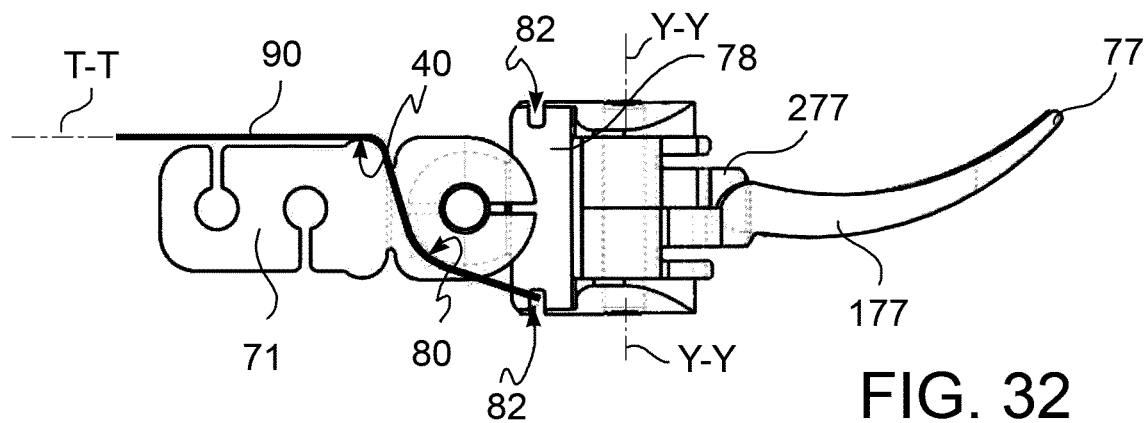
Figure 33:
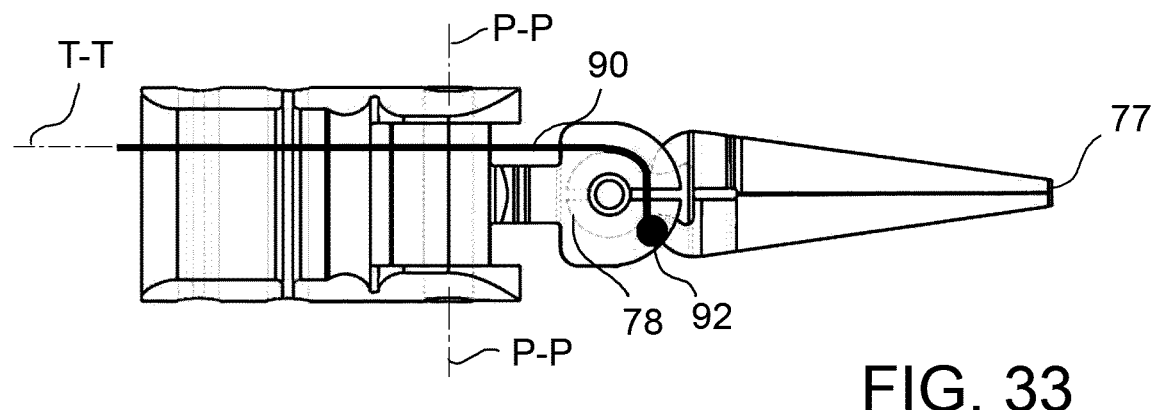
Figure 34:
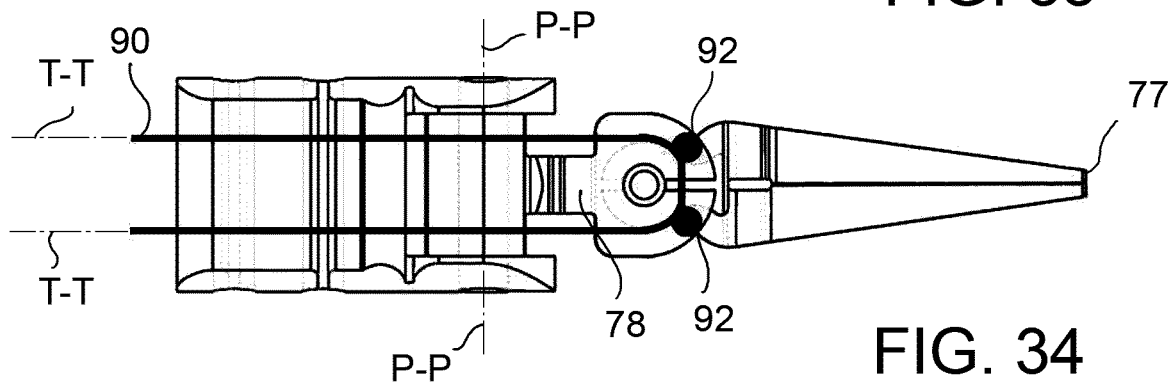
Figure 37:
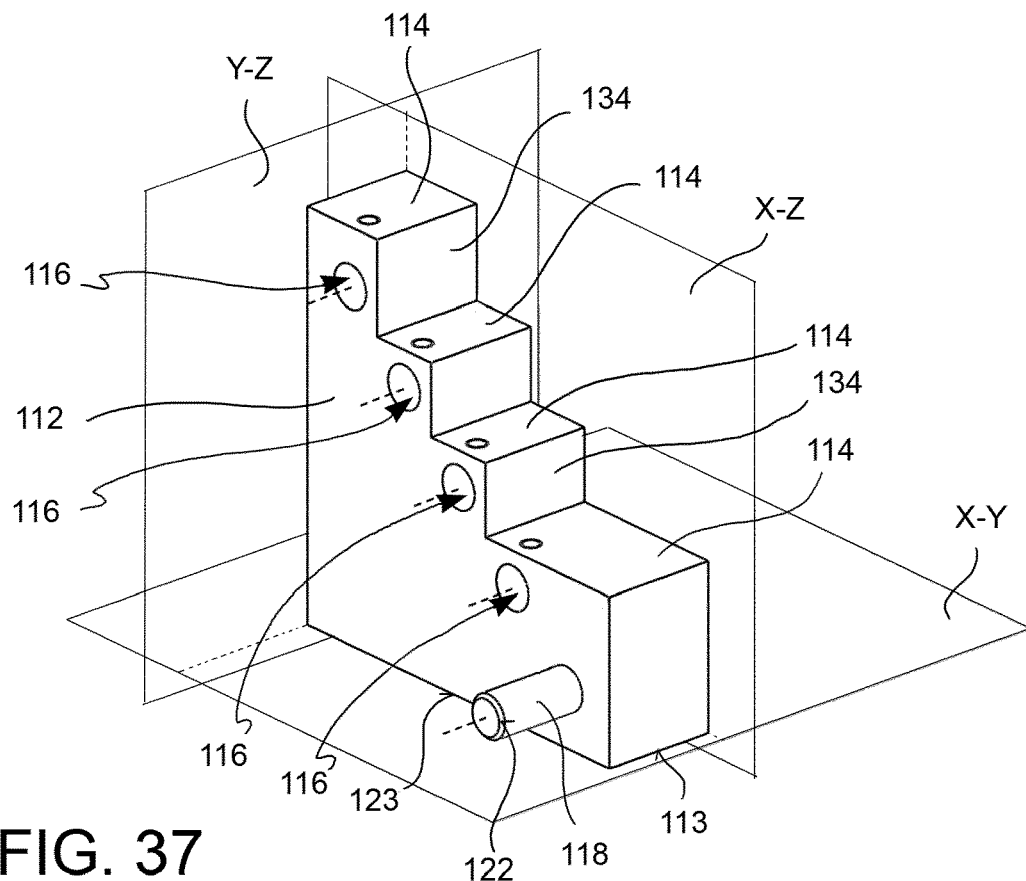
Figure 38:
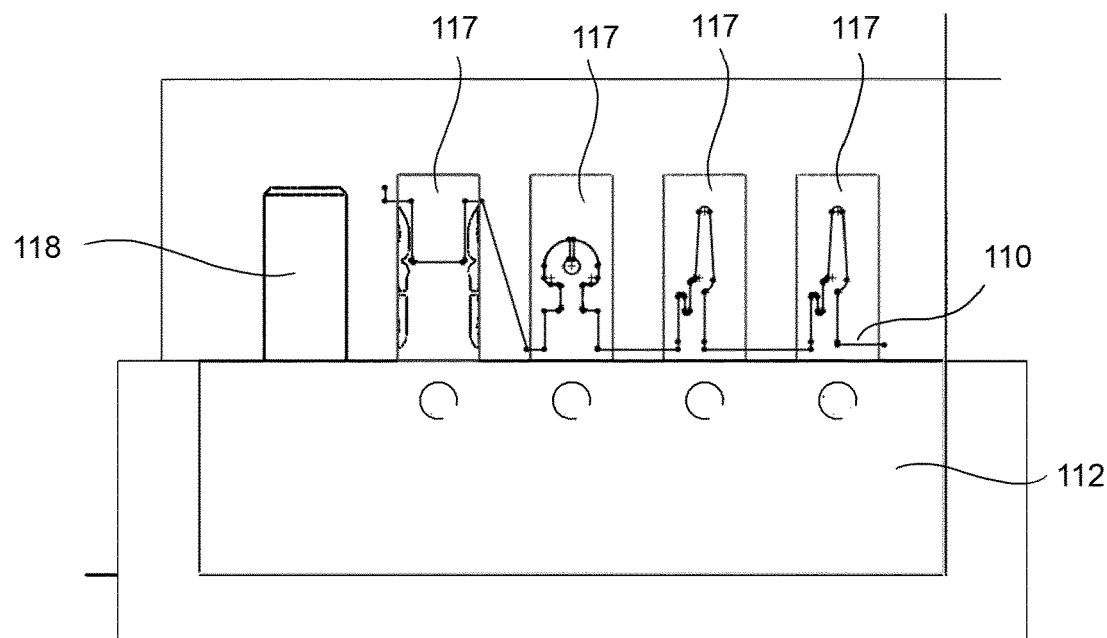
Figure 39:
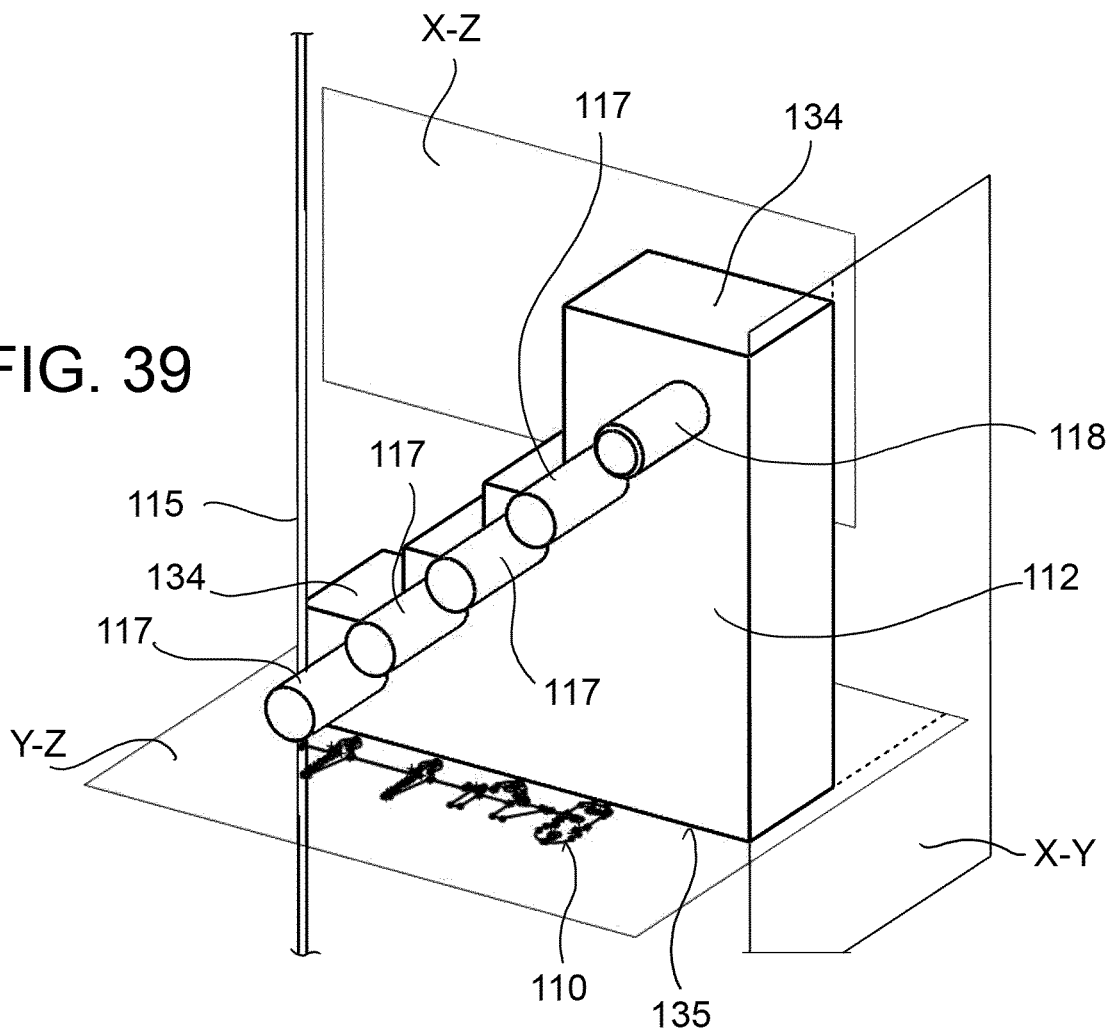
Figure 40:
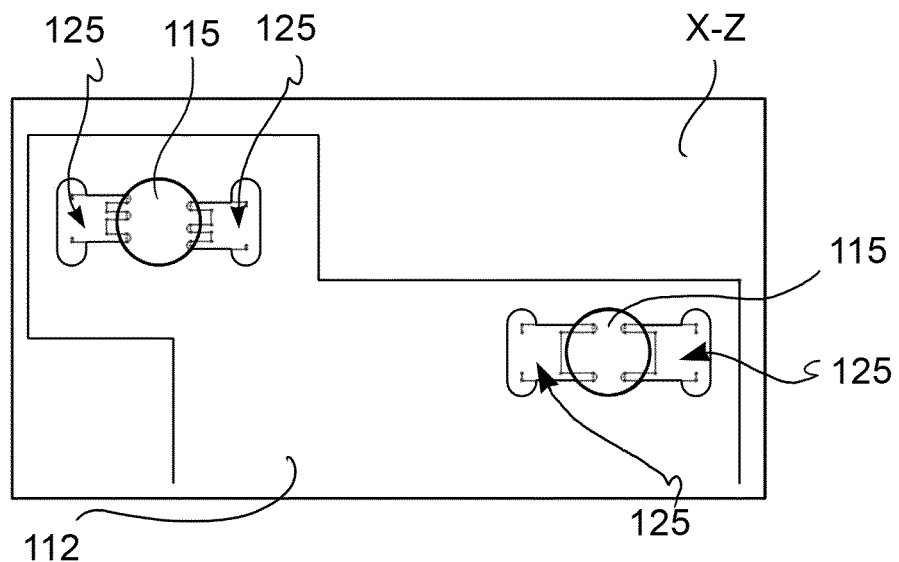
Figure 40B:
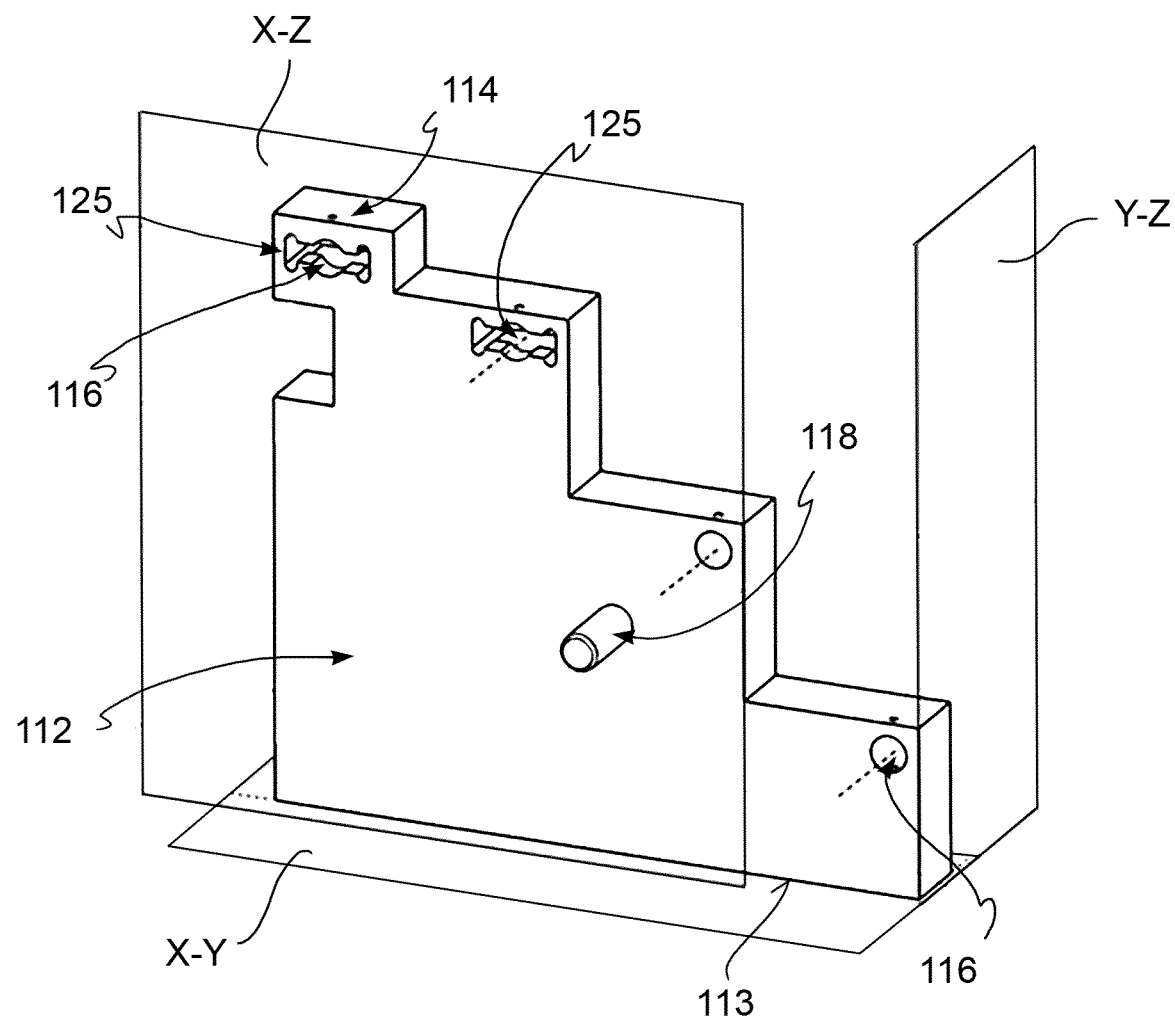
Figure 41:
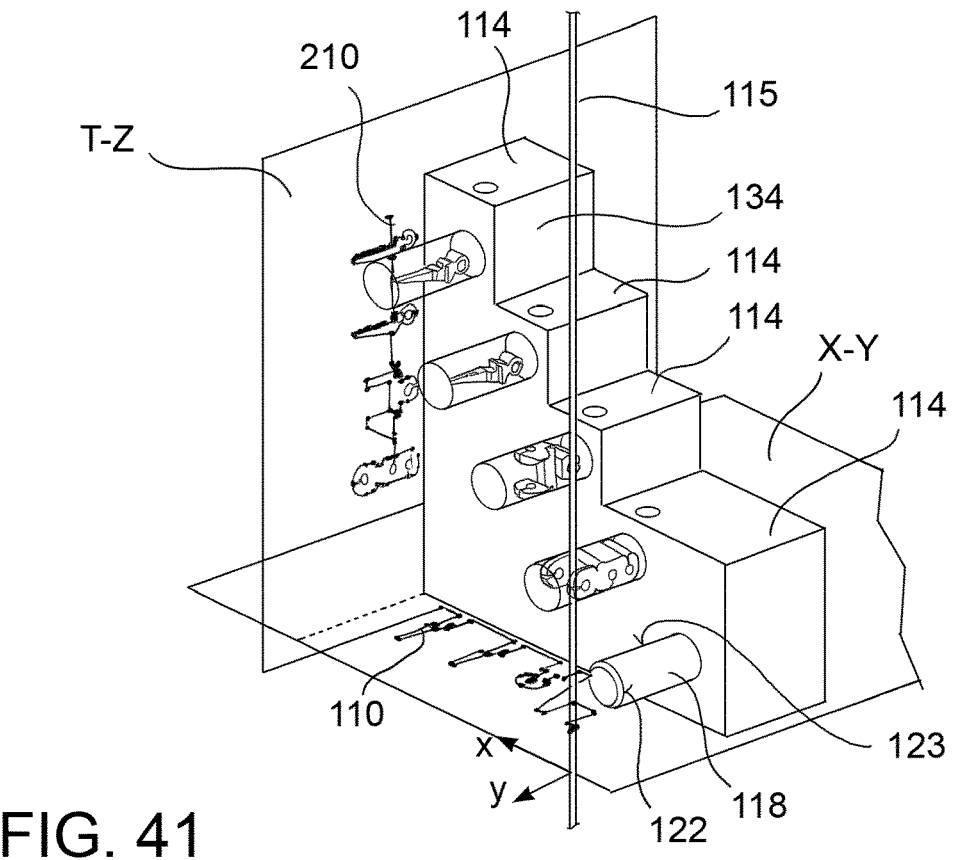
Figure 42:
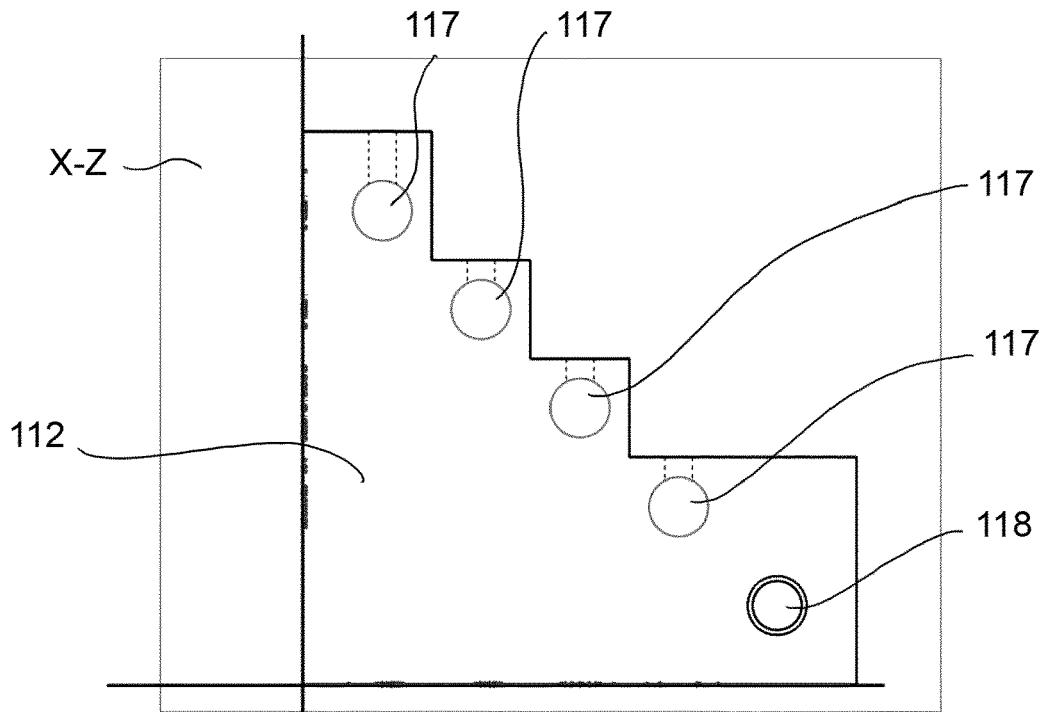

Further characteristics and advantages of the invention will appear from the description reported below of preferred embodiments, which are given as examples and are not meant to be limiting, which makes reference to the attached Figures, in which:

the FIG. 1A is a perspective view, which shows the surgical robotic assembly according to one aspect of the invention;

the FIG. 1B is a perspective view, which shows the surgical robotic assembly according to one aspect of the invention;

the FIG. 1C is a perspective view, which shows a surgical robotic assembly according to one aspect of the invention;

the FIG. 2A is a perspective view, which shows a surgical robotic assembly according to one aspect of the invention associated with other elements of the operating room;

the FIG. 2B is a frontal view, which shows a surgical robotic assembly according to one aspect of the invention associated with other elements of the operating room;

the FIG. 3 is a perspective view, which shows a portions of a couple of jointed or articulated devices according to one aspect of the invention;

the FIG. 4A is a view from above, which shows a portion of a surgical robotic assembly according to one aspect of the invention associated with other elements of the operating room and a patient;

the FIG. 4B is a top view, which shows a portion of a surgical robotic assembly according to one aspect of the invention associated with other elements of the operating room and a patient.

the FIG. 5 is a perspective view, which shows a portion of a surgical robotic assembly according to one aspect of the invention associated with other elements of the operating room and a patient;

the FIG. 6 is a perspective view, which shows a portion of a surgical robotic assembly according to one aspect of the invention associated with other elements of the operating room, the surgeon and a patient;

the FIG. 7 is a perspective view, which shows a control device according to one aspect of the invention;

the FIG. 8 is a perspective view, which shows a macro-positioning arm according to one aspect of the invention;

the FIG. 9A is a perspective view, which shows a portion of a robotic assembly according to one aspect of the invention;

the FIG. 9B is a perspective view, which shows a portion of a robotic assembly according to one aspect of the invention;

the FIG. 9C is a perspective view, which shows a portion of a robotic assembly according to one aspect of the invention, associated with a microscope;

the FIG. 9D is a perspective view, which shows a portion of a robotic assembly according to one aspect of the invention, associated with an endoscope;

the FIG. 9E is an enlarged view of the detail indicated with the arrow E-E of FIG. 9C;

the FIG. 10 is a perspective view, which shows a portion of a robotic assembly according to one aspect of the invention;

the FIG. 11 is a perspective view, which shows a medical instrument according to an embodiment;

the FIG. 12 is a perspective view, and a depiction of separate parts, which shows a medical instrument according to an embodiment;

the FIGS. 13A and 13B show, in a perspective view, portions of a driving system according to an embodiment;

the FIG. 14A is a schematic section view of a portion of a driving system according to an embodiment;

the FIG. 14B is a schematic section view of a portion of a driving system according to an embodiment;

The FIG. 15A is a perspective view that shows a medical instrument according to an embodiment;

the FIG. 15B is a perspective view that shows a medical instrument according to an embodiment;

the FIG. 15C is a sketch in perspective view that shows a medical instrument according to an embodiment;

the FIG. 15D is a sketch in perspective view that shows a medical instrument according to an embodiment;

the FIG. 16 is a schematic drawing, viewed from top and with partially transparent parts, which shows a tendon path of two tendons according to an embodiment;

the FIG. 17 is a perspective view of an articulated device according to an embodiment;

the FIGS. 18 to 20 are perspective views with isolated parts of some embodiments of an articulated device, according to some embodiments;

the FIG. 21 shows a profile of an articulated device according to an embodiment;

the FIGS. 22 to 24 show several poses of some embodiments of an articulated device according to some embodiments;

the FIGS. 25 to 27 shows several embodiments of a terminal tool according to some embodiments;

the FIG. 28 shows a perspective view of a detail of a tendon according to an embodiment;

the FIG. 29 shows a perspective view of a detail of a tendon according to an embodiment;

the FIG. 30 shows a perspective view of a detail of a tendon according to an embodiment;

the FIGS. 31 to 36 are schematics, which show a path of the tendon according to some embodiments;

the FIG. 37 is a schematic in perspective view, which shows a machining fixture according to an embodiment;

the FIG. 38 is a schematic, which shows the profile of a machining cut according to an embodiment;

the FIG. 39 is a schematic in perspective, which shows a phase of a fabrication method according to an embodiment;

the FIG. 40A is a planar view, which shows a detail of a machining fixture according to an embodiment;

the FIG. 40B is a perspective view, which shows a detail of a machining fixture according to an embodiment;

the FIG. 41 is a schematic in perspective view, which shows a phase of a fabrication method according to an embodiment;

the FIG. 42 is a frontal view of a tool according to an embodiment.

DESCRIPTION OF PREFERRED EMBODIMENTS

According to an embodiment, the term "tendon", or "actuation cable", refers to an element which presents a prevalently longitudinal extension and is suitable to work under tensile loads applied at its endpoints. According to an embodiment, the term "opposite tendon" or "opposite actuation cable" refers to a further tendon suitable to work in an antagonistic way with respect to said tendon. According to an embodiment, in the attached figures, said tendon will generally be indicated by the numeric reference "90" and said opposite tendon will be indicated by the numeric reference increased by one hundred, that is "190". Nonetheless, in figures in which distinguishing between said tendon and said opposite tendon is irrelevant, said tendon and said opposite tendon will both be indicated by the numeric reference 90. According to an embodiment, the concept of "opposite" extends itself to multiple elements and/or parts of elements, such as referred to for said "tendon" above. According to an embodiment, the tendons comprised in a first pair of tendons will be indicated with references "90, 190", and the tendons belonging to a second pair of tendons will be indicated with the references "191, 192".

According to an embodiment, the terms "master-slave", "master" and "slave" refer to the known system of teleoperation.

According to an embodiment, the term "terminal tool" refers to a portion suitable to perform an assigned task, such as for example form the interface with at least on portion of the patient. For example, in a teleoperation system of the master-slave type, said terminal tool, or terminal portion, or terminal member, is at least one portion of an "end-effector".

According to an embodiment, the term "jointed or articulated device" refers to a wrist joint, an elbow joint or a shoulder joint of a robotic or mechatronic structure, in other words, an interconnected assembly of members and articulations suitable to support and/or orient and/or position and/or influence the position of said terminal tool.

According to an embodiment, the members of a jointed or articulated device will be indicated by the progressive annotation "first member", "second member", and so on, to indicate their position within the kinematic chain, in which the "first member" indicates the most proximal member; in other words "first member" indicates the member furthest from the terminal organ. According to an embodiment, the members of the jointed device will be indicated with the terms "wrist member", "elbow member" or "terminal member" to indicate the function exercised by said members. For example, the same member could be simultaneously a "second member" and a "wrist member".

According to an embodiment, the term "work volume", or "work space", or "work field", or "workspace volume" refers to the set of Cartesian poses accessible to the terminal portion of a jointed or articulated device. According to an embodiment, said volume is of a substantially parallelepiped form. According to an embodiment, said work volume is of a substantially cylindrical form.

According to an embodiment, the term "macro-positioning" refers to an initial operation of positioning of at least one portion of the medical instrument from any position to a work position within or adjacent to the operating field; in other words, "macro-positioning" refers to the operation of making the work volume coincide with the operating field.

According to an embodiment, the term "micro-positioning" refers to an operation of positioning at least one portion of a medical instrument in a finer manner than the "macro-positioning". According to an embodiment the micro-positioning takes place in a more limited space, in real time and under the direct control of the control device (master).

According to an embodiment, the prefix "micro-" before a certain object indicates that said object is primarily, but not exclusively, meant to operate on a sub-millimeter scale.

According to an embodiment, the term "rotational joint" refers to a junction between two elements suitable to permit a relative moment of rotation between said two elements around an axis of joint movement.

According to an embodiment, the term "medical instrument" refers to an instrument suitable to be used during at least one phase of a medical surgical and/or cosmetic therapy.

According to an embodiment, the term "surgical instrument" refers to a medical instrument specifically suited to be generally used in at least one phase of a surgical therapy. According to an embodiment, the term "microsurgical instrument" or "surgical micro-instrument" refers to a medical instrument specifically suited to be used in at least one phase of a microsurgical therapy.

According to an embodiment, the term "frame" refers to a portion of a medical instrument primarily suited to have a structural holding function. According to an embodiment, the "frame" can comprise at least one shaft, that is a long rigid or flexible element that presents a primarily longitudinal extension. According to an embodiment, said shaft, for example can be of a hollow and/or tubular form.

According to an embodiment, the term "ruled surface" refers to a surface achieved by the union of multiple straight lines. According to an embodiment, if not otherwise explicitly stated, the term "ruled surface" refers to a surface achieved by the union of multiple straight lines substantially parallel to each other, or in other words, a ruled surface of substantially parallel generatrices.

Below, when reference is made to a device, or an assembly, or a method, for microsurgery, it is meant a device, assembly or method, suitable to be applied in microsurgery, i.e. with the simultaneous use of means of optical enlargement such as loupes or microscopes, but also suitable for applications in other surgical therapies, such as general surgery, laparoscopic surgery or endoscopic surgery.

According to an embodiment, to not burden the text or figures, when reference is made to a "first" or "second" element (for example a "first micro-positioning device" and a "second micro-positioning device"), they will be indicated with the same numeric reference, as long as they are functionally indistinguishable (for example "41" above); sometimes, due to a need for clarity, the numerical reference will be specified incremented by one hundred (for example "141" above and "241"); hence, for example, the numerical reference "41" will indicate both said "first micro-positioning device" and said "second micro-positioning device", as well as a "third" micro-positioning device. While when the specific reference, for example "141", is used, it will refer to the specific element, in this case the "first micro-positioning device".

Analogously, to not burden the text excessively, the numeric reference relating to an "opposite" element will be omitted, if an element is functionally indistinguishable from its opposite.

According to a general embodiment, a robotic surgical assembly 100 comprises a support 104 and one macro-positioning arm 30, connected to said support 104 and having a plurality of degrees of freedom.

Said macro-positioning arm 30 comprises a support member 38.

Said robotic surgical assembly 100 comprises at least two micro-positioning devices 41, 141, 241, 341, so as to comprise at least a first micro-positioning device 141 and at least a second micro-positioning device 241, wherein each of said at least two micro-positioning devices 41, 141, 241, 341 has a plurality of motorized degrees of freedom, connected in cascade to said support member 38 of said macro-positioning arm 30.

According to an embodiment, the wording "motorized degrees of freedom" means the provision of motor-driven actuators which determine the movement along a certain degree of freedom.

According to an embodiment, said micro-positioning devices 41, 141, 241, 341 provide a plurality of translational degrees of freedom.

Said robotic surgical assembly 100 comprises at least two medical instruments 60, 160, 260, 360 comprising a first medical instrument 160 and a second medical instrument 260, each of said at least two medical instruments 60, 160, 260, 360 is connected in cascade to each of said micro-positioning device 41, 141, 241, 341. In this way, a single support member 38 of a macro-positioning arm 30 is connected to at least two medical instruments, by means of at least two micro-positioning devices, and thus it is possible to adjust the orientation of both said two medical instruments 60, 160, 260, 360 by acting on said support member 38 only.

Each of said at least two medical instruments 60, 160, 260, 360 comprises a jointed device 70, 170, 270 having a plurality of motorized degrees of freedom including a plurality of rotational joints. In this way, a single support member 38 supports at least two joined devices 70, 170, 270 having rotational degrees of freedom. For example, this jointed device comprises a surgical wrist.

Each of said at least two medical instruments 60, 160, 260, 360 comprises a shaft 65, suitable for distancing said jointed device 70 from said micro-positioning devices 41, 141, 241, 341 by a predetermined distance in a shaft direction X-X. In this way, it is possible to separate of a predetermined distance said jointed device having rotational degrees of freedom from the micro-positioning devices having motorized degrees of freedom. For example, when a motor compartment is associated to said micro-positioning devices, the thermal influence of said motor compartment is kept relatively far from the jointed devices. This allows also to miniaturize the dimensions of said jointed device.

Advantageously, robotic surgical assembly 100 rigidly couples said shaft direction X-X of the shaft 65 of said first medical instrument 160 and said shaft direction X-X of the shaft 65 of said second medical instrument 260. In this way, it is possible to control the relative orientation of the shaft 65 of said first medical instrument 160 and of the shaft 65 of said second medical instrument 260.

Said first micro-positioning device 141 provides at least three motorized degrees of freedom of translational motion to said shaft 65 of said first medical instrument 160, and said second micro-positioning device 241 provides at least three motorized degrees of freedom of translational motion to said shaft 65 of said second medical instrument 260. In this way, it is possible to adjust the relative position of said at least two shafts 65 while keeping a predefined relative orientation of said at least two shafts 65.

According to an embodiment, the angle between the shaft direction X-X of the shaft 65 of said first medical instrument 160 and the shaft direction X-X of the shaft 65 of said second medical instrument 260 is constant during any motion of any of said plurality of motorized degrees of freedom of said micro-positioning devices 41, 141, 241, 341.

According to an embodiment, said at least two micro-positioning devices 41, 141, 241, 341 are rigidly attached to said support member 38.

According to an embodiment, said first micro-positioning device 41, 141 rigidly blocks the shaft direction X-X of said first medical instrument 160 and said second micro-positioning device 41, 241 rigidly blocks the shaft direction X-X of said first medical instrument 260.

According to an embodiment, said robotic surgical assembly 100 comprises a further micro-positioning device 341 so and a further medical instrument 360, so that said robotic surgical assembly 100 comprises at least three micro-positioning devices 41, 141, 241, 341, at least three medical instruments 60, 160, 260, 360 and at least three jointed device 70, 170, 270, wherein said third medical instrument 360 comprises a shaft 65, suitable for distancing said jointed device 70 from said third micro-positioning device 341 by said predetermined distance in a shaft direction X-X, wherein said third micro-positioning device 341 provides at least three motorized degrees of freedom of translational motion to said shaft 65 of said third medical instrument 360.

According to an embodiment, said macro-positioning arm 30 includes motorized degrees of freedom.

According to an embodiment, the end portions 77 of said first medical instrument 160 and said second medical instrument 260 reach a common workspace volume 7 of a predetermined fixed size, and wherein said macro-positioning arm 30 allows to reposition said common workspace volume 7 in a desired position over the patient anatomy.

According to an embodiment, said robotic surgical assembly 100 is suitable to cooperate with a vision system 103, associated with said robotic surgical assembly 100.

According to an embodiment, said support member 38 comprises a vision system seat suitable to house at least a vision system 103 associated to said robotic surgical assembly 100.

According to an embodiment, the spatial orientation of said vision system seat of said support member 38 is rigidly locked with respect to the spatial orientation of said at least two micro-positioning devices 41, 141, 241, 341.

According to an embodiment, said vision system 103 is removably attached to said support member 38. Alternatively, said vision system 103 is integral with said support member 38.

According to an embodiment, said vision system 103 comprises at least one of: a digital camera, a digital microscope, 3D digital microscope, an endoscope. According to an embodiment, said endoscope is suitable to be used as a microscope.

According to an embodiment, a shaft angle θ is defined as the angle between the shaft direction X-X of the shaft 65 of said first medical instrument 160 and the shaft direction X-X of the shaft 65 of said second medical instrument 260.

According to an embodiment, a surgical robotic assembly 100 comprises:
- at least one micro-positioning device 41, 141, 241, 341 having multiple degrees of freedom at least of translation.
- at least one medical instrument 60, comprising one jointed or articulated device 70 having multiple rotational degrees of freedom.

Said medical instrument 60 is connected in series, to said micro-positioning device 41 such that said articulated device 70 reaches a predefined position in a work volume 7 with its terminal portion 77.

According to an embodiment, said robotic assembly 100 comprises a support 104 and at least one macro-positioning arm 30, connected to said support 104, with respect to which said macro-positioning arm 30 provides multiple degrees of freedom of macro positioning.

According to an embodiment, said micro-positioning device 41, 141, 241 and 341 is connected in cascade, that is in series, to said macro-positioning arm 30.

The provision of a kinematic chain comprising a macro-positioning arm 30 connected in series to at least one micro-positioning device 41 comprising multiple degrees of freedom at least in translation, connected in series with a medical instrument 60, allows to decouple the positioning movements in translation of the terminal portion 77 of said medical instrument 60 within said work volume 7, and the positioning movements in orientation of the terminal portion 77 of said medical instrument 60 within said work volume 7.

According to an embodiment, said micro-positioning device 41 comprises degrees of freedom exclusively of translation.

According to an embodiment, said micro-positioning device 41 is a cartesian kinematic mechanism, suitable to determine translational movements along at least two mutually orthogonal directions. According to an embodiment, said micro-positioning device 41 is a cartesian kinematic mechanism, suitable to determine translational movements along at least three mutually orthogonal directions.

According to an embodiment, said micro-positioning device 41 comprises a X-Y-Z cartesian kinematic mechanism and a further rotational degree of freedom, around a rotational axis which substantially coincides with the longitudinal direction in which the medical instrument develops.

According to an embodiment, said at least one medical instrument 60 comprising one jointed device 70, has multiple degrees of freedom that are exclusively rotational.

According to an embodiment, a robotic surgical assembly 100 comprises a further micro-positioning device 41, such that it comprises at least a first micro-positioning device 141 and a second micro-positioning device 241.

According to an embodiment, said at least two micro-positioning devices 141, 241 are placed parallel to each other. According to an embodiment, said at least two micro-positioning devices are placed side-by-side to move one medical instrument on the right and one medical instrument on the left.

According to an embodiment, a surgical robotic assembly 100 comprises a further medical instrument 60 such as to comprise at least a first medical instrument 160, connected in cascade, or in series, to said first micro-positioning device 141 and at least a second medical instrument 260, connected in cascade, or in series, to said second micro-positioning device 241.

According to an embodiment, said first medical instrument 160 comprises one jointed device 170 and said second medical instrument comprises a second jointed device 270.

According to an embodiment, said first micro-positioning device 141 and said second micro-positioning device 241 are placed in such a way that the respective terminal portions 77 of each jointed device 70 reach respective work volumes 7 which must at least partially overlap.

The provision of work volumes 7 that at least partially overlap permits an operation in context using at least two medical instruments on one single portion of the patient.

According to an embodiment, said at least two medical instruments 160, 260 are placed parallel to each other.

According to an embodiment, said respective work volumes 7 substantially coincide.

According to an embodiment, said macro-positioning arm 30 comprises at least one support member 38, comprising at least one attachment feature 39, suited to hold at least one portion of at least one micro-positioning device 41.

According to an embodiment, said support member 38 is suited to simultaneously carry/receive at least one portion of said first micro-positioning device 141 and at least one portion of said second micro-positioning device 241.

According to an embodiment, said support member 38 comprises at least one other attachment feature 39, such that it comprises at least three attachment features 39, said further attachment feature 39 being suitable to hold at least one portion of a further micro-positioning device 41.

According to an embodiment, said robotic assembly 100 comprises at least three micro-positioning devices 41, 141, 241, 341.

According to an embodiment, said robotic assembly 100 comprises at least three medical instruments 60, 160, 260, 360.

According to an embodiment, said three medical instruments 60, 160, 260, 360 are positioned in cascade, or in series, with a co-respective micro-positioning device 41, 141, 241, 341, of said at least three micro-positioning devices 41, 141, 241, 341.

According to an embodiment, said first micro-positioning device 141, said second micro-positioning device 241 and said third micro-positioning device 341 are located such that the terminal positions 77 of each jointed device 70 reach respective work volumes that are at least partially overlapping.

According to an embodiment, said support member 38 comprises at least three attachment features 39, each suited to hold at least one portion of a micro-positioning device 41.

According to an embodiment, said macro-positioning arm 30 has three degrees of freedom.

According to an embodiment, said macro-positioning arm 30 has five degrees of freedom, and in which said five degrees of freedom are both of rotation as of translation.

According to an embodiment, said five degrees of freedom of said macro-positioning arm 30 are a translational movement which is substantially vertical, three movements which are substantially rotational around said first, second and third axis of movement of the arm a-a, b-b, c-c and at least one rotational movement around said fourth axis of movement of the arm d-d.

According to an embodiment, said axes of movement of the arm can be fixed or mobile with respect to a common reference system.

According to an embodiment, said macro-positioning arm 30 is a passive mechanism. In other words, according to an embodiment, said macro-positioning arm 30 is meant to be manually moved by an operator.

According to an embodiment, said macro-positioning arm 30 has six degrees of freedom, of which at least one of rotation. The provision of this characteristic allows the formation of an active anthropomorphic robot, as shown in a non-limiting example in FIG. 1C. According to an embodiment, said macro-positioning arm 30 is an active anthropomorphic robot. In other words, according to an embodiment, said macro-positioning arm is moved by a motorized system comprising a stepper motor or a servo-motor.

According to an alternative embodiment, said macro-positioning arm 30 is a passive anthropomorphic robot.

According to an embodiment, said macro-positioning arm 30 has a radius of extension of movement of 650 mm.

According to an embodiment, said macro-positioning arm 30 comprises:
  one first arm member 31, connected to said support 104 and mobile with respect to said support 104 along a linear sliding guide 36,
  a second arm member 32, connected to said first arm member 31 around a first axis of movement a-a.

The provision that said first member of the arm 31 is mobile with respect to said support 104 along a linear sliding guide 36, allows for a up and down movement to get closer or further from the operating field.

According to an embodiment, said macro-positioning arm 30 further comprises a third arm member 33 connected to a second arm member 32 and mobile with respect to said second arm member 32 around a second axis of movement of the arm b-b.

According to an embodiment, said macro-positioning arm 30 further comprises a fourth arm member 34 connected to said third arm member 33 and mobile with respect to said third arm member 33 around a third axis of movement of the arm c-c.

According to an embodiment, said macro-positioning arm 30 further comprises at least one rotational dial nut 43, which is mobile around a fourth axis of movement of the arm d-d, and is suitable to be manipulated to move said support member 38 around said fourth axis of movement of the arm d-d.

According to an embodiment, said five degrees of freedom of said macro-positioning arm 30 are a translational movement which is substantially vertical, three substantially rotational movements around said first, second and third axis of movement of arm a-a, b-b, c-c and at least one rotational movement around said fourth axis of movement of the arm d-d.

According to an embodiment, said rotational dial nut 43 comprises a click or non-continuous movement mechanism defining pre-established displacements.

According to an embodiment, there is a reduction in the transmission of rotational movement between said rotational dial nut 43 and said support member 38. In other words, big angular movements of said rotational dial nut correspond to small angular movements of said support member 38, in a similar manner to an objective of a camera.

Provisioning said support member 38 to be mobile by a rotational movement around said fourth axis of movement of the arm d-d allows the positioning of said terminal portion 77 of said at least one medical instrument 60, associated to said macro-positioning arm 30, in proximity of a predetermined portion of the patient 201 with a favourable angle between the instrument shaft and the anatomy plane, steeper or shallover to facilitate suturing on different natomical planes.

According to an embodiment, said rotational dial nut 43 comprises at least one milled handle This provides for finer control.

According to an embodiment, said first axis of movement of the arm a-a, said second axis of movement of the arm b-b and said third axis of movement of the arm c-c are substantially parallel to each other.

According to an embodiment, said fourth axis of movement of the arm d-d is substantially orthogonal to said third axis of movement of the arm c-c.

According to an embodiment, a manual knob 37 moving a rack and pinion mechanism controls the movement of said first member of the arm 31 in said linear sliding guide 36 by its rotational movement.

According to an embodiment, said macro-positioning arm 30 comprises at least one braking system, suitable for blocking the relative movement of at least two of said support 104, said first member of the arm 31, said second member of the arm 32, said third member of the arm 33, said fourth member of the arm 34.

According to an embodiment, said braking system comprises at least one electromagnetic brake device.

According to an embodiment, said macro-positioning arm 30 comprises at least one release button 35, or unlocking button, which can be switched between a brake (or lock) and a release (or unlock) position.

According to an embodiment, said braking system can be released by a release button 35.

According to an embodiment, said release button 35 can be switched between a brake position and a release position.

According to an embodiment, said release button 35, when in the release position, allows the operator to move, by carrying it around, at least one of the degrees of freedom of said macro-positioning arm 30.

According to an embodiment, when it is in its release position, said release button 35 is able to release the braking system, allowing the simultaneous relative movement of at least two of said support 104 and said first member of the arm 31, said second member of the arm 32, said third member of the arm 33 and said fourth member of the arm 34.

According to an embodiment, when it is in the release position, said release button 35 is suitable to inactivate said arrest system, allowing the simultaneous relative movement of said first member of the arm 31, said second member of the arm 32, said third member of the arm 33 and said fourth member of the arm 34.

According to an embodiment, said release button 35 is suitable to work by pressure, when it is depressed it is in said release position, and when it is raised or undepressed it is in said arrest position.

According to an embodiment, said robotic assembly 100 comprises:
  said macro-positioning arm 30, passively mobile by releasing said release system,
  said at least one micro-positioning device 41 and said at least one articulated device 70, actively controlled by master slave teleoperation, from the movement of said control instrument 21 as performed by the surgeon 200.

According to an embodiment, said micro-positioning device 41, 141, 241 has three degrees of freedom of translation.

According to an embodiment, said micro-positioning device 41, 141, 241 has four degrees of freedom, of which three are of translation.

According to an embodiment, each micro-positioning device 41 comprises a spherical joint 173, said spherical joint 173 is positioned in cascade, or in series, upstream of each micro-positioning device 41.

According to an embodiment, for example shown in FIG. 2B, each micro-positioning device 41, 141, 241 comprises a spherical joint 173, suitable to change the orientation of the medical instrument 60, 160, 260 by moving the micro-positioning device 41, 141, 241, from its base, i.e. most proximal portion. According to an embodiment, said spherical joint 173 is a universal joint that can be blocked.

According to an embodiment, said micro-positioning device 41 comprises a first motorized slide 51, mobile along a first sliding rail 54 along a first sliding direction f-f.

According to an embodiment, said micro-positioning device 41 comprises a second motorized slide 52, mobile along a second sliding rail 55 along a second sliding direction g-g.

According to an embodiment, said micro-positioning device 41 comprises a third motorized slide 53, mobile along a third sliding rail 56 along a third sliding direction h-h.

According to an embodiment, said first sliding direction f-f is substantially rectilinear.

According to an embodiment, said second sliding direction g-g is substantially rectilinear.

According to an embodiment, said second sliding direction g-g is substantially orthogonal with respect to said first sliding direction f-f.

According to an embodiment, said third sliding direction h-h is substantially rectilinear.

According to an embodiment, said third sliding direction h-h is substantially orthogonal with respect to both said first sliding direction f-f and said second sliding direction g-g.

According to an embodiment, the third sliding direction h-h is aligned with the shaft 65.

According to an embodiment, said micro-positioning device 41 is suitable for working with a stepper motor or a servo-motor. According to an embodiment, said micro-positioning device 41 is suitable to work with a piezoelectric motor or an ultrasonic motor.

According to an embodiment, at least one motorized slide 51, 52, 53 of said first, second and third motorized slides, is connected to a motor via a transmission mechanism comprising a ball screw which rotates with respect to the respective slide rail 54, 55, 56 and is held by a nut.

According to an embodiment, said nut is solidal to at least one motorized slide 51, 52, 53 of said first, second and third motorized slides.

The provision of a transmission mechanism comprising a coupling of a preloaded ball or lead screw-nut type confers an improved control of movement to the motorized slide as well as decreased backlash.

According to an embodiment, at least one motorized slide 51, 52, 53 of said first, second, third motorized slides, is connected to a motor by a transmission mechanism comprising a cogged belt.

According to an embodiment, said motorized slides 51, 52, 53 are precision micro-slides having a stroke between 1 cm and 10 cm, and having precision in the 0.1 micron and 25 micron range.

According to an embodiment, said motor is a servo-motor. According to an embodiment, said motor is a stepper motor.

According to an embodiment, said medical instrument 60 comprises a motorized rotary joint 46, suitable for moving said medical instrument 60 around a longitudinal axis of rotation r-r.

According to an embodiment, said micro-positioning device 41 also comprises a motorized rotary joint 46, suitable for moving said medical instrument 60 around a longitudinal axis of rotation r-r.

According to an embodiment, said axis of longitudinal rotation r-r substantially coincides with its longitudinal axis of development, or axis of the instrument X-X, or longitudinal axis of the shaft X-X, of said medical instrument 60.

According to an embodiment, said medical instrument 60 comprises one articulated device 70 with two degrees of freedom of rotation. According to an embodiment, said medical instrument 60 comprises one articulated device 70 with two degrees of freedom of rotation orthogonal to each other to form a jointed wrist.

According to an embodiment, said medical instrument 60 comprises a jointed device 70 with at least three degrees of freedom. According to an embodiment, said jointed device 70 has three degrees of freedom of rotation, of which two degrees of freedom of rotation around axes parallel to each other and a third degree of freedom of rotation around said longitudinal axis of rotation r-r.

According to an embodiment, said jointed device 70 has three degrees of freedom of rotation, of which one first degree of freedom of rotation, around a first axis of rotation orthogonal to the axis of the instrument X-X, one second degree of freedom of rotation parallel to the first axis of rotation and a third degree of freedom of rotation orthogonal to the second axis of rotation, such that said second and third degrees of freedom of rotation are close to each other and form a sub-articulation of the wrist.

According to an embodiment, said medical instrument 60 comprises a jointed device 70, which has a further degree of freedom in its terminal portion 77, said further degree of freedom allows an opening and/or closing movement of said terminal portion 77. According to an embodiment, said jointed device 70 comprises a terminal device 77 in said distal portion, in which said terminal device 77 comprises said further degree of freedom of opening and/or closing. For example, said further degree of freedom determines the opening and/or closing of forceps or of a cutting instrument, such as scissors.

According to an embodiment, said at least one medical instrument 60 is connected in a detachable fashion to said robotic assembly 100.

According to an embodiment, said medical instrument 60 comprises at least a shaft 65, suitable to connect said frame 57 with said jointed device 70.

According to an embodiment, said medical instrument 60 comprises at least one shaft 65 such as to position its jointed device 70 at a predefined distance from said micro-positioning device 41. According to an embodiment, said shaft 65 is suitable for distancing said jointed device 70 from said micro-positioning device 41 by a predefined distance.

According to an embodiment, said predefined distance is a multiple of the longitudinal extension of said jointed device 70. According to an embodiment, said predefined distance is equal to at least five times the longitudinal extension of said jointed device 70. According to an embodiment, said predefined distance is equal to substantially twenty times the longitudinal extension of said jointed device 70. According to an embodiment said predefined distance is measured along the longitudinal direction of the shaft X-X. According to an embodiment, said predefined distance is equal to substantially fifty times the longitudinal extension of said jointed device 70.

The provision of said shaft 65 which distances said micro-positioning device 41 and said jointed device 70 allows for the fabrication of said micro-positioning device 41, as well as said jointed device 70 to be of dimensions that are appropriate for them to fulfill their functions when in operating conditions. When said robotic assembly 100 comprises a plurality of medical instruments 60, 160, 260, 360, the provision of said shaft 65 in each medical instrument 60, 160, 260, 360 which distances the respective micro-positioning devices 41, 141, 241, 341 from the associated jointed devices, allows for the terminal portions 77 of each medical device to reach their own work volumes, while keeping their ability to move independently.

According to an embodiment, said shaft 65 is suitable to connect to said frame with said terminal device 77 at a predefined distance from said frame 57.

According to an embodiment, said shaft 65 is rigid.

According to an embodiment, said shaft 65 has a longitudinal extension between 30 mm and 250 mm, and preferably between 60 mm and 150 mm.

According to an embodiment, said shaft 65 has a longitudinal internal hole. According to an embodiment, said shaft 65 has a hollow tubular form.

According to an embodiment, said medical instrument 60 comprises a motor box 61 suitable to house at least one driving system of at least said jointed device 70, of said medical instrument 60. In this way, the actuation of said jointed device 70 happens internally to said medical instrument 60.

According to an embodiment, a robotic assembly 100 comprises at least one control device 20, suitable to determine the movement of at least one portion of said medical instrument 60, 160, 260, by a master-slave type communication system.

According to an embodiment, said assembly comprises a further control device 20, such that it comprises at least two input devices 20. According to an embodiment, said control device 20 is suitable to determine the motion of said jointed device 70 of said medical instrument 60.

According to an embodiment, said control device 20 is suitable to determine the movement of said micro-positioning device 41. The provision of said characteristic allows a translational movement of said control instrument 21 as registered by said detection device 22 to be associated to a translational movement of said terminal device 77 within its workspace 7, 17.

According to an embodiment, said control device 20 is suitable to determine the motion of said micro-positioning device 41 and said medical instrument 60.

The provision of this characteristic allows to move at least a portion of said micro-positioning device 41 and at least a portion of said medical instrument 60 by means of said control instrument 21, such as to determine both rotational and translational movements of said terminal device 77 in said work volume 7.

According to one alternative embodiment, said micro-positioning device 41 comprises a plurality of passive degrees of freedom that can be braked or otherwise blocked. According to an embodiment, said plurality of degrees of freedom is placed immediately upstream and in series to said micro-positioning device 41.

According to an embodiment, said robotic assembly 100 is suitable to cooperate with a vision system 103 associable to said robotic assembly 100.

According to an embodiment, said vision system 103 is a microscope 103.

The provision of a microscope 103 associable to said robotic assembly allows for retro-fitting with pre-existing microscopes, making said robotic assembly 100 more versatile. For example, said robotic assembly 100 can be used in cooperation with microscopes that have a focusing distance between 100 mm and 500 mm, depending on the focal length of the objective lens used. Furthermore, it allows the swept volume of the robotic assembly 100 to be reduced, during the surgical operation given that it lacks as many parts as possible that require relatively large movements during the movement of the terminal portion of the instrument.

According to an embodiment, said microscope 103 is an optical microscope 103.

According to an embodiment, said microscope 103 is suitable to frame in its field of view said terminal portion 77 of said first medical instrument 160 and/or said terminal portion 77 of said second medical instrument 260 and/or said terminal portion of said third medical instrument 360.

According to an embodiment, said microscope 103 is suitable for framing the work volume 7.

According to an embodiment, at least one video-camera 45, is connected to said support member 38.

According to an embodiment, said video-camera 45 is suitable for framing said terminal portion 77 of said first medical instrument 160 and said terminal portion 77 of said second medical instrument 260.

According to an embodiment, said support 104 comprises at least one display 111, suitable to form a machine input interface.

According to an embodiment, said display 111 is suitable to visualize the images acquired by said video-camera 45.

According to an embodiment, said video-camera 45 is suitable to cooperate with said macro-positioning arm 30 to permit the correct positioning of said at least one medical instrument 60. The provision of this characteristic facilitates the positioning process of at least one portion of said at least one medical instrument 60 within the work volume 7.

According to an embodiment, said first medical instrument 160, said second medical instrument 260 and said support member 38 are disposed in such a way that they substantially form a triangle. Such provision allows to reproduce of the same triangulation existing between the eyes and the arms of the surgeon by means of said robotic assembly 100.

According to an embodiment, said support 104 is at least one of: a mobile cart, a support structure of a microscope, an operating bed, an operating table.

According to one aspect of the invention, a control device 20 for microsurgery for a robotic assembly for microsurgery 100, in which said control device 20 is suitable to at least partially form the master interface of a master-slave pair for a robotic assembly for microsurgery 100, comprises:

at least one control instrument 21, mobile in space, of a shape and size which lends it to being held and handled like a traditional surgical instrument, that is to say a surgical instrument suitable to operate directly on at least one portion of the patient anatomy 201, at least one detection device 22, suitable to detect the position of said control instrument 21 in at least on portion of space.

Said control instrument 21 comprises at least one position sensor 28, which cooperates with said detection device 22, to sense at least the position of said control instrument 21.

According to an embodiment, said detection device 22 generates an electromagnetic field such as to detect at least the position of said control instrument 21 by detecting the position of said at least one position sensor 28. According to an embodiment, said detection device 22 detects at least the position of said control instrument 21 by detecting the position of said position sensor 28 by measuring at least inertial accelerations components. According to an embodiment, said position sensor 28 comprises accelerometers.

According to an embodiment, said detection device 22 is positioned in a base structure 67 of said control device 20.

According to an embodiment, said control instrument 21 is connected to said detection device 22 by at least an electromagnetic communication system.

According to an embodiment, said control instrument 21 comprises at least one forceps articulation 69, effective in a tip portion 68 of said control instrument 21, such as to allow said tip portion 68 a grasping or cutting movement.

According to an embodiment, at least one tip sensor 29 measures an opening angle of said forceps articulation 69.

According to an embodiment, said control instrument 21 has a shape that substantially replicates the shape of a traditional surgical instrument.

According to an embodiment, said control instrument 21 has the shape of surgical forceps.

According to an embodiment, said control instrument 21 has the shape of a surgical scalpel.

According to an embodiment, said control instrument 21 has the shape of a surgical needle holder.

According to an embodiment, said control instrument 21 has the shape of surgical scissors.

According to an embodiment, said control instrument 21 has the shape of a surgical blade.

According to an embodiment, said control device 20 comprises at least one ergonomic support element for the operator 27, comprising at least one support surface for the operator 25, suitable to support at least one portion of the forearm of the micro-surgeon 200, at least when in operating conditions, such as to provide ergonomic support for the micro-surgeon 200. The provision of such a characteristic allows for improved comfort of the micro-surgeon, determining an improved operating efficiency.

According to an embodiment, said ergonomic support element 27 comprises at least one portion made of soft material or foam.

According to an embodiment, said control instrument 21 is connected to said detection device 22 by at least one system of electromagnetic communication. According to an embodiment, said position sensor is an electromagnetic position sensor with micro-bobbins and said sensor device comprises a generator of a magnetic field and an electric circuit that reads the circuit induced in said micro-bobbins by said magnetic field. The provision of this characteristic allows the control instrument 21 to preserve its functioning as a traditional surgical instrument, without affecting a response time for said detection device 22.

According to an embodiment, said control instrument 21 is connected to said detection device 22 by a wired connection, or cable.

According to an embodiment, said control instrument 21 is connected to said detection device 22 by a wireless connection.

According to an embodiment, said detection device 22 is suitable to measure the position in space, this position measure being either by induced current, or it is an optic measure, or an ultrasound measure, or a measure by ionizing radiation.

According to an embodiment, said control device 20 comprises an on-off type switch, either implemented as a pedal or as a button, selectively suitable to activate or disactivate input from said control device 20.

According to an embodiment, a robotic assembly 100, comprises:
at least one control device 20, as described by one of the embodiments described above,
at least one surgical micro-instrument 60, 160, 260, 360 comprising at least one terminal portion 77.

According to an embodiment, said terminal portion 77 is suitable to operate on at least one portion of the patient 201.

According to an embodiment, said terminal portion 77 is suitable to handle a surgical needle 202, as shown for example in FIG. 3A-3B.

According to an embodiment, said control instrument 21 has the same dimensions and offers the same handling experience of a traditional surgical instrument, that is to say a surgical instrument that can be used to operate directly on at least one portion of a patient 201, and said surgical micro-instrument 60 is suitable to replicate the same entire movement capability of said control instrument 21.

According to an embodiment, said robotic assembly 100 is suitable to decouple the movements of said control instrument 21 and said surgical micro-instrument 60 in such a way that when the movements of said control instrument 21 are large and comprise vibrations, while the movements of said surgical micro-instrument 60 are filtered of vibrations and reduce the movement to a millimeter or to a micron scale. The provision of scaled movement introduced between the master interface and the slave interface allows for the reduction of tremor as well as an improvement of precision of said surgical micro-instrument without decreasing the ease of operation of the surgeon 200.

According to an embodiment, said control instrument 21 is suitable to cooperate with said surgical micro-instrument 60 in such a way that, when in operating conditions, at a first 3D movement of said control instrument 21 with respect to said detection device, corresponds to a second 3D movement of said surgical micro-instrument 60.

According to an embodiment, said control instrument 21 is suitable to cooperate with said surgical micro-instrument 60, 160, 260, in such a way that, when in operating conditions, a first translational movement of said control instrument 21 corresponds to a second translational movement of said surgical micro-instrument 60, 160, 260 equal to a fraction of the amplitude of said first movement of said control instrument 21. In this way, it is possible to limit the transmission of tremor or vibration of the control instrument 21 to the surgical micro-instrument 60.

According to an embodiment, said control instrument 21 is suitable to cooperate with said surgical micro-instrument 60, 160, 260 in such a way that, when in operating conditions, a first translational movement of said control instrument 21 corresponds to a second translational movement of said surgical micro-instrument 60, 160, 260 of an amplitude that is substantially equal to one tenth of the amplitude of said first movement of said control instrument 21.

According to an embodiment, said control instrument 21 is suitable to cooperate with said surgical micro-instrument 60, 160, 260 such that, when in operating conditions, a first translational movement of said control instrument 21 corresponds to a second translational movement of said surgical microinstrument 60, 160, 260 of an amplitude substantially equal to one thirtieth of the amplitude of said first movement of said control instrument 21.

According to an embodiment, said control instrument 21 is suitable to cooperate with said surgical micro-instrument 60, 160, 260 in such a way that, when in operating conditions, a first angular movement of said control instrument 21 corresponds to a second angular movement of said surgical micro-instrument 60, 160, 260, said second angular movement of the micro-instrument being of an amplitude that is substantially equal to the amplitude of said first movement of the control instrument 21. The provision of such a characteristic renders the use of said control instrument 21 familiar to a surgeon 200.

According to an embodiment, said control instrument 21 is suitable to cooperate with said surgical micro-instrument 60, such that, when in operating conditions, a first angular movement of said forceps articulation 69 of said control instrument 21 corresponds to a second angular movement of an articulation, situated on said terminal portion 77 of said surgical micro-instrument 60, the amplitude of said second movement being substantially equal to said first angular movement of said forceps articulation of said control instrument 21.

According to an embodiment, said a portion of control instrument 21 is of a shape that substantially reproduces the shape of said terminal portion 77 of said surgical microinstrument 60, 160, 260.

According to an embodiment, said surgical micro-instrument 60, 160, 260 comprises at least one jointed device 70 and said control instrument 21 is suitable to cooperate with said jointed device 70, 170, 270 so that, when in operating conditions, a first movement of said control instrument 21 with respect to said detection device 22, corresponds to a second movement of said jointed device 70, 170, 270.

According to an embodiment, a robotic assembly 100 also comprises
a support 104,
at least one macro-positioning arm 30, connected to said support 104, said macro-positioning arm having a plurality of degrees of freedom,
at least one micro-positioning device 41, 141, 241 having a plurality of degrees of freedom of translation.

According to an embodiment, said at least one control device 20 is connected to at least one portion of said microsurgical robotic assembly 100.

According to an embodiment, said at least one control device 20 is freely positionable with respect to said support 104.

According to an embodiment, said surgical micro-instrument 60, 160, 260 comprises at least one micro-instrument sensor, suitable to cooperate with said detection device 22, such that the position in space of at least one portion of the surgical micro-instrument 60, 160, 260 can be detected with respect to said detection device 22.

According to an embodiment, said micro-positioning device 41, 141, 241 comprises at least one micro-manipulator sensor, suitable to cooperate with a detection device 22, such as to detect the position in space of at least one portion of said micro-positioning device 41, 141, 241 with respect to said detection device 22.

According to an embodiment, said macro-positioning arm 30 comprises at least one macro-positioning arm sensor, suitable to cooperate with said detection device 22, such as to detect the position in space of at least one portion of said macro-positioning arm 30 with respect to said detection device 22.

According to an embodiment, said microsurgical robotic assembly 100 is suitable to cooperate with a sensor, suitable to detect the position in space with respect to a single reference system of at least one of: said position sensor 28, said tip sensor 29, said macro-positioning arm sensor, said micro-positioning device sensor, said micro-instrument sensor. According to an embodiment, said microsurgical robotic assembly 100 is suitable to cooperate with a sensor, suitable to detect the position in space with respect to a single reference system of at least two of: said position sensor 28, said tip sensor 29, said macro-positioning arm sensor, said micro-positioning device sensor, said micro-instrument sensor. The provision of this characteristic allows for a teleoperation master-slave system to function adequately independently of the exact position of said detection device 22, said support 104, said macro-positioning arm 30 and said micro-positioning device 41. In other words, said medical instrument 60 is able to follow the movement of control instrument 21 with respect to a same common reference system of coordinates.

According to an embodiment, said at least one surgical micro-instrument 60, 160, 260 is connected to said robotic assembly 100 in a detachable fashion.

According to an embodiment, a microsurgical robotic assembly 100 also comprises:
- a further control instrument 21, such as to comprise a first control instrument 121 and a second control instrument 221;
- a further surgical micro-instrument 60, 160, 260 such as to comprise a first surgical micro-instrument 160 and a second surgical micro-instrument 260.

According to an embodiment, said first control instrument 121 is suitable to cooperate with said first surgical micro-instrument 160, in such a way that, when in operating condition, a first movement of said first control instrument 121 with respect to said detection device 22, corresponds to a second movement of said first surgical microinstrument 160.

According to an embodiment, said second control instrument 221 is suitable to cooperate with said second surgical micro-instrument 260, such that, when in operating conditions, a first movement of said second control instrument 221 with respect to said detection device 22, corresponds to a second movement of said surgical micro-instrument 260.

According to an embodiment, said first control instrument 121 is suitable to form the master interface of said robotic assembly 100 for one first hand of the surgeon 200.

According to an embodiment, said second control instrument 221 is suitable to for the master interface of said robotic assembly 100 for one second hand of the surgeon 200, different from said first hand.

According to an embodiment, said first and second control instruments 121, 221 are of substantially mirrored in shapes and location, such as to form the master interface of said robotic assembly 100 for both hands of the surgeon. In this way, the interface has improved ergonomics and is more familiar to the surgeon.

According to an embodiment, said control device 20 comprises at least two control instruments 21, 121, 221.

According to an embodiment, said microsurgical robotic assembly 100 comprises a further detection device 22 such as to comprise at least two detection devices.

According to an embodiment, said control device 20 comprises at least two detection devices 22.

According to an embodiment, said microsurgical robotic assembly 100 comprises at least one further control device 20, such as to comprise a first control device 120 and a second control device 220.

According to an embodiment, said first control device 120 is suitable to form the master interface of said robotic assembly 100 for the first hand of the surgeon 200.

According to an embodiment, said second control device 220 is suitable to form the master interface of said robotic assembly 100 for the second hand of the surgeon 200, different from said first hand.

According to an embodiment, said first and second control devices 120, 220 are of substantially mirrored shapes, such as to form the master interface of said robotic assembly 100 for both hands of the surgeon. In this way, the interface has improved ergonomics and is more familiar to the surgeon.

According to an embodiment, a medical instrument 60, 160, 260, 360 comprises at least one frame 57 and one jointed device 70.

Said jointed device 70 comprises at least one first joint member 71, or first link 71, suitable to connect to at least one portion of said frame 57, and at least a second joint member 72, or second link 72.

Said first link 71 is connected via a rotational joint 171 to said second link 72.

Said medical instrument 60 also comprises at least one tendon 90, 190, suitable for moving at least said second link 72 with respect to said first link 71, by pulling it.

At least one of said first link 71, said second link 72 comprises at least a sliding surface 40, 80, 140, 180, suitable to allow the sliding of at least one portion of said tendon 90, 190 over it.

Said sliding surface 40, 80, 140, 180 is a ruled surface 40, 80, 140, 180, specifically a ruled surface formed by a plurality of portions of straight lines all parallel to each other and substantially parallel to a joint axis of movement P-P, Y-Y.

According to an embodiment, said sliding surface 40, 80, 140, 180 is a ruled surface 40, 80, 140, 180, specifically a ruled surface formed by a plurality of portions of straight lines all parallel to each other and substantially parallel to a joint axis of movement P-P, Y-Y of the rotational joint 171 closest to said sliding surface 40, 80, 140, 180. According to an embodiment, the closest rotational joint 171 is defined by measuring along the direction of the tendon path T-T.

According to an embodiment, said axes of joint movement can be fixed or mobile with respect to a base reference system.

According to an embodiment, said at least one second link 72 is a wrist member 78, and said wrist member 78 comprises at least one sliding surface 40, 80, 140, 180, formed by a plurality of portions of straight lines parallel to each other and substantially parallel to a first joint axis of movement.

According to an embodiment, said wrist member 78 comprises at least one jointing portion 172, suitable to form at least one portion of a second rotational joint 171 having a second joint axis of movement, not parallel to said first joint axis of movement.

According to an embodiment, said first joint axis of movement and said second joint axis of movement are substantially orthogonal to each other.

According to an embodiment, said first joint axis of movement is a pitch axis P-P.

According to an embodiment, said second joint axis of joint movement is a yaw axis Y-Y.

According to an embodiment, said medical instrument 60, 160, 260 has at least one terminal member 77.

According to an embodiment, said terminal member 77 is suitable to contact with one portion with a patient 201, when in operating conditions.

According to an embodiment, said terminal member 77 is suitable to handle a surgical needle 202.

According to an embodiment, said terminal member 77 comprises a cutting surface or blade and can act as a scalpel.

According to an embodiment, said terminal member 77 comprises at least one winding surface 86, made of a plurality of portions of straight lines all parallel to each other and substantially parallel to a joint axis of movement. According to an embodiment, said winding surface 86 is suitable to allow at least one portion of said tendon 90, 190 to be wound up around it.

According to an embodiment, said second joint member 72 is a terminal member 77.

According to an embodiment, said jointed device 70, 170, 270 comprises a third joint member 73, suitable to connect to at least said second joint member 72 by a rotational joint 171.

According to an embodiment, said third joint member 73 is a terminal member 77.

According to an embodiment, said terminal member 77 is connected to said wrist member 78 by a rotational joint 171.

According to an embodiment, said at least one joint member 72 is an elbow member 75, and said elbow member 75 comprises a plurality of sliding surfaces 40, 80, 140, 180 formed by a plurality of portions of straight lines all parallel to each other and substantially parallel to a single joint axis of movement.

According to an embodiment, said elbow member 75 comprises at least one jointing portion 172, suitable to form at least one portion of a rotational joint 171.

According to an embodiment, said jointed device 70 comprises a third joint member 73, suitable to be connected to at least said second joint member 72 by a rotational joint 171, in which said second joint member 72 is an elbow member 75 and said third joint member 73 is a wrist member 78.

According to an embodiment, said elbow member 75 is connected by a rotational joint 171 to said first joint member 71, and in which said wrist member 78 is connected via a rotational joint 171 to said elbow joint member 75.

According to an embodiment, said jointed device 70 comprises a fourth joint member 74, suitable to connect to at least said third joint member 73 via a rotational joint 171.

According to an embodiment, said fourth joint member 74 is a terminal member 77.gmp According to an embodiment, said terminal member 77 comprises at least one winding surface 86, formed by a plurality of portions of straight lines all parallel to each other and substantially parallel to a joint axis of movement, wherein said winding surface 86 is suitable to allow the winding of at least one portion of said tendon 90, 190 around it.

According to an embodiment, said jointed device 70 comprises said first member 71, connected to said wrist member 78 via a rotational joint 171, connected to said terminal member 77 via a rotational joint 171.

According to an embodiment, said jointed device 70 comprises said first member 71, connected to said elbow member 75 by a rotational joint 171, connected to said wrist member 78 by a rotation joint 171, itself connected to said terminal member 77 by a rotational joint 171. It should be apparent to those skilled in the art that making use of joint members similar to 71, 72, 73, a jointed device 70 can be assembled to include a serial sequence of members, of which from zero to a plurality of elbow joint members 75, a plurality of, preferably orthogonal, pairs of wrist joint members 78 and at least one terminal joint member 77.

According to an embodiment, said winding surface 86 is a ruled surface.

According to an embodiment, said winding surface is substantially unsuitable for said tendon 90, 190 to slide over it. This is because said tendon 90, 190 terminates close to said winding surface 86, on the joint member which comprises said winding surface 86.

According to an embodiment, said medical instrument 60 comprises at least one pair of tendons comprising one tendon 90 and one opposite tendon 190, and said tendon 90 and said opposite tendon 190 are suitable to connect their second termination endpoints 92, or second tendon termination 92, to respective tendon fastening points 82, or point of tendon termination 82, of said second joint member 72, such as to move said second joint member 72 around its joint axis in opposite directions.

According to an embodiment, said medical instrument 60 which comprises at least one pair of tendons comprising one tendon 90 and one opposite tendon 190, and said tendon 90 and said opposite tendon 190 are suitable to connect in their second termination endpoints 92 to respective tendon fastening points 82, or tendon termination features 82, of said terminal member 77, such as to move it around its jont axis in opposite directions.

The provision of such a feature makes sure that said tendon 90 and said opposite tendon 190 can work in an antagonistic fashion, for example both said tendon 90 and said opposite tendon 190 move said terminal member around the yaw axis Y-Y. Hence no passive or free joint movement can occur, and instead there are only positively guided and controlled movements.

According to an embodiment, said tendon 90 and opposite tendon 190 are suitable to connect by means of their second termination endpoints 92 to respective tendon fastening points 82, or tendon termination features 82, of at least one of said first, second, third and fourth joint members 71, 72, 73, 74.

According to an embodiment, said tendon 90 and opposite tendon 190 are suitable to connect by means of their second termination endpoints 92 in respective tendon fastening points 82, or tendon termination feature 82, of at least one of said elbow member 75, wrist member 78 and terminal member 77.

According to an embodiment, said medical instrument 60 comprises at least one shaft 65, suitable to guide said at least one tendon 90, 190. Said shaft 65 is a shaft according to one of any of the previously described embodiments.

According to an embodiment, said shaft 65 has a substantially circular section and has a diameter smaller than 4 millimeters. This allows extreme miniaturization of the medical instrument.

According to an embodiment, said shaft 65 comprises a longitudinal hole such as to allow the passage of said at least one tendon 90, 190 inside it.

According to an embodiment, said shaft 65 is integral to said frame 57.

According to an embodiment, said jointed device 70 has a longitudinal extension smaller than 10 millimeters.

According to an embodiment, said jointed device 70 has a volume inferior to 10 cubic millimeters.

According to an embodiment, said terminal member 77 comprises at least one first portion of terminal member 177 and at least a second portion of terminal member 277.

According to an embodiment, said first portion of terminal member 177 and said second portion of terminal member 277, are mobile with respect to each other around a joint axis of movement such as to determine a grasping or cutting movement. According to an embodiment, said joint axis of movement is said yaw axis Y-Y.

According to an embodiment, said medical instrument 60, which comprises at least one pair of tendons, comprises a tendon 90 and an opposite tendon 190, in which one of said tendon 90 and said opposite tendon 190 is suitable to connect by means of its second endpoint 92 to a respective tendon fastening point 82, or tendon termination feature 82, p on said first terminal member 177, and in which the other one of said tendon 90 and said opposite tendon 190 is suitable to connect by means of its second endpoint 92 to a respective tendon fastening point 82, or tendon termination feature 82, on said second terminal member 277, such as to move said first portion of terminal member 177 and said second portion of terminal member 277 with movements in opposite directions.

According to an embodiment, each of said first portion of terminal member 177 and said second portion of terminal member 277 comprise at least one winding surface 86.

According to an embodiment, said medical instrument 60 comprises at least one pair of tendons comprising one tendon 90 and one opposite tendon 190, in which said tendon 90 and said opposite tendon 190 are suitable to connect by means of their second endpoints 92 in respective tendon fastening points 82, or tendon termination feature 82, of said terminal member 77, such as to move said third joint member 73 with respect to said fourth joint member 74 such as to determine a grasping or cutting movement.

According to an embodiment, said tendon 90 and said opposite tendon 190 wind their distal portions around at least one portion of said at least one winding surface 86 of terminal member 77.

According to an embodiment, said sliding surface 40, 80, 140, 180 is a lateral sliding surface 40, 140 suitable to extend away from the center volume of said jointed device 70, 170, 270 such as to determine that at least one portion of tendon is deflected away and runs not in contact with said jointed device 70.

According to an embodiment, said lateral sliding surface 40, 140 joins a surface of the member on which it is built, with at least a continuity surface 64, sharing a local tangent plane.

According to an embodiment, said lateral sliding surface 40, 140 forms at least one sharp edge 63 with the member on which it is built.

According to an embodiment, said lateral sliding surface 40, 140 joins a surface of the member on which it is built with a continuity surface 64 on one side and on the other side forms one sharp edge 63 with the member on which it is built.

According to an embodiment, said sliding surface 40, 80, 140, 180 is a joint sliding surface 80, 180 that at least partially surrounds an axis of joint movement. According to an embodiment, said sliding surface 40, 80, 140, 180 is a joint sliding surface 80, 180 that at least partially surrounds at least one of said pitch axis P-P and said yaw axis Y-Y, and in which said joint sliding surface 80, 180 is oriented opposite with respect to at least one of said pitch axis P-P and said yaw axis Y-Y, such as to allow at least one intersection between the tendon path T-T of said tendon 90 and the tendon path T-T of said opposite tendon 190. In other words, said joint sliding surface 80, 180 is not suitable to face towards said joint axis of movement of the closest rotational joint 171, when in operating conditions.

According to an embodiment, said joint sliding surface is convex and partially surrounds at least one of said pitch axis P-P or yaw axis Y-Y, such as to permit at least one intersection of two opposite tendons on itself.

According to an embodiment, the term "closest joint" refers to the rotational joint 141 which is closest in distance to the sliding surface 40, 80, 140, 180 along the tendon path T-T.

According to an embodiment, on said joint sliding surface 80, 180 the tendon path T-T of said tendon 90 and the tendon path T-T of said opposite tendon 190, although they do not intersect, they at least partially overlap in a projection plane orthogonal to the direction of said axis of joint movement of the closest rotational joint 171.

According to an embodiment, on said joint sliding surface 80, 180 the tendon path T-T of said tendon 90 and the tendon path T-T of said opposite tendon 190 are distinct from each other and parallel on a projection plane parallel to the joint axis of movement of the closest rotational joint 171.

According to an embodiment, the tendon path T-T of said tendon 90 overlaps with the tendon path T-T of said opposite tendon 190 at least on a projection plane orthogonal to the direction of said joint axis of movement of the closest joint. According to an embodiment, the tendon path T-T of said tendon 90 is substantially parallel to the tendon path T-T of said opposite tendon 190 on a projection plane parallel to said joint axis of movement of the closest rotational joint.

According to an embodiment, the tendon path T-T of each tendon 90 are substantially parallel to each other, on a projection plane parallel to the said joint axis of movement of the closest rotational joint 171.

According to an embodiment, each tendon path T-T is substantially stationary over the joint member which it contacts. In other words, even when the tendon 90 is sliding, the overall tendon path T-T is substantially always in the same position with respect to the joint member of said medical instrument 60, which it contacts.

Such a feature is uniquely realized by provisioning that said sliding surface 40, 80, 140, 180 of said winding surfaces 86 has a cooperative geometrical relationship with said tendon termination feature 82, which is in turn fittingly positioned on a portion of said medical instrument.

According to an embodiment, said tendon path T-T remains substantially stationary over the joint member which it contacts for both tendon 90 and opposite tendon 190 that determines opposite joint movements.

According to an embodiment, the tendon path T-T of each tendon 90 is substantially stationary in its section over said frame 57, except for said deflectable portion 93. Said deflectable portion 93 is in fact suitable to be deflected by the pusher assembly 94, not unlike a guitar string.

According to an embodiment, said at least one tendon 90, 190, when in operating conditions, follows a tendon path T-T that is entirely composed of successive straight in-flight sections 9, which are not in contact with any sliding surface 40, 80 or winding surfaces 86, and curved sections which are in contact with sliding surfaces 40, 80 or winding surfaces 86 of the joint members 71, 72, 73, 74, 75, 77, 78.

According to an embodiment, said at least one tendon 90, 190 describes a path around said first joint member 71, such as to at least partially wind itself over said joint sliding surface 40, 140 of said first joint member 71.

According to an embodiment, said at least one tendon 90, 190 describes a path around said distal second joint member 72, such as to at least partially wind itself over said joint sliding surface 80, 180 of said second joint member 72.

According to an embodiment, said medical instrument 60 comprises a plurality of tendons.

According to an embodiment, the projections of said tendon path T-T of said tendon 90 and of said tendon path T-T of said opposite tendon 190 on a plane orthogonal to said joint axis of movement of the closest rotational joint 171 overlap at least at a point of intersection 16, According to an embodiment, a said in-flight segment 9 of said tendon path T-T of said tendon 90 is substantially parallel to at least one said in-flight segment 9 of said opposite tendon 190.

According to an embodiment, the tendon paths T-T of each tendon 90 are substantially parallel to each other, on a projection plane parallel to the direction of said joint axis of joint movement of the closest rotational joint 171.

According to an embodiment, each said tendon termination feature 82 is positioned such as to support each tendon 90, 190 so as to keep its tendon path T-T substantially orthogonal to the joint axis of movement of the closest rotational joint 171, such as to allow said tendon 90 to slide on said at least one sliding surface 40, 80 following a tendon path T-T substantially parallel to the tendon path T-T of any other tendon.

According to an embodiment, each tendon termination feature 82 is positioned such as to support each tendon 90, 190 such that its tendon path T-T is stationary with respect to the joint member closest to it.

According to an embodiment, said tendon termination feature 82 is positioned such as to maintain its tendon path T-T of each tendon 90 substantially always in contact with said winding surface 86, when in operating conditions.

According to an embodiment, said tendon termination feature 82 is positioned such that the tendon path T-T of each tendon 90, 190 does not enter in contact with the tendon path T-T of any other tendon 90, 190, when in operating conditions.

According to an embodiment, said tendon termination feature 82 is positioned such that each tendon 90, when in operating conditions, slides on at least one sliding surface 40, 80, describing a curved section of the tendon path T-T substantially parallel to the curved section of the tendon path T-T described by any other tendon 90, 190 when it slides on the same sliding surface 40, 80.

According to an embodiment, said medical instrument 60 is a surgical instrument, suitable to be applied in at least one of the following fields: microsurgery, minimally invasive surgery and laparoscopic surgery.

According to an embodiment, said medical instrument 60 is suitable for being used for a biopsy. According to an embodiment, said medical instrument 60 is suitable to be used for an endoscopic procedure.

According to an embodiment, said tendon 90, 190 has a substantially circular cross section. According to an embodiment, the diameter of said tendon 90, 190 is variable in different portions of said tendon 90, 190. According to an embodiment, the mechanical properties of said tendon 90, 190 are variable in different portions of said tendon 90, 190. According to an embodiment, said tendon 90, 190 is obtained by joining portions of tendons with different characteristics. According to an embodiment, the composition of said tendon 90, 190 is variable in different portions of said tendon 90, 190.

According to an embodiment, said tendon path T-T in at least one portion of the tendon is substantially locally orthogonal to the generatrices of the sliding surface 40, 80, 140, 180 on which the tendon slides, in every operating condition, that is for any rotational angle of the rotational joints 171. These characteristics contribute to avoiding that said tendon path T-T of each of said tendons is ever deflected, that is to say that it never bends in a direction parallel to the axis of joint movement of the closest rotational joint 171.

According to an embodiment, said tendon path T-T is substantially locally orthogonal to the generatrices of the sliding surfaces 40, 80, 140, 180 on which it slides.

According to an embodiment, said jointed device 70 is primarily fabricated from metallic materials.

According to an embodiment, said joint members are suitable to be polished with the aim of further reducing the friction generated by the sliding of said at least one tendon, when said tendon slides over it.

According to an embodiment, a tendon drive system 50 for a medical instrument 60, 160, 260 comprises at least one pusher assembly 94.

Said medical instrument 60, 160, 260 comprises a frame 57 and at least one tendon 90, 190, exclusively suitable to work under tensile loads applied at its endpoints, in which a tendon direction T-T is defined, or a tendon path T-T, substantially coinciding with the direction of longitudinal development of said tendon 90, and in which said tendon 90 is fastened at its first endpoint 91, or proximal tendon endpoint 91, or first tendon termination 91, to said frame 57.

Said pusher assembly 94 is suitable to apply a force over at least one portion of said deflectable portion 93 of said tendon 90 along a pushing direction transversal to the tendon path T-T such as to deflect the tendon path T-T and induce an increased tensile load in said tendon 90.

When said pusher assembly pushes in said pushing direction, transversal to the tendon path T-T, it tends to lengthen locally, only locally, said tendon path. Such a localized path lengthening, which create a larger, local tendon loop is directly related to the amount of advancement of the pusher assembly. The creation of such a larger local tendon loop results at the opposite end of the tendon, in a proportional moving back of the distal endpoint of the tendon 92 which is fastened to the tendon termination feature 82 on the joint member and hence results in a movement of the joint member.

According to an embodiment, said pusher assembly 94 acts as a unilateral constraint for said tendon 90.

According to an embodiment, said pusher assembly 94 lengthens or shortens said tendon path T-T in at least one section of said tendon path T-T, which is substantially straight.

According to an embodiment, said pusher assembly 94 is suitable to retrieve a determined length of said tendon 90.

According to an embodiment, said pusher assembly 94 is suitable to release a determined length of said tendon 90.

According to an embodiment, said pusher assembly 94 is suitable to retreat on said tendon deflectable portion 93 of said tendon 90, in a direction transversal to the tendon path T-T such that the deflection of said tendon path T-T is decreased and the strain in said tendon 90 is decreased. In this way, a controlled movement of at least one portion of said jointed device 70 of said medical instrument 60 is allowed.

The terms "retreat" and "retrieve" mean that the pusher assembly, when pushing in said pushing direction, which is transversal to the tendon path T-T, locally and only locally, shortens the tendon path. Such a local shortening creates an increasingly smaller local loop, which is directly related to the amount of pulling back of the pusher assembly, and at the opposite end of the tendon, where it is fastened at its distal endpoint 92 to the joint member on which it acts, it allows a moving away of said distal endpoint, and hence enables the movement of said joint member.

According to an embodiment, said tendon 90 and opposite tendon 190 have lengths that result in said jointed device 70 of said medical instrument 60 being held in a reference position when said tendon 90 and said opposite tendon 90 are tensioned by the respective tensioning elements 99, 199.

According to an embodiment, said frame 57 comprises at least one shaft 65, in which a longitudinal shaft direction X-X is defined, said direction coinciding or being parallel to the axis of longitudinal development of said shaft 65.

According to an embodiment, said tendon 90 comprises at least one longitudinal tendon portion 19, in which the tendon path T-T is substantially parallel to the longitudinal direction of the shaft X-X, determining a movement of at least said longitudinal portion of tendon 19 with respect to said shaft 65, at least along the shaft direction X-X.

According to an embodiment, said pushing direction is parallel to the longitudinal direction of the shaft X-X.

According to an embodiment, said pushing direction is orthogonal to the longitudinal direction of the shaft X-X.

According to an embodiment, said tendon 90 is pretensioned. In this way, when said pusher assembly 90 stops exercising its pushing action on said tendon deflectable portion 93, said tendon 90 remains substantially under tension. The provision of a pretensioned tendon allows a simple calibration of said tendon drive system 50, making it possible to arbitrarily decide in which pose of the jointed device to position a zero pushing action pose.

According to an embodiment, said pusher assembly 94 always applies a minimum positive tension on tendon 90. In this way, as said pusher assembly contacts said tendon deflectable portion 93, said tendon 90 remain substantially always under tension. Provisioning a pretensioned tendon allows for the efficient control of the tendon path within the medical instrument 60, under any operating conditions.

According to an embodiment, said tendon 90 also comprises a second tendon endpoint 92, or distal tendon endpoint 92, suitable to pull a mobile element, which can be connected to said second distal tendon endpoint 92.

According to an embodiment, following said tendon along its tendon path T-T one first encounters said first tendon endpoint 91, then said at least tendon deflectable portion 93, and then said second tendon endpoint 92.

According to an embodiment, said mobile element is at least one portion of said medical instrument 60, 160, 260, which is mobile with respect to said frame 57.

According to an embodiment, when said tendon deflectable portion 93 is deflected by said pusher assembly 94, said tendon 90 determines the movement of at least one portion of said jointed device 70 with respect to said frame 57.

According to an embodiment, said pusher assembly 94 comprises at least one pushing element 95, mobile with respect to said frame 57 and suitable to push a plunger 96, such that said plunger 96 pushes on at least one tendon deflectable portion 93 of said tendon 90.

According to an embodiment, at least one body is placed between said pushing element 95 and said plunger 96. According to an embodiment, said pushing element 95 is in contact with said plunger. In other words, said at least one pushing element 95 is suitable to push directly or indirectly on said plunger 96.

According to an embodiment, said pushing element 95 is mobile with respect to said plunger 96 within a contacting position, in which said pushing element 95 is suitable to exercise a pushing action on said plunger 96, and a non-contacting position, in which said pushing element 95 is disconnected from said plunger 96, and it is not suitable to exercise any pushing action on said plunger 96. According to an embodiment, in said contacting position said pushing element 95 is not necessarily in contact with said plunger 96. In other words, according to an embodiment, said pushing element 95 exercises a pushing action via at least one intermediate body placed between said pushing element 95 and said plunger 96.

According to an embodiment, said pusher assembly 94 also comprises at least one sterile barrier 87, suitable to substantially impede mutual bacterial contamination of the two environments it separates.

According to an embodiment, said sterile barrier 87 is placed between said pushing element 95 and said plunger 96.

According to an embodiment, said sterile barrier is of a form and material suitable to transmit the push of said pushing element 95 to said plunger 96.

According to an embodiment, said pushing element 95 is mobile with respect to said frame 57 along a substantially linear trajectory.

According to an embodiment, said pushing element 95 is a piston.

According to an embodiment, said drive system 50 comprises at least two tendon guiding elements 97, or guiding pulleys, positioned along said tendon direction T-T such that when said pusher assembly determines a deflection of said tendon path T-T, said at least said two tendon guiding elements 97 cooperate to confine the deflection of said tendon path T-T to the tendon path section between said two guiding elements 97.

According to an embodiment, said plunger 96 comprises at least one plunger idle pulley 98, suitable to push on said tendon deflectable portion 93, and in which said plunger idle pulley 98 is suitable to freely turn around its axis, and in this way to reduce the sliding friction over said tendon deflectable portion 93 at least when pushed by said plunger 96.

According to an embodiment, said plunger idle pulley 98 is a ball bearing.

According to an embodiment, said second tendon endpoint 92 is a boss or a loop or a knot.

According to an embodiment, said tendon 90 is suitable to be pretensioned.

According to an embodiment, said tendon drive system 50 comprises at least one pretensioning element 99, suitable for maintaining said tendon 90 pretensioned.

According to an embodiment, said pretensioning element 99 is a spring, suitable to apply a force between the frame 57 and the plunger 96, to impose a preload on said tendon 90 that is substantially proportional to the compression movement of said spring 99.

According to an embodiment, said pusher assembly 94 comprises an electric motor, suitable to move said pushing element 95.

According to an embodiment, said pusher assembly 94 comprises a lead screw and nut type actuator. According to an embodiment, said actuator comprises a ball screw.

According to an embodiment, said tendon 90 is at least partially made of a material that is softer than the materials of the surfaces over which it slides. In other words, said tendon 90 is at least partially made of material that is less hard than the surface over which it slides.

According to an embodiment, said tendon 90 is at least partially made of polymeric material. The provision of a tendon made at least partially of polymeric material allows a reduction in wear of the surfaces over which it slides, with respect to a tendon made of metal, for example.

According to one variant of an embodiment, said first tendon endpoint 91, is fastened to said plunger 96, instead than to said frame 57.

According to an embodiment, said tendon drive system 50 comprises at least one further tendon 190, or opposite tendon 190, opposed to said tendon 90 and fastened or constrained in its first endpoint 91, or proximal endpoint, to said frame 57, said tendon 190 extending along the tendon direction T-T, or tendon path T-T.

According to an embodiment, said tendon drive system 50 comprises at least one further pusher assembly 94, or opposite pusher assembly 194, opposed to said pusher assembly 94 and suitable to push on at least one portion of tendon deflectable portion 93 of said opposite tendon 190, along a transversal pushing direction of tendon T-T such as to deflect the tendon path T-T and to induce an increased tensile load in said opposite tendon 190 and said tendon 90. In other words, said tendon 90 and said opposite tendon are suitable to work opposed to each other like antagonistic muscles of the human body that cooperate to determine the adduction and abduction movements of a joint.

According to an embodiment, said opposite pusher assembly 194 pushes on said tendon deflectable portion 93 of said opposite tendon 190 along a pushing direction transversal to said tendon path T-T, deflecting said tendon path T-T, inducing tensile load in said opposite tendon 190, from its proximal portion 18 and inducing tensile load in said tendon 90, from its distal portion 19.

According to an embodiment, said tendon 90 and said tendon 190 are distally structurally connected by a junction between said tendon and said opposite tendon. According to an embodiment, said tendon and said opposite tendon are both distally structurally connected to a common junction element, such that the transmission of the force by said tendon to said opposite tendon is guaranteed.

According to an embodiment, said opposite tendon 190 comprises a second endpoint 92, or distal endpoint 92, suitable to pull a mobile element associable to said second tendon endpoint 92 of said opposite tendon 190.

According to an embodiment, said opposite tendon 190 comprises a second endpoint 92, or distal endpoint suitable to pull a common, single mobile element, associable to both said second tendon endpoint 92 of said tendon 90 and said second tendon endpoint 92 of said opposite tendon 190. According to an embodiment, said tendon 90 and said opposite tendon 190 have lengths such that said common, single mobile element is in a reference position when said tendon 90 and said opposite tendon 190 are pretensioned by their respective pretensioning elements.

According to an embodiment, said tendon 90 and said opposite tendon 190 are two portions of a single tendon 90.

According to an embodiment, said second tendon endpoint 92 of said tendon 90 and said second endpoint 92 of said opposite tendon 190 coincide and are suitable for pulling a common mobile element, which can be associated both to said second endpoint 92 of said tendon 90 and to said second tendon endpoint 92 of said opposite tendon 190.

According to an embodiment, said opposite tendon 190 comprises at least a longitudinal portion 19, in which the tendon path T-T is substantially parallel to the longitudinal direction of the shaft X-X, such as to move at least said longitudinal portion 19 of said opposite tendon 190 with respect to said shaft 65, at least along the longitudinal direction of the shaft X-X.

According to an embodiment, said tendon drive system 50 comprises at least a pair of tendons 90, 190 for each degree of freedom, in which said tendon pair comprises a tendon 90 and an opposite tendon 190.

According to an embodiment, said tendon 90 and said opposite tendon 190 are suitable to be pulled simultaneously, such that the force transmitted to the common mobile element by both said tendon 90 and said opposite tendon 190 is the sum of the force transmitted by said tendon 90 and said opposite tendon 190.

According to an embodiment, said tendon 90 and said opposite tendon 190 are suitable to be simultaneously pulled with substantially the same amount of force.

According to an embodiment, said tendon 90 and said opposite tendon 190 are suitable to be pulled with a force on one of them higher than on the other.

According to an embodiment, said tendon 90 and said opposite tendon 190 are suitable to be simultaneously pulled, retrieving substantially the same tendon length from their proximal portion.

According to an embodiment, said tendon 90 is suitable to be pulled, retrieving a first tendon length from its proximal section and simultaneously said opposite tendon 190 is suitable to be released by its proximal portion, releasing a second tendon length from the opposite tendon, substantially equal to said first tendon length.

According to an embodiment, said tendon drive system 50 comprises an opposite
pretensioning element 199, suitable for maintaining said opposite tendon 190 pretensioned.

According to an embodiment, said opposite pretensioning element 199 is a spring 99.

According to an embodiment, said pretensioning element 99 and said opposite pretensioning element 199 are suitable to cooperate to simultaneously maintain said tendon 90 and said opposite tendon 190 pretensioned, so that the pusher assembly 94 and said opposite pusher assembly 194 can work at the same time.

The provision that said pretensioning element 99 and said opposite pretensioning element 199 allows said tendon 90 and said opposite tendon 190 to be kept in their pretensioned state, with a pretension value suitable to counterbalance the weight of said common mobile element attached to them. In this way, the gravitational force has no role in the drive system.

According to an embodiment, said tendon 90 and said opposite tendon 190 are suitable to connect their second endpoints 92 to their respective tendon fastening points 82, or tendon termination features 82, to one of: said second joint member 72 and said terminal member 77, such as to move it in opposite directions. The cooperation between said characteristic and the provision of said pretensioning element 99 and said opposite pretensioning element 199 allows for all movements to be positively guided and controlled, avoiding any passive or free joint movements, such as from return springs.

According to an embodiment, said tendon drive system 50 comprises a plurality of tendons 90 and a plurality of opposite tendons 190.

According to an embodiment, said tendon drive system 50 comprises a plurality of pusher assemblies 94 and a plurality of opposite pusher assemblies 194.

According to an embodiment, said plurality of tendons 90 and said plurality of opposite tendons 190 are positioned on a portion of a drum 59, or drum 59, of said frame 57 such that the tendon path T-T of each tendon 90, 190 runs separate with respect to the path of all other tendons 90, 190.

According to an embodiment, said plurality of tendons 90 and said plurality of tendons 190 are positioned substantially radially, or as rays, on said drum 59. According to an embodiment, said plurality of tendons 90 and said plurality of opposite tendons 190 are configured one said drum 59 like a cylinder of a radial engine, and in which the paths of said tendon 90 and said opposite tendon 190 do not cross each other on said drum 59.

According to an embodiment, each tendon 90 of said plurality of tendons 90 is suitable to be engaged by its respective pusher assembly 94 independently of other tendons 90.

According to an embodiment, said tendon 90 of said plurality of tendons 90 is suitable to be engaged by its respective pusher assembly 94 independently of an associated opposite tendon 190.

According to an embodiment, a drive system assembly for a medical instrument 60, 160, 260 comprises:

at least one tendon drive system 50 according to one of any embodiments previously described, at least one medical instrument 60, 160, 260 comprising at least one jointed device 70, 170, 270 in which said jointed device 70, 170, 270 comprises at least one rotational joint.

According to an embodiment, said tendon 90, 190 is fastened or constrained at its second endpoint 92 to at least a portion of said jointed device 70, 170, 270 mobile with respect to said frame 57, such that said tendon 90, 190 is suitable to pull on at least a portion of said jointed device 70, 170, 270, moving it with respect to said frame 57.

According to an embodiment, said tendon 90 and said opposite tendon 190 are both fastened to a same portion of said jointed device 70, 170, 270, mobile with respect to said frame 57, in their respective second endpoints 92, such that said opposite tendon 190 is suitable to pull at least a portion of said jointed device 70, 170, 270, moving it with respect to said frame 57 by a movement which is opposite to the movement determined by said tendon 90.

According to an embodiment, said drive system assembly comprises a tendon pair 90, 190, and said tendon pair comprises a tendon 90 and an opposite tendon 190, for every degree of freedom of movement of said jointed device 70, 170, 270.

According to an embodiment, when said tendon 90 and said opposite tendon 190 are pulled simultaneously and with substantially the same amount of force, the movement of at least a portion of said jointed device 70, 170, 270 of said medical instrument 60, 160, 260 is impeded.

According to an embodiment, when said tendon 90 and said opposite tendon 190 are simultaneously pulled with different amounts of force, where one amount of force is greater than the other, a controlled movement of at least a portion of said jointed device 70, 170, 270 of said medical instrument 60, 160, 260 results.

According to an embodiment, said medical instrument 60, 160, 260 is at least one of: a surgical instrument, a microsurgical instrument, an instrument for laparoscopic surgery, an endoscopic instrument, an instrument for biopsies.

According to an embodiment, a tendon 90, 190 for a medical instrument 60, said medical instrument 60 comprising at least one jointed device 70 and one frame 57, is suitable to move at least a portion of said jointed device 70 with respect to said frame 57.

Said jointed device 70 has at least on degree of freedom of movement with respect to said frame 57.

Said tendon 90 is exclusively suitable for working under tensile load.

Said tendon 90 is fabricated in a material that is less hard than the material of said jointed device 70.

The provision of this characteristic allows the fabrication of a medical instrument 60 comprising a jointed device 70 with greater resistance to wear, caused by the sliding of tendon 90 over at least a portion of said jointed device 70. Furthermore, this characteristic avoids any wear and loss of material of the surface of the jointed device 70 over which the tendon slides. In other words, the provision of this characteristic avoids said jointed device 70 from becoming scratched due to the effects of the tendon 90 sliding over it, when in operating conditions.

According to an embodiment, said tendon 90 slides over at least one portion of said jointed device 70, when in operating conditions.

According to an embodiment, said tendon 90 is made of a construction that is not suitable for transmitting pushing.

According to an embodiment, said tendon 90 is fabricated of a softer material than the material of said jointed device 70.

According to an embodiment, said tendon 90 is fabricated in a polymeric material. The provision of a tendon that is at least partially fabricated in a polymeric material allows the wear of the surface over which it slides to be reduced, with respect to a tendon made of metal for example, and helps to preserve the geometric tolerances established during the design phase and subsequently prolongs the life of said tendon 90, 190 as well as the life of said medical instrument 60, 160, 260.

According to an embodiment, said tendon 90, 190 is made of polyethylene. According to an embodiment, said tendon 90, 190 is made of high molecular weight polyethylene, or UHMWPE. According to an embodiment, said tendon 90, 190 is made of Kevlar. According to an embodiment, said tendon 90, 190 is made of Vectran. According to an embodiment, said tendon 90, 190 is made of Zylon, or PBO. According to an embodiment, said tendon 90, 190 is made of a combination of the above materials.

According to an embodiment, said tendon 90, 190 is made of polymer fibers.

According to an embodiment, said jointed device 70 is made of a metallic material.

According to an embodiment, said jointed device 70 is made of at least one of: INOX steel or stainless steel; super-fast steel; widia; hardened steel; tempered steel; titanium.

According to an embodiment, said jointed device 70 is made of a ceramic conductive material.

According to an embodiment, said tendon 90 comprises at least one tendon endpoint 91, suitable to be glued to said frame 57.

According to an embodiment, said tendon 90 is unraveled into strands around its first tendon endpoint 91 such as to maximize the glued surface.

According to an embodiment, said tendon 90 comprises at least a second tendon endpoint 92, suitable to connect to at least a portion of said jointed device 70.

According to an embodiment, said second endpoint 92 is a boss. According to an embodiment, said second tendon endpoint is a loop. According to an embodiment, said second tendon endpoint 92 is a knot.

According to an embodiment, said second tendon endpoint 92 is glued to at least one portion of said jointed device 70.

According to an embodiment, said first tendon endpoint 91 is terminated by wrapping said tendon around a portion of said medical instrument 60 multiple times. According to an embodiment, said second endpoint 92 is terminated by wrapping said tendon around a portion of said medical instrument 60 multiple times. According to an embodiment said tendon is wrapped around with a curvature radius that is substantially equal to its diameter.

According to an embodiment, said tendon 90, 190 has a diameter between 0.05 mm and 0.3 mm.

According to an embodiment, said tendon 90, 190 has an elastic module between 50 GPa and 100 GPa.

According to an embodiment, said tendon 90, 190 is fabricated such as to have a curvature radius inferior or substantially equal to one millimeter.

According to an embodiment, said tendon 90 is exclusively suitable to work under tensile load applied at the endpoints, avoiding said tendon to be pinched, to be laterally guided in a channel or to comprise a sheath.

According to an embodiment, said tendon 90, 190 is suitable to be pre-lengthened with a load cycle comprising at least two loads of an entity equal to at least half of the tensile breaking strength of said tendon 90, 190.

According to an embodiment, said tendon 90 has a transverse dimension, that is a dimension that is substantially orthogonal with respect to said tendon path T-T, variable in different tendon portions.

According to an embodiment, said tendon 90, 190 has a substantially circular cross section.

According to an embodiment, the diameter of said tendon 90 is variable in different portions of said tendon 90.

According to an embodiment, said tendon 90 is thinner at said second tendon endpoint 92. According to an embodiment, said tendon 90 is thicker in said longitudinal portion 19. This way, the tendon 90, 190 is suitable to be more flexible close to or at the tendon fastening point 82, as well as being stiffer close to or on the inside of said shaft 65.

According to an embodiment, the mechanical properties of said tendon 90 are variable in different portions of said tendon 90.

According to an embodiment, said tendon 90, 190 is obtained by joining or juxtaposing tendon portions with different characteristics.

According to an embodiment, the composition of said tendon 90, 190 is variable in different portions of said tendon 90, 190.

According to an embodiment, said tendon 90, 190 has a diameter between 0.1 mm and 0.3 mm.

According to an embodiment, said tendon 90 is suitable to cooperate with an opposite tendon 190 to move at least a portion of said jointed device 70, 170, 270.

According to an embodiment, when said tendon 90 and said opposite tendon 190 are suitable to be simultaneously pulled with one force being larger than the other, a controlled movement of at least a portion of said jointed device 70, 170, 270 or said medical instrument 60, 160, 260 results.

According to an embodiment, when said tendon 90 and said opposite tendon 190 are simultaneously pulled with the same force, the movement of at least a portion of said jointed device 70 of said medical instrument 60 is impeded.

According to an embodiment, a tendon pair 90, 190, in which every pair comprises a tendon 90 and an opposite tendon 190 is foreseen for every degree of freedom of movement for said jointed device 70.

In the following a driving method for a robotic assembly 100 is described.

A driving method of a surgical robotic assembly comprises the following phases:
- provide a robotic assembly 100 according to one of any of the embodiments previously described.
- employ at least a vision system associable to the robotic assembly 100 for the visualization of at least a portion of the patient 201.
- position said macro-positioning arm 30, such that the work volume 7, reached by at least a portion of said terminal portion 77 is within the field of view of said at least one vision system 103 associable to said robotic assembly 100;
- drive at least one micro-positioning device 41, 141, 241, 341;
- drive at least one jointed device 70, 170, 270 of a medical instrument 60, 160, 260, 360.

According to one possible operating mode, a driving method of a surgical robotic assembly comprises at least one of the following further phases, listed in a preferred, but not necessary order:
- release said macro-positioning arm 30 so as to be able to drag it.
- position said macro-positioning arm 30, so that the work volume 7 reached by said at least one terminal portion 77 is within the vision field of said at least one vision system 103, associable to said robotic assembly 100;
- lock said macro-positioning arm 30;
- drive said at least one micro-positioning device 41, 141, 241 by means of said at least one control device 20;
- drive said at least one jointed device 70, 170, 270 of the medical instruments 60, 160, 260 by means of said control device 20.

A control method for a control device for microsurgery for a microsurgical robotic assembly is described below.

A control method for a control device for microsurgery for a microsurgical robotic assembly comprises the following phase, listed in a preferred but not necessary order.
- provide at least one microsurgical control device 20 according to one of any of the embodiments previously described;
- manipulate said control instrument 21;
- move at least on portion of said control instrument 21 with respect to said detection device 22.

According to one possible operating mode, one method comprises at least one of the following further phases:
- provide a microsurgical robotic assembly 100 according to one of the embodiments previously described;
- move said surgical micro-instrument 60, 160, 260 by means of said control instrument 21;
- move said micro-positioning device 41, 141, 241 by means of said control instrument 21;
- use a microscope 103 associable to said robotic assembly 100 to visualize at least one portion of a patient 201;
- activate a teleoperation condition, or mode, according to which a movement of the control instrument 21 in a first direction, with respect to a coordinate system associated to at least one of said detection device 22 and said microscope 103, corresponds to a movement of said surgical micro-instrument 60, 160, 260 in the same direction with respect to said coordinate system.

According to an embodiment, said portion of the patient 201 is comprised in said work volume 7.

According to one possible operating mode, a method comprises the following further phases:
provide a further control device 20 such as to comprise a first control device 120 and a second control device 220;
manipulate said first control device 120 with one first hand;
manipulate said second control device 220 with a second hand.

According to one possible operating mode, one method comprises the following further phases:
provide a further control instrument 21, such as to comprise a first control instrument 121 and a second control instrument 221;
manipulate said first control instrument 121 with one hand;
manipulate said second control instrument 221 with the other hand.

A method for the fabrication of said medical instrument 60, 160, 260 is described below.

According to one possible operating mode, a fabrication method for the medical instrument 60, 160, 260 comprises a phase of fabrication of a medical instrument 60, 160, 260 according to one of any embodiments previously described, by at least one additive manufacturing technique.

According to one possible operating mode, a fabrication method of a medical instrument 60, 160, 260 comprises a phase of fabrication a medical instrument by micro-injection molding.

In other words, a fabrication method for the medical instrument 60, 160, 260 comprises a phase of fabrication of a medical instrument by means of micromolding.

A driving method of a tendon 90, 190 for a medical instrument 60, 160, 260 is described below.

A driving method of a tendon 90 for a medical instrument 60, 160, 260 comprises the following phases, listed in a preferred, but not necessary order of execution:
A') provide a tendon drive system 50 according to one of any of the previously described embodiments;
B') push at least on a portion of said tendon 90, 190 such as to deflect its tendon path T-T;
C') generate a tensile load in said tendon 90, 190.

According to one possible operating mode, a method comprises the further phase of providing a drive system assembly according to one of any of the embodiments previously described.

According to one possible operating mode, one method comprises at least one of the following further phases:
D') pretension said tendon 90 before phase B;
E') drive said pusher assembly 94 before phase B and after phase D;
F') after phase C, move at least one portion of said jointed device 70, 170, 270 of said medical instrument 60, 160, 260;
G') after phase F'), drive said opposite pusher assembly 194;
H') after phase G'), move said at least one portion of said jointed device 70, 170, 170 of said medical instrument 60, 160, 260 of phase F') in an opposite direction.

According to one possible operating mode, one method comprises the further phases of:
I') simultaneously drive said pusher assembly 94 and said opposite pusher assembly 194.
J') pull said tendon 90 and said opposite tendon 190 with differing amount of forces, force on one being greater than on the other;
K') move at least one portion of said jointed device 70, 170, 270 of said medical instrument 60, 160, 260 by a controlled movement.

According to one possible operating mode, a method comprises the further phases of:
L') instead of phase J'), pull said tendon 90 and said tendon 190 with substantially the same amount of force;
M') instead of phase K'), impede the movement of at least a portion of said jointed device 70, 170, 270 of said medical instrument 60, 160, 260.

According to one possible operating mode, one method comprises the following phases instead of the phases I'), J'), K'):
N') drive simultaneously said pusher assembly 94 and said opposite pusher assembly 194;
O') simultaneously pull said tendon (90) to retrieve a first tendon length from its proximal portion and release said opposite tendon (190) by its proximal portion releasing a second length of the opposite tendon, substantially equal to the first tendon length,
P') move at least one portion of said jointed device 70, 170, 270 of said medical instrument (60, 160, 260) by a controlled movement in relationship to said tendon length and opposite tendon length.

According to one possible operating mode, one method comprises the further phases of:
drive said opposite tendon 190 by means of said opposite pusher assembly 194;
move at least a portion of said medical instrument 60, 160, 260 by means of said pusher assembly 94.

A method to replace a tendon 90, 190 for a medical instrument is described below.

According to one possible operating mode, a method for replacing a tendon 90, 190 comprises the following phases:
provide a further tendon 90, 190 according to any of the embodiments previously described;
A") detach said tendon 90, 190 from said medical instrument 60;
B") mount said further tendon 90, 190 on said medical instrument 60.

According to one possible operating mode, the tendon 90 is attached first at said second tendon endpoint 92 and then at said first tendon endpoint 91.

According to one operating mode, a method comprises the following further phases:
C") before the phase A"), lock said plunger (96), in a position suitable to eliminate any pretension on the associated tendon 90.

According to an embodiment, said plunger (96) is locked by the use of a pin inserted in the plunger locking hole 48.

According to one possible operating mode, one method comprises the following further phases:
D") between the phase A") and the phase B"), clean said medical instrument 60.

According to one possible operating mode, said phase D") comprises a further sub-phase, which entails the immersion of said medical instrument 60 in a bath of organic solvents.

According to one possible operating mode, said phase A") comprises a further sub-phase of dissolving said any remain of tendon 90.

According to one possible operating mode, said phase A") comprises a further sub-phase of introducing said medical instrument 60 in an autoclave or other sterilization system.

According to one possible operating mode, said phase A") comprises a further sub-phase of introducing said medical instrument 60 in an oven at a temperature between 25° C. and 150° C.

According to one possible operating mode, said phase A") comprises a sub-phase of immerging of said medical instrument 60 in a chemical organic solvent bath.

According to one possible operating mode, said phase B") comprises the following sub-phases, preferably, but not necessarily, in the following order:
lock said jointed device 70 in a reference position and/or lock said plunger 96 in its locked position;
connect said second endpoint 92 to said jointed device 70;
thread said further tendon 90, 190 inside said shaft 65,
connect said first tendon endpoint 91 to said frame 57.

According to one possible operating mode, one method comprises the following further phase:
E") after the phase B"), calibrate of said medical instrument 60, 160, 260 identifying a new zero position for the plungers.

A fabrication method of the jointed device 70, 170, 270 is described below.

According to an embodiment, one fabrication method of a jointed device 70, 170, 270 comprises at least the following phases, in the preferred order indicated below:
(A'") provide a machining fixture 112 on an EDM machine and arrange a plurality of workpieces 117 on said machining fixture 112.
(B'") cut the desired geometry on said workpieces 117 with cutting lines parallel to each other.

The provision of a single cutting step on said workpieces with cutting lines parallel to each other, allows the machining of surfaces that are parallel to each other on said workpieces, with an extreme precision of parallelism.

According to one possible operating mode, the machining method described above allows the machining of ruled surfaces characterized by parallel generatices on said workpieces 117.

According to one possible operating mode, one machining method as described above allows the cutting of workpieces of very small dimension, for example of millimetric or sub-millimetric dimensions.

According to an embodiment, said machining method is suitable to fabricate at least one jointed device 70 that comprises a plurality of joint members 71,72, 73,74, 75, 76, 77, 78.

According to one possible operating mode, said machining method is suitable to machine parallel cuts on said workpieces 117 such as to form joint members comprising surfaces parallel to each other.

According to one possible operating mode, said machining method is suitable for machining parallel cuts on said workpieces 117 such as to form joint members suitable to be assembled in a complementary fashion because they comprise surfaces that are parallel to each other.

According to one possible operating mode, said EDM machine is suitable to perform wire EDM and comprises a cutting wire 115.

According to an embodiment, said cutting wire 115, or EDM wire 115, or electrical discharge machine wire 115 is of a diameter between 30 microns and 100 microns, and is preferably of 50 microns.

The provision of a machining method as described above allows exclusively thermal energy to be transferred to the piece being machined 117, avoiding any mechanical energy to be transferred to the piece being machined 117, for example inducing flexion, as it is the case when carrying out cuts with a milling machine.

According to an embodiment, said machining method is suitable to fabricate at least one jointed device for applications in the medical-surgical sector.

According to an embodiment, said machining method is suitable to fabricate at least one jointed device, suitable for applications in precision mechanics, for example suitable for use in watchmaking. According to an embodiment, said machining method is suitable to fabricate at least one jointed device, suitable for applications in the jewelry and/or fashion jewelry sector.

According to an embodiment, said machining method is suitable for the fabrication of at least one jointed device, suitable for applications in the assembly of electromechanical products.

According to one possible operating mode, the phase (A'") comprises the following sub-phases:
mount a plurality of workpieces on said machining fixture 112 in their respective member seats 116.

According to one possible operating mode, a sub-phase is first carried out during said phase (A'"):
(A1'") provide a machining fixture 112 on an EDM machine;
and then the sub-phase:
(A2'") arrange a plurality of workpieces 117 on said machining fixture 112.

According to a possible operating mode, one method comprises the following further phase between the sub-phase (A1'") and the sub-phase (A2'"):
(C'") carry out a calibration.

According to one possible operating mode, one method comprises the following further phase between the phase (A'") and the phase (B'"):
(C'") carry out a calibration.

According to one possible operating mode, one method comprises the following further phases after the phase (B'").
(D'") rotate said machining fixture 112.
repeat said phase (B'").

According to one possible operating mode, said phase of rotating said machining fixture 112 comprises a further phase of using a rotary table to rotate said machining fixture 112, avoiding to dismount said machining fixture 112 from the cutting machine to carry out the following phases:
rotate said machining fixture 112;
carry out a second calibration, or cut calibration, exclusively on said reference rod 118,
repeat said phase (B'").

According to one possible operating mode, said phase (C'"), carry out a calibration, comprises the following sub-phases:
switch on the EDM machine;
provide a reference rod 118 with its axis parallel to said member seats 116 of the workpieces 117;
bring said cutting wire 115 in contact with a first portion 122 of said reference rod 118, or portion facing towards the side of wire approach 122;
measure, or register, the position of said wire; and/or measure, or register, the position of said cutting wire 115, when it is in contact with a first portion of a first workpiece to be machined, or the portion facing the side of wire approach; execute the previous phase for each workpiece 117;

and/or bring the cutting wire 115 in contact with a second rod portion 123 of said reference rod 118, or portion facing the side of wire departure 123, opposite with respect to said first rod portion 122;

measure, or register, the position of said cutting wire 115;

compute the position of the axis of said reference rod 118 as a midpoint between the position of said wire when in contact with said first rod portion and the position of said wire when in contact with said second rod portion.

and/or measure, or register, the position of said cutting wire 115 when in contact with a second portion of said first workpiece, or the portion facing the side of wire departure;

compute the position of said first workpiece as a midpoint between the position of said wire when in contact with said first portion of the workpiece and the position of said wire when in contact with said second portion of the workpiece;

and/or execute the previous phase for each workpiece 117;

and/or repeat the procedure for all cutting planes X-Y, Y-Z, X-Z.

According to an embodiment, said machining fixture 112 of a jointed device 70, 170, 270 is suitable to be mounted on a machine for EDM.

According to an embodiment, said machining fixture 112 is suitable to perform at least two cuts on different cutting planes on workpieces 117 by using a single cutting profile 110 per cutting plane.

According to one realization, said machining fixture 112 comprises a first pair of fixing surfaces 113, 114, which are rectified, opposite and substantially parallel to each other and substantially orthogonal to a first plane of cutting X-Y.

According to an embodiment, said machining fixture 112 comprises a second pair of fixing surfaces 134, 135, which are rectified, opposite and substantially parallel to each other and substantially orthogonal to a second plane of cutting Y-Z.

According to an embodiment, said first pair of fixing surfaces 113, 114 and said second pair of fixing surfaces 134, 135 are rectified.

According to an embodiment, each pair of locating surfaces comprises at least one base fixing surface 113, 135 and at least one fixture fixing surface 114, 134.

According to an embodiment, said plurality of member seat 116 are sequentially arranged such that a translating straight line, substantially orthogonal to said first cutting plane X-Y, or substantially orthogonal to said second cutting plane Y-Z, would intersect at most only one of said workpieces 117 at a time, when said workpieces are mounted in respective member seats 116.

According to an embodiment, said member seats 116 are substantially parallel to each other.

According to an embodiment, said machining fixture 112 also comprises a pair of locating surfaces, opposite and substantially parallel to each other and substantially orthogonal to a third cutting plane X-Z.

According to an embodiment, said third pair of locating surfaces comprises at least a guide hole 125, and the EDM wire 115 of said EDM machine is inserted in at least one said guide hole 125, to avoid the EDM wire coming into contact with at least one machining fixture 112, during the cut.

According to an embodiment, said machining fixture 112 also comprises:

a plurality of member seats 116, each suitable to receive at least one workpiece 117, said workpiece 117 being suitable to realize at least one portion of said jointed device 70, 170, 270.

According to an embodiment, said machining fixture 112 also comprises at least one reference rod 118, suitable to allow for the cut calibration.

According to an embodiment, said machining fixture 112 comprises at least one fixing element, or fastening element, suitable to firmly connect said at least one workpiece 117 in its respective member seat 116.

According to an embodiment, said at least one fastening element is conductive glue.

According to an embodiment, said at least one fastening element is a grub screw.

According to an embodiment, said grub screw is suitable to be mounted in a threaded hole supplied in said at least one fastening surface.

According to an embodiment, said fastening grub screw, is suitable to penetrate in said threaded hole of said fastening surface.

According to an embodiment, said machining fixture 112 comprises four member seats 116 and a reference rod 118.

According to an embodiment, each member seat 116 is substantially positioned at the same distance from its respective fastening surface.

According to an embodiment, said fastening surfaces are positioned in a stepwise manner, such as to form a stair shape in profile. In other words, said fastening surfaces are positioned in a stepwise manner, such as to form a stair shape in profile with respect to at least one cutting plane X-Y, Y-Z, X-Z.

According to an embodiment, said machining fixture 112 has a surface facing towards any cutting plane X-Y, Y-Z, X-Z inferior to 10000 square millimeters.

According to an embodiment, said machining fixture 112 has a surface facing towards any cutting plane X-Y, Y-Z, X-Z inferior to 5000 square millimeters.

According to an embodiment, a medical instrument 60, 160, 260, 360 includes:

at least a joint member 71, 72, 73, 74 of a jointed device 70, a frame 57 including a shaft 65 a tendon 90,190 suitable to move said joint member 71, 72, 73, 74 with respect to said frame 57 a plunger 96 mobile along a degree of freedom with respect to said frame 57, in contact with said tendon 90,190 and suitable to actuate said tendon 90,190 a pushing element 95 mobile along a linear trajectory and including an actuator a sterile barrier 87 suitable to substantially impede mutual bacteria contamination of the two environments it separates, placed between said pushing element 95 and said plunger 96, wherein said plunger 96 is free to move away from said sterile barrier 87 and/or pushing element 95 and said pushing element 95 pushes on said sterile barrier 87 bringing it in contact with said plunger 96 and thus moves said plunger 96.

According to an embodiment, said pushing element 95 pushes on a plunger 96 in a pushing direction directed towards the inside of said frame 57, to move said plunger 96 along its degree of freedom with respect to said frame 57.

According to an embodiment, said pushing element 95 exchanges with said plunger 96 a force that is always directed in said pushing direction. In other words, said pushing element 95 is not suitable to exchange with said plunger 96 a pulling force, in other words said pushing element 95 cannot pull said plunger 96.

According to an embodiment, said pushing element 95 includes a lead screw and nut type actuator.

According to an embodiment, said actuator includes a ball screw.

According to an embodiment, said pushing element 95 includes a piston.

According to an embodiment, said plunger 96 has two portions one first portion of plunger 145 suitable to be in contact with said pushing element 95 and one second portion of plunger 146 to suitable to be in contact with said tendon 90, 190.

According to an embodiment, said first portion of plunger 145 is exposed from the frame 57 to be pushed by said pushing element 95.

According to an embodiment, said first portion of plunger 145 extends outside of frame 57 to be accessible by said pushing element 95.

According to an embodiment, said first portion of plunger 145 is flush with said frame 57 to be accessible by said pushing element 95.

According to an embodiment, said first portion of plunger 145 includes a pushing surface 147 suitable to be engaged with said pushing element 95.

According to an embodiment, said pushing elements 95 has a reciprocal pushing surface 148

According to an embodiment, said pushing element 95 pushes said plunger 96 transmitting a linear force through said a reciprocal pushing surface 148.

According to an embodiment, said pushing element 95 includes at least one pushing element idle pulley not represented, suitable to push on said pushing surface 147.

According to an embodiment, said pushing element 95 pushes said plunger 96 transmitting a linear force through said one pushing element idle pulley.

According to an embodiment, said pushing surface 147 and reciprocal pushing surface 148 are flat.

According to an embodiment, said pushing surface 147 and reciprocal pushing surface 148 are curved surface that mate with each other.

According to an embodiment, said pushing surface 147 and reciprocal pushing surface 148 are sliding surfaces that slide with respect to each other as said pushing element 95 moves along a linear trajectory.

According to an embodiment, said second portion of plunger 96 in contact with said tendon 90,190.

According to an embodiment, said medical instrument 60, 160, 260, 360 includes at least one tensioning element 99, suitable for impose a preload on said tendon 90.

According to an embodiment, said tensioning element 99 is a spring.

According to an embodiment, said tensioning element 99 is suitable to apply a force between the frame 57 and the plunger 96, in the direction of moving said plunger 96 so as to impose a preload on said tendon 90.

According to an embodiment, said tensioning element 99 is suitable to apply a force between the frame 57 and the plunger 96, in the direction of moving said plunger 96 away from said pushing element 95.

According to an embodiment, said tensioning element 99 is suitable to apply a force between the frame 57 and the plunger 96, in the direction of moving said plunger 96 towards the inside of said frame 57.

According to an embodiment, said preload is substantially proportional to the compression movement of said spring 99.

According to an embodiment, said second portion of plunger 146 pushes on at least one tendon deflectable portion 93 of said tendon 90.

According to an embodiment, said tendon deflectable portion 93 of said tendon 90 extends from a first guiding pulley 197 and second guiding pulley 297.

According to an embodiment, said second portion of plunger 146 moves in a space provided between said a first guiding pulley 197 and said second guiding pulley 297.

According to an embodiment, said plunger 96 changes the length of tendon 90 path between said a first guiding pulley 197 and said second guiding pulley 297 of an amount linearly proportional to the plunger 96 motion along said degree of freedom of plunger 96 with respect to said frame 57.

According to an embodiment, said second portion of plunger 146 includes at least one plunger idle pulley 98, suitable to push on said tendon deflectable portion 93, According to an embodiment, said tendon 90 has a first tendon endpoint 91 fastened to said joint member 71, 72, 73, 74.

According to an embodiment, said tendon 90 has a second tendon endpoint 91 fastened to said frame 57.

According to an embodiment, said first tendon endpoint 91, is fastened to said second portion of plunger 146, instead than to said frame 57.

According to an embodiment, said frame 57 includes a upper frame portion 58 and a lower frame portion 59 the latter including a shaft 65.

According to an embodiment, said plunger 96 is mobile along a degree of freedom with respect to said frame 57.

According to an embodiment, said plunger 96 is jointed to said upper frame portion 58 with a linear joint.

According to an embodiment, said plunger 96 is jointed to said lower frame portion 58 with a rotational joint not represented.

According to an embodiment, said plunger 96 moves linearly along a degree of freedom with respect to said frame 57.

According to an embodiment, said plunger 96 is maintained in a proper alignment by means of linear bushings not represented inserted in the first frame section 58.

According to an embodiment, said plunger 96 is maintained in a proper alignment with upper frame 58 by means of respective shoulder surfaces 88.

According to an embodiment, said plungers 96 is a rocker that rotates around a pivot of said frame 57.

According to an embodiment, said sterile barrier 87 is of a form and material suitable to transmit the push of said pushing element 95 to said plunger 96.

According to an embodiment, said sterile barrier 87 is a flexible continuous layer of material.

According to an embodiment, said sterile barrier 87 lays in between said pushing element 95.

According to an embodiment, said sterile barrier 87 is trapped between said pushing surface 147 and said reciprocal pushing surface 148.

According to an embodiment, said medical instrument 60, 160, 260, 360 includes a plurality of tendons 90 and of pairs of plungers 96 and associated pushing element 95.

According to an embodiment, said sterile barrier 87 is a flexible continuous layer of material.

According to an embodiment, said sterile barrier 87 is trapped between each plunger 96 and associated pushing element 95.

According to an embodiment, said sterile barrier 87 is made of a streachable material that streaches as said plungers 96 move with respect to said frame 57 exerting forces that do not substantially impede the motion of said plungers 96.

According to an embodiment, said sterile barrier 87 is a drape.

According to an embodiment, said sterile barrier 87 is a loose fitting drape that streaches as said plungers 96 move with respect to said frame 57 exerting forces that do not substantially impede the motion of said plungers 96.

Due to the provision of a pushing element 95 of a medical instrument 60, 160, 260, 360 according to an embodiment, suitable to move a jointed device across a sterile barrier allows the production of a medical instrument, which is highly reliable and sterile.

Due to the provision of a plunger 96 of a medical instrument 60, 160, 260, 360 according to an embodiment, it is possible to employ a simple sterile barrier in a shape of a drape or continuous flexible sheet of material.

Due to the provision of a plunger 96 of a medical instrument 60, 160, 260, 360 according to an embodiment, it is possible to increase the precision of the commanded motion using pushing elements with high precision linear actuators.

Due to the provision of a plunger 96 of a medical instrument 60, 160, 260, 360 according to an embodiment, it is possible to protect the tendons 90 inside said frame 57 while allowing sterile barrier 87 to be external to said frame.

Due to the provision of a plunger 96 of a medical instrument 60, 160, 260, 360 according to an embodiment, it is possible to provide tensioning to said tendons 90,190 for any joint member 71 position of said jointed device 70.

Due to the provision of a plunger 96 of a medical instrument 60, 160, 260, 360 according to an embodiment, it is possible to avoid lost motion and backlash effects associated to changes of direction of motion of which are altogether avoided making use of a continued pushing action of said pushing element on said plunger.

Due to the provision of a sterile barrier 87 of a medical instrument 60, 160, 260, 360 according to an embodiment, it is possible to provide a sterile barrier that is not attached to pushing element and so it is easier to deploy for the surgical staff.

According to an embodiment, said pushing element 95 includes a sensor 150.

According to an embodiment, said pushing element 95 includes a sensor 150 suitable to detect contact between said pushing element 95 and said plunger 96 through said sterile barrier 87.

According to an embodiment, said pushing element 95 includes a force sensor 151 suitable to measure the pushing force exchanged between said pushing element 95 and plunger 96 through said sterile barrier 87.

According to an embodiment, said force sensor 151 is a mono-axial load sensor measuring a component of pushing force along the linear trajectory of motion of said pushing element 95.

According to an embodiment, said pushing element 95 includes a pressure sensor 152 suitable to measure the pressure exchanged between said pushing element 95 and plunger 96 through said sterile barrier 87.

According to an embodiment, said pressure sensor 152 is a thin film pressure sensor glued to said reciprocal pushing surface 148 of said pushing element 95.

According to an embodiment, said pushing element 95 includes a non contact proximity sensor 153 suitable to measure the distance between said reciprocal pushing surface 148 and pushing surface 147 through said sterile barrier 87.

Due to the provision of a pushing element 95 of a medical instrument 60, 160, 260, 360 according to an embodiment, suitable to move a jointed device across a sterile barrier allows the production of a medical instrument, which is highly reliable and sterile.

Due to the provision of a sensor 150 of a medical instrument 60, 160, 260, 360 according to an embodiment, it is possible to sense through a sterile barrier a sensed quantity related to the interaction between said jointed device 70 and patient 201 anatomy.

Due to the provision of a sensor 150 of a medical instrument 60, 160, 260, 360 according to an embodiment, it is possible to detect contact between said pushing element 95 and plunger 96 through a sterile barrier.

Due to the provision of a sensor 150 of a medical instrument 60, 160, 260, 360 according to an embodiment, it is possible to sense a pushing force through a sterile barrier related to tension of tendon 90,190.

Known microsurgical procedures are carried out manually by the surgeon 200, or micro-surgeon 200, by the use of manual instruments, such as forceps, scissors and needle holders used to manipulate very fragile tissues and ducts with an diameter of 1 mm or less. The microsurgical procedure step most commonly performed is anastomosis, in which two small, severed vessels are sutured back together to reestablish blood flow. This procedure is carried out by holding the two adjacent vessel stubs with specific clamps and by using small caliber needles to perform the suture. The micro-surgeon 200 must hence perform very small movements, trying to limit the natural tremor of the hand and to maintain a high level of both concentration and sensitivity in order to delicately manipulate the fragile tissues with which he/she interacts via the instruments. It is apparent that robotics can bring significant improvement to the performance of complex microsurgical procedures.

According to an embodiment, said robotic assembly 100 has the function of supporting the surgeon 200 in the execution of a microsurgical procedure by using jointed devices and robotic devices that guarantee extremely precise movements, that scale down the actual hand movement of the surgeon 200 eliminating any tremor while reproducing the kinematics of the human wrist on a small scale.

According to an embodiment, said surgical robotic assembly 100 comprises a support 104, an articulated macro-positioning arm 30, and a pair of micro-positioning devices 41, 141, 241. A medical instrument 60, 160, 260, which comprises a motor box 61 and a sterile jointed device 70, 170, 270 is attached to each micro-positioning device 41, 141, 241.

Two control devices 20, suitable for the robotic control of the two medical instruments 60, 160, 260 and of the micro-positioning devices 41, 141, 241, are connected to the support 104 by communication cables 109. All the electronic control circuit boards and the power sources of the robotic assembly 100 are integrated in the support 104, while a control panel 108, for switching on and off and the management of user messages from the robotic assembly 100 by an operator, is situated on its surface. A dedicated, external video-microscope entry allows the integration of any traditional external microscope 103 for microsurgery. A digital microscope 103 is integrated in the system to visualize the substantially overlapping work volume 7 of the two sterile jointed devices 70, 170, 270.

According to an embodiment, a possible configuration of the surgical robotic assembly 100 is specifically dedicated to performing microsurgical procedures at the limb extremities or on free flaps. This is composed of an operating table 102 on which the limb to be operated on, or the free flap, is placed and comprises the use of a pair of jointed devices 70, 170, 270 connected to micro-positioning devices 41, 141, 241 and remotely controlled in real time by the microsurgeon 200 by their respective control devices 20. Note that microscope 103 is not part of the surgical robotic assembly 100 but is an independent element, fundamental for the visualization of the work volume 7 during the performance of the procedure.

According to an embodiment, a possible configuration of the surgical robotic assembly 100, particularly suitable for breast reconstruction procedures, but also suitable for carrying out microsurgeries on all other body parts, is composed of: a support 104 which allows for the support of the surgical robotic assembly 100 and for its transfer into the operating room to a position adjacent to the mobile operating table 102 on which the patient 201 is lying, one passive, articulated macro-positioning arm 30 that extends from the support 104 and allows the active part of the surgical robotic assembly 100 to reach the anatomical site involved in the procedure. A pair of precision micro-positioning devices 41, 141, 241, or micro-positioning devices 41, 141, 241, each with four degrees of freedom, to which the respective medical instruments 60, 160, 260 are attached, and which are used by the surgeon 200 to perform the microsurgical procedure by handling both the tissue and the small suture needles, are placed at the end of the surgical robotic assembly 100. The whole procedure is carried out under vision guidance provided by an external, traditional surgical microscope 103.

According to an embodiment, the support 104 has both a structural and transport function for the surgical robotic assembly 100, while the macro-positioning arm 30 connected to it allows the simultaneous positioning of a pair of micro-positioning devices 41, 141, 241 and the medical instruments 60, 160, 260 in proximity to the anatomical district which will be operated on. The micro-positioning devices 41, 141, 241 and the medical instruments 60, 160, 260 are actively moved and controlled in real time by the control devices 20.

According to an embodiment, each control device 20 is equipped with a support clamp or bracket, which can be independently positioned, for example by connecting it to the operating table 102. Said control devices 20 are connected to the surgical robotic assembly 100 by a power cable 107, also suitable for the transmission of control data.

According to an embodiment, to simplify the transport of the surgical robotic assembly 100, a retractable handle 106 and a foot platform 105 are positioned on a posterior side. The cart 104 has a control panel 108 on a posterior surface for the management of the parameters of the surgical robotic assembly 100 by the user and for the display of messages or warnings of the machine itself. On/Off switches (power buttons) and an emergency stop button are present on the same side. A power cable 107 supplies electrical current to the entire system, while the video data acquired by the digital microscope are passed to the surgical robotic assembly 100 via a communication cable 109, such as to be able to integrate vision-derived information into the controls.

According to an embodiment, said surgical robotic assembly 100 comprises a foot platform 105, suitable to be used together or alternatively to a retractable handle 106 for the transport of the robotic assembly 100 during its positioning in the operating room, placed on the bottom of the posterior side of the cart.

Said foot platform 105 allows the foot of an operator responsible for the movement of said robotic assembly 100 to rest on it, such that the robotic assembly 100 can also be pushed from the base, eliminating the risk of its tipping over while it is moved.

According to an embodiment, the control device 20 has the function of controlling the robotic movement of the micro-positioning devices and of the medical instrument 60, 160, 260.

The control device 20 comprises a control instrument 21, whose position in space is detected in real time by a magnetic tracking sensor. The magnetic tracking sensor is made of a magnetic field generator and of wired markers containing micro-bobbins, such as for example, but not limited to, the product "NDI AURORA V3 tracking system" comprising a "Planar field generator" and sensor "Mini 6DOF" by the company "NDI—Northern Digital Inc., 103 Randall Drive Waterloo, Ontario, Canada N2V1C5". The control instrument 21 integrates all the markers necessary for the detection of the six spatial coordinates of the control instrument 21 with respect to a base structure 67 and comprises an additional degree of freedom of gripping located in its tip portion 68, whose angle of aperture is measured by a tip sensor 29. Said tip sensor 29 is a position sensor or a proximity sensor. A connection tendon 23 connects the control instrument 21 to a base structure 67 that contains a magnetic field generator, suitable both for powering and data transmission between the control instrument 21 and said base structure 67, particularly, but not necessarily when it comprises a detection device 22. A power and communication tendon 24 connects the magnetic field generator to the external power source at the cart 104 of the robotic assembly, transferring the data relative to the position and orientation of the control instrument as well as the aperture angle of the forceps of the control instrument 21. A further marker for the detection of the six spatial coordinates of the cart with respect to the base structure 67 is present on the support 104 and connected by the power and communication tendon 24 to the base structure 67. Status signal lights 26 are integrated in the base structure 67 and communicate the activity of the control device to the user. A soft, dedicated, ergonomic operator support 27 is made to allow an ergonomic use of the control device 20, while the control instrument 21 reproduces the geometry of traditional micro-instruments such as the forceps and needle holder to make their handling more intuitive and familiar to the surgeon.

According to an embodiment, the macro-positioning arm 30 allows the anatomical districts involved in the surgical procedure to be reached by the active parts of the robotic assembly 100, such as, for example, the micro-positioning devices 41, 141, 241 and the medical instruments 60, 160, 260. Said macro-positioning arm 30 is composed of four members 31, 32, 33, 34 connected to each other in series by passive rotational joints each having vertical and parallel arm movement axes a-a, b-b, c-c. Inside each rotational joint, electromagnetic brakes allow the position of each single member to be locked in space. A dedicated brake release button 35, positioned below on the bottom side of the fourth arm member 34 to facilitate its grasping and activation, allows all joint brakes to be simultaneously released and thus to reposition each arm member in space as required by the user. The new position can then be frozen by undepressing the release button 35.

According to an embodiment, the first member 31 of the macro-positioning arm 30 is connected to a cart 104 by a rack and pinion mechanism that allows to manually control the movement of said macro-positioning arm 30 within a dedicated linear sliding guide 36 along a preferably vertical linear displacement axis, when a manual knob 37 is turned.

According to an embodiment, the fourth member 34 of the macro-positionting arm 30 has a rotational joint at its tip, which is manually activated by a dedicated rotational dial nut 43 that turns around a fourth axis of arm movement d-d, perpendicular to the third axis of arm movement c-c.

According to an embodiment, the macro-positioning arm 30 is connected to the support member 38 via the rotational joint, which is manually activated via the movement of said rotational dial nut 43. A pair of micro-positioning devices 41, 141, 241 is connected to the two extremities of said support member 38 that also carries a video camera 45 in its middle section, which can display enlarged images of the work volume 7 in which the microsurgery is carried out. The medical instruments 60, 160, 260 are rigidly attached to a distal portion of the micro-positioning devices 41, 141, 241.

According to an embodiment, the micro-positioning device 41, 141, 241 comprises three motorized slides 51, 52, 53, orthogonally connected to each other and able to each move independently along respective three axes of linear displacement f-f, g-g, h-h, and a motorized rotary joint 46.

According to an embodiment, said motorized slides 51, 52, 53 are motorized micro-slides. The medical instrument 60, 160, 260 is rigidly attached to the micro-positioning device 41, 141, 241 by a motorized rotary joint 46 that turns it around its longitudinal rotation axis r-r.

According to an embodiment, the medical instrument 60 has a motor box 61 that contains at least one tendon drive system 50 equipped to drive the jointed device 70 of said medical instrument 60 and its terminal device 77. According to an embodiment, the transmission mechanism integrated inside the mechanical transmission box 62, connected to the motor box 61, transmits the motion to the medical instrument 60 via the shaft 65 to the jointed device 70 and to the terminal device 77.

According to an embodiment the medical instrument 60 is made of a motor box 61 containing the actuators for driving the medical instrument 60, the associated electronic control boards and motor driver boards. The mechanical transmission box 62, which contains the mechanisms dedicated to transmit the motor motion via said shaft 65 along the longitudinal shaft direction X-X, to the jointed device and the terminal device 77, is connected to said motor box 61.

According to an embodiment, the motor box 61 contains six pushing elements 95 associated to three degrees of freedom of the medical instrument 60. In particular, said pushing elements are moved by at least one pusher assembly 94, which comprises electric micro-motors with a linear transmission system lead screws. Actuation pistons 95 come out of the wall of motor box 61 facing the transmission box 62 and actuate the transmission mechanism integrated into the mechanical transmission box 62.

According to an embodiment, the motor box 61 and the mechanical transmission box 62 are separated by a sterile barrier 87 and can be integrally connected with each other by connecting features, for example via a bayonet connection, as shown in FIG. 12.

According to an embodiment, the shaft 65 is hollow, fabricated in metal, extends itself along the longitudinal shaft direction X-X and inserts itself into the mechanical transmission box 62. The jointed device 70, 170, 270 with the terminal device 77 at the tip is inserted at the other shaft end or tip.

According to an embodiment, the six pushing elements 95, implemented as actuation pistons connected to motors, couple with the respective plungers 96 of the mechanical transmission box 62 thus connecting the motor box 61 with the mechanical transmission box 62, According to an embodiment, said pushing element 95 and said plungers 96 are separated by a sterile barrier 87.

According to an embodiment, the plungers 96 can move linearly along the piston movement axis and are maintained in a proper alignment by means of linear bushings not represented inserted in the first frame section 58, or upper frame 58, and by means of respective shoulder surfaces 88.

According to an embodiment, the actuation of the jointed device 70 is assigned to six tendons 90, or actuation cables 90, which are independent and run from a tendon fastening surface 84 in the mechanical transmission box 62, to the jointed device 70 of the medical instrument 60, via the mechanical transmission box 62, the tendon passage hole and the hollow shaft 65.

According to an embodiment, in its section running inside of the mechanical transmission box 62, each tendon 90 winds around each respective four guiding pulleys 97, mounted on said lower frame 59, such as to change its path direction until aligning with the instrument axis X-X. Such guiding pulleys 97 can be a fixed or idle pulleys and in a preferred configuration they are idle pulleys, with the exceptions of the first guiding pulley 197, positioned closest to the first tendon endpoint 91, which is a fixed guiding pulley 197.

According to an embodiment, a further plunger idle pulley 98, is positioned on each plunger 96 and moves integral with it along the linear piston pulley movement axis. Each actuation tendon 90 also partially winds around the respective plunger idle pulley 98, fastened to the respective plunger 96. Said plunger idle pulley 98 is located between said first guiding pulley 197 and a second guiding pulley 297.

According to an embodiment, the movement of the plunger 96 and hence of the plunger idle pulley 98 induced by the actuation piston 95, pushes the tendon 90 and hence varies its path length between said first guiding pulley 197 and said second guiding pulley 297. This change in length is transmitted by means of said transmission mechanism to the distal articulation of the medical instrument 60, 160, 260, resulting in its actuation.

According to an embodiment, a spring 99, suitable to work by compression, is inserted between the plunger idle pulley 98 and the upper frame 58 around the plunger 96.

According to an embodiment, said spring 99 generates a force directed along the plunger movement direction axis and establishes a variable preload on each plunger 96 sufficient to always keep the tendon 90 under a light tension and avoid its derailing from said guiding elements 97, 98, 197, 297 during changes in its tensile load.

According to an embodiment, a tendon guide element 89 maintains each tendon 90 in position and impedes its derailing, even in cases of anomalies such as a loss of tension in the tendons 90.

According to an embodiment, the jointed device 70 uses six low-friction, low minimum curvature radius and high stiffness polymeric tendons as movement transmission means for actuation of the three degrees of freedom of motion which the jointed device 70, 170, 270 is capable of. Each actuation cable, or tendon, 90, is glued with a low viscosity acrylic glue to tendon fastening surface 84 of the lower frame 59 and changes its direction by passing across four successive guide elements 97, 197, 297, integral to the lower frame 59 until it reaches the center of the transmission box 62 and enters through a central hole in the shaft 65 of the medical instrument 60, 160, 260 running in the direction of the instrument X-X, down to the jointed device 70, 170, 270.

As shown in FIG. 13, the first guiding pulley 197 of each actuation cables 90 is a fixed pulley 197 on which the tendon 90 winds. Successive guide elements are idle pulleys, around which tendon 90 is partly wound. Between said first guiding pulley 197 and said second guiding pulley 297 a space is provided allowing the linear motion of the plunger 96 actuated by the actuation piston 95.

According to an embodiment, at least one tendon 90 winds around at least four guiding pulleys 197, 297, 397, 497, thus defining a third guide element 397 and a fourth guide element 497. Between said third guide element 397 and said fourth guide element 497, a tendon guide element 89 keeps the tendon 90 in the correct position and avoids derailing of the tendon 90, even in cases such as an anomalous loss of tension.

According to an embodiment, the joint members that form the jointed device 70, 170, 270 and its terminal device 77, reproduce the kinematics of the human wrist adding a grasping degree of freedom of movement at the tip, for a total of three degrees of freedom of movement.

According to an embodiment, a first joint member 71 and a second joint member 72 are connected to each other by a rotational joint 171 around a first axis of rotation P-P, followed by a first portion of the terminal member 177 and a second portion of the terminal member 277, both connected to said second joint member 72, which freely rotate around a second axis of joint movement Y-Y, orthogonal to the first axis of joint movement P-P and providing a terminal device 77 at the tip.

According to an embodiment, the first member 71 locks on or is jointed in a concentric manner with the shaft 65 of the medical instrument 60 and is rigidly attached to it via fastening pins 76.

According to an embodiment, six actuation cables 90 run through the medical instrument shaft arranged respectively two planar groups of three symmetrically arranged with respect to a shaft section plane defined by the axis of the instrument X-X and by its first joint axis of joint P-P.

According to an embodiment, the tendon and opposite tendon 90,190 associated to second joint member 72, providing for its clockwise and anticlockwise rotation around said first joint axis of movement P-P, are arranged opposite to each other with respect to said section plane, slide over two opposite lateral sliding surfaces 40 of the first member 71, then both cross said section plane before said first axis of joint movement P-P, then they wind around at least one joint sliding surface 80 of the second member 72 and finally they attach to said second member 72.

According to an embodiment, the tendon and opposite tendon 90 associated to the first portion of the terminal member 177, like the two tendons 90 associated to the second portion of the terminal member 277, both run on the same side of said shaft section plane, they both slide on the same lateral sliding surface 40, 140 of first member 71, then they both cross said section plane before the first axis of joint movement P-P, then they both wind around at least one same sliding surface 80 of the second member 72 and continue their path to end up winding in opposite directions on the winding surface 86 of the terminal member 77. When only the first portions of the terminal member 177 or only the second portion of the terminal member 277 are actuated, the tendons 90 associated to said first portion of terminal member 177 and associated to said second portion of terminal member 277 slide along the sliding surface 80 of the second member 72.

According to an embodiment, the movement of the jointed device 70 is realized by polymeric actuation cables 90, or polymeric tendons 90. These tendons 90 run through the mechanical transmission box 62, run along the whole hollow shaft 65 and arrive at jointed device 70 and terminal device 77.

According to an embodiment, the transmission of motion to the joints of the jointed device 70 is a function of the path of the tendons 90 in the jointed device.

Exploiting the low friction, the very small curvature radius of the tendons 90, the tendons slide across the joint members that make up the jointed device and they wind around the various joint axes of movement P-P, Y-Y.

According to an embodiment, the members that make up the jointed device 70 are in fact rotationally connected to each other by a axis support feature of the rotational joint 171. Each member has joint sliding surfaces 80, or joint winding surfaces 86 for the tendons 90, both around the joint axis of movement P-P, Y-Y and along its body.

According to an embodiment, a further elbow joint member 75, positioned before a wrist joint member 78, suitable to reproduce the kinematics of the human wrist, can be included by provisioning an elbow joint member 75 characterized by having two distinct parallel axes of joint movement P-P, P-P. According to an embodiment, the first member 71 is coupled to said elbow member 75 having two distinct and parallel axes of joint movement P-P, P-P, one more proximal and one more distal, that are the first joint and second joint respectively. Said elbow member 75 has two lateral sliding surfaces 40, 140 arranged laterally opposite to each other with respect to a second section plane, defined as the plane that contains the first axis P-P and the second joint movement axis Y-Y.

According to an embodiment, there are eight actuation cables 90, 190. Said eight actuation cables, or tendons, run on the lateral sliding surfaces 40, 140 of the first member, arranged in one group of four opposite to another group of four with respect to said first section plane, and they cross said section plane before the first axis of joint movement P-P, hence they run on the first joint sliding surface 80 of the elbow member 75.

According to an embodiment, two actuation cables 90, 190, dedicated to the motion of rotational joint 171 of the elbow member, are terminated on said elbow member 75. The remaining six cables 90, 190 continue along the lateral sliding surfaces 40, 140 of the rotational joint 171 of the elbow, crossing a second section plane before said second joint axis. The following progression of the tendons around the second, third and fourth members 72, 73, 74, to the first portion of terminal member 177 and the second portion of terminal member 277 is analogous to what has been previously described in the presentation of the wrist configuration.

According to an embodiment, all members that form the jointed device 70 and the terminal device 77 are fabricated by a wire EDM performed on two orthogonal work planes X-Y, Y-Z.

According to an embodiment, fabricating the first member 71 starting from a cylindrical piece to be machined 117, said first member presents two circular surfaces that allow its concentric insertion into the shaft 65.

According to an embodiment, said circular surfaces present mating features on a lower portion, such as through-holes, that permit the rigid attachment of said first member of shaft 65 by means of fastening pins 76. Said first member 71 presents on a distal portion two features to support rotational joint 171, each characterized by a cylindrical seat centered around said first axis of joint movement P-P and a lateral shoulder surface.

According to an embodiment, all holes, being machined by wire EDM such as the pin holes 79, have extra machining grooves 49 resulting from the passage of the cutting wire 115.

According to an embodiment, having defined said first section plane containing the axis of the instrument X-X and the first joint movement axis P-P, the first member 71 presents two opposite tendon sliding surfaces 40, 140 each having rounded shapes that are symmetrically opposite i.e. mirrored with respect to said section plane.

According to an embodiment, being machined by wire EDM, each sliding surface 80, 180, 40, 140 is resulting from the sweeping motion of parallel straight generatrices that move directly along a cutting profile 110.

According to an embodiment, the actuation cables 90 slide in two groups of three, respectively along the two lateral sliding surfaces 40, 140, one opposite to the other on the first member 71 and they cross said section plane before the first axis of rotation to then continue onto second member 72.

According to an embodiment, said second member 72 has a joint sliding surface 80 proximally, arranged around said first axis of joint movement P-P having a cylindrical portion.

According to an embodiment, said joint sliding surface 80 is formed by parallel straight generatrices following the wire EDM cutting profile.

According to an embodiment, a pin holding feature 76 and a lateral shoulder surface characterize the joint of the first member 71 around the first axis of joint movement P-P. Two tendon termination features 82 are laterally derived from the second member 72 allowing the fastening of second tendon endpoint 92 of the second member by knot or gluing. Distally, two support features for the third and fourth rotational joint are each characterized by a pin hole 79 around the second axis of joint movement Y-Y and a lateral shoulder surface.

According to an embodiment, the second axis of joint movement Y-Y is orthogonal to the first axis of joint movement P-P. Being machined by wire EDM, the pin hole 79 has machining grooves 49, resulting from the cutting wire 115.

According to an embodiment, the third member 73 is characterized by a pin hole 79 located around the second axis of joint movement Y-Y. The third member 73 is mated to the second member 72 by a seat for a joint pin and an associated lateral shoulder surface. A winding surface 86 of the actuation cables 90, 190 allows the winding of the actuation cables 90, 190 around that winding surface 86 that is concentric to the second axis of joint movement Y-Y.

Laterally to the third member 73 a tendon termination feature 82 and tendon fastening points 82 are derived. The tendon termination feature 82 allows the passage of the tendons 90, and the tendon fastening point 82 holds the second tendon endpoint 92, 192 of the third member 73, defined by knots.

According to an embodiment, the first portion of the terminal member 177 and the second portion of the terminal member 277 are jointed to the second member 72, sharing the same second axis of joint movement Y-Y.

According to an embodiment, the first portion of the terminal member 177 mirrors the shape of the second portion of the terminal member 277.

According to an embodiment, the third member 73 can be individually mated to the second member 72 if the terminal device 77, present on the third member 73, is a medical instrument 60 of a surgical or microsurgical type, similar to, for example to a scalpel blade.

According to an embodiment, a terminal member 77, can be individually jointed to said second member 72, only if the terminal device 77 is itself a medical instrument 60 of a surgical or microsurgical type similar for example to a scalpel blade or to a fiber-optic tendon carrier for laser light treatments. In this case, the jointed device 70 will only comprise two degrees of freedom of movement, in particular of pitch and yaw, losing the degree of freedom for grasping.

According to an embodiment, the first portion of terminal member 177 and the second portion of terminal member 277 can mate with each defining different terminal devices 77, such as a micro device for cutting, a terminal micro device providing a straight grasp, a micro device providing angled grasping, a needle holder and other traditional microsurgical instruments as illustrated in FIGS. 25-27. The terminal devices reproduce the form, proportions and functionalities of traditional microsurgical instruments tips, in order to facilitate their recognition and use by the microsurgeon 200.

According to an embodiment fastening pins 76 are inserted in the pin holes 79 of the members of the jointed device 70. The fastening pins 76 are preferentially made of hard metal, rectified and polished to reduce sliding friction.

According to an embodiment the fastening pins 76 have interference in mating with the pin holes 79 located in correspondence to the axes of joint movement P-P, Y-Y, of rotational joint 171.

According to an embodiment, the fastening pins 76 have lee way, or clearance, in the pin holes 79 associated to the winding surfaces 86.

According to an embodiment, the connection by fastening pins 76 between the first member 71 and the second member 72 forms a rotational joint, suitable to rotate around the second axis of joint movement P-P, with an associated actuation angle substantially comprised between +90° and −90°.

According to an embodiment, the connection by a single fastening pin between the second joint member 72, the first portion of terminal member 177 and the second portion of terminal member 277 creates a rotational joint between said three members 72, 177, 277 with an associated actuation angular range substantially between +90° and −90°. Said joint defines two degrees of freedom, characterizing both the yaw and the grasp of the medical instrument 60.

According to an embodiment, the polymeric tendons 90, 190 can be terminated in several ways, provided that, as a result of strong fastening, they can be tensioned and such a tension is also transmitted to the joint member, or to the part to which they are connected, driving its motion.

According to an embodiment, the tendons 90 run through a tendon termination feature 82 and are locked by a knot formed by the tendon 90 itself, located at said tendon fastening point 82.

According to an embodiment, a second method for fastening the tendon 90, used for example for the actuation of the second member 72, provisions the passage of a loop of the tendon 90 around a tendon fastening point 82 and the application of tension to both the extremities of the tendon 90, such that the two sides of the tendon 90 act as a single tendon 90, halving the loads to which it is subject.

According to an embodiment, a third fastening method of the tendons 90 provisions the insertion of tendon portions in tendon fastening points 82, intended for this use, and the use of glues specific for the polymer of which the tendons 90 are made, such as those used for example for glueing the first endpoint 91 to the lower frame 59 of the mechanical transmission box 62 of the tendon drive system 50.

According to an embodiment, the jointed device 70 is characterized by three degrees of freedom of movement, and in particular by one degree of freedom of pitch between the first member 71 and the second member 72, one degree of freedom of yaw between the second member 72 and the third member 73, one degree of freedom of gripping, or grasping, between the first portion of terminal member 177 and the second portion of terminal member 277.

According to an embodiment, the second joint member 72, the first portion of the terminal member 177 and the second portion of the terminal member 277 can move around respectively said first axis of joint movement P-P and said second axis of joint movement Y-Y independently. The movement of the medical instrument 60 is carried out by the actuation cables 90, which run over the members jointed to each other by rotational joints.

According to an embodiment, a pair of tendons 90, 190 comprises a tendon 90 and an opposite tendon 190, which is suitable to work as a pair of agonistic and antagonistic tendons associated to a first portion of the terminal member 177 and a further pair of tendons 90, 190, comprising a tendon 90 and an opposite tendon 190, suitable to work as a pair of agonistic and antagonistic tendons associated to the second portion of the terminal member 277, and a further pair of tendons 90, 190, comprising a tendon 90 and an opposite tendon 190, suitable to act as a pair of agonistic and antagonistic tendons associated to the second joint member 72.

According to an embodiment, a pair of tendons, 90, 190, comprising a tendon 90 and an opposite tendon 190, suitable to work a a pair of agonistic and antagonistic tendons, transmit a rotational movement to the second portion of the terminal member 277, around said second axis of joint movement Y-Y, running over the lateral sliding surface 40 of the first joint member 71, crossing said section plane, running on the joint sliding surface 80 of the second joint member 72, and then splitting to wind them respectively in opposite directions around the winding surface 86 of the second portion of terminal member 277 and terminating with a knot. When one of the two tendons 90, 190 is tensioned or released, it slides on a sliding surface 40 of the first joint member 71 and over sliding surface 80 of the second joint member 72, while it winds itself or unwinds over the winding surface 86 of the fourth joint member like over a fixed pulley.

According to an embodiment, a further tendon pair 90, 190 consisting of a tendon 90 and an opposite tendon 190, actuates the first portion of terminal member 177 in a similar fashion to the way the second portion of terminal member 277 is actuated.

According to an embodiment, a yet further tendon pair 90, 190, consisting of a tendon 90 and an opposite tendon 190, suitable to work as a pair of agonistic and antagonistic tendons, move second joint member 72 around first axis of joint movement P-P, running over the lateral sliding surface 40, 140 of the first member 71, on one side with respect to said section plane of the medical instrument 60, intersecting said section plane, winding themselves in the opposite directions on the joint sliding surface 80 of the second joint member 72, and terminating at tendon fastening points 82.

In particular, each actuation tendon 90, 190 of the second joint member 72 is formed in a loop that passes around respective tendon fastening point 82 and comes back doubled up, passing over the winding surface 86, joint sliding surface 80 and lateral sliding surface 40 along a path analogous to that followed by the opposite tendon.

According to an embodiment, when moving the second joint member 72 around the first axis of joint movement P-P, in one rotation direction, both the end of the tendons 90, 190 are subject to tension. Furthermore, differently from the two tendon pairs 90, 190 that actuate the first portion of terminal member 177 and the second portion of terminal member 277 respectively, in the case of tendons 90 of the second joint member 72, the tendons 90, when moving, do not slide over the sliding surface of the second joint member 72, but wrap or unwrap around said joint sliding surface 80, as though it were a pulley.

According to an embodiment, six independent tendons 90 are used for the actuation of the threes degrees of freedom of movement of the jointed device 70, but eight cables intersect on said section plane between the lateral sliding surface 40 of the first joint member and the lateral sliding surface 80 of the second joint member 72, because both loop ends of the actuation cables 90, 190 of the second member 72 are tensioned during the movement in one direction around the first axis of joint movement P-P.

According to an embodiment, the sliding surfaces 80, 180 between the actuation cables 90 and members of the jointed device 70 are reduced to a minimum surface area, such as to reduce friction. The tendons 90, 190 are terminated at their second tendon end points 92 such a way that their tendon path T-T remains parallel to the instrument axis X-X as much as possible, avoiding transversal forces.

According to an embodiment, the intersection of the tendons 90 and their crossing of said section plane between the joint sliding surface 40 and the first axis of rotation P-P prevents the tendon 90 from leaving the joint sliding surface 80 during its movement and guarantees a constant length and angle of the tendons 90, 190.

A method for machining tridimensional, assemblable mechanical micro-components by EDM is described below. In particular it regards the fabrication of jointed devices 70 of a characteristic outer diameter inferior to 4 mm for application in micro-surgery. Furthermore, the main characteristics of a specific machining fixture 112, which is a fundamental element for the set up of a production process in an economically sustainable fashion and which is capable of guaranteeing the required precision, are described below.

According to an embodiment, the need to produce micro-parts with many mechanical details and a high level of precision requires the use of hard metals as a structural material and requires wire EDM as the machining process for the parts. As is known, EDM is a subtractive fabrication process in which material is removed by a conductive piece with a series of current discharges between the piece itself and an electrode kept at an electrical voltage difference, separated by a dielectric liquid such as water or oil, until the desired shape is obtained. In particular, during wire EDM machining, the workpiece 117 is held fixed and is immersed in a bath of dielectric liquid while a metal cutting wire 115, made of copper or brass for example, and of a diameter varying between 0.5 mm and 0.02 mm, continuously runs between two bobbins. The cutting wire 115 is sustained by an upper guide and a lower guide, which being driven by a computer numeric control system in the horizontal plane, carry out two-dimensional cutting profiles. The movement of the guides is very precise, and the overall machining resolution is close to 1 micron (µm), nevertheless, the planar cut substantially limits the fabrication of three-dimensional parts. Despite the fact that some advanced machines have an upper guide, which can move independently in the horizontal plane, the ability to produce complex 3D parts has not substantially increased.

The primary advantages of wire EDM comprise:
the possibility of machining hard metals,
absence of direct contact between the tool and the piece to be machined 117
delicate details can be machined without distortion,
a good superficial finish can be obtained,
complex shapes, otherwise difficult to produce with conventional cutting instruments can be produced, while maintaining very low tolerances.

The manual phases for the fastening each single, metallic workpiece to be machined 117 to the machine for each of the cutting planes and the following calibration of the machine itself, are very slow phases during the fabrication of the parts and are also the phases which result in the greatest geometric errors that hinder the perfect mating between micro-parts produced individually.

According to an embodiment, in order to substantially decrease the fabrication time and guarantee the precision required for the correct mating of the fabricated micro-parts, a machining fixture 112 is provided, which intended specifically for this use. It provides a mechanical support, which allows the simultaneous fastening and machining of all the workpieces 117, simplifying assembly of at least a portion of a jointed device 70 on one or more difference planes, with a single cutting profile 110 and a single calibration step.

According to one possible operating mode, the frontal plane of the machining fixture 112 has member holes 116, suitable to hold the workpieces 117 with very tight tolerance, that is to say at least H6h5.

According to one possible operating mode, the frontal plane of the machining fixture 112 has a "stepped" profile to allow threading short through holes on the stepped lateral planes.

According to one possible operating mode, grub screws M2 fasten the workpieces 117 to the machining fixture 112 and guarantee a perfect electrical conductivity with said machining fixture 112, which fundamental for a successful EDM process.

According to one possible operating mode, the grub screws disappear under the plane to which they are screwed, i.e. are headless, to avoid limiting securing the fixture along those planes, with a vise of an EDM machine.

According to one possible operating mode, an alternative to the grub screws and to the threaded holes associated to the grub screws, is the use of conductive glue, to fasten the workpieces 117 to the machining fixture 112 and guarantee a perfect electrical conductivity with said machining fixture 112.

According to one possible operating mode, the arrangement of the workpieces 117 on the machining fixture 112 is such that they not overlap in the work planes, for example in the X-Y and Y-Z planes, such that different and independent details or profiles can be cut for each plane on each workpiece 117, by providing a single and continuous cutting profile 110 for the wire.

According to one possible operating mode, the gap, or non-overlapping section, between two adjacent workpieces is minimized such as to keep the dimensions of the machining fixture 112 as compact as possible. In this way it is possible to minimize the distance between the upper and lower guides, improving the machining precision.

According to one possible operating mode, a metallic reference rod 118 is inserted in the machining fixture 112 and is used for calibration of the EDM machine once the machining fixture 112 and the workpieces 117 are mounted on the machine.

According to one possible operating mode, a first calibration is provisioned, which is carried out only once for a given machining fixture 112, loaded with all the workpieces 117 and a given EDM machine being used for the machining. Said first calibration is capable to identify and compensate all errors related to the EDM machine and to the geometric errors of the machining fixture 112, such as for example those related to the relative position between the reference rod 118 and the workpieces 117.

According to one possible operating mode, once the positions of the workpieces 117 are defined with respect to the reference rod 118 in the various cutting planes, the cutting profiles 110 are generated, taking into account of any differences of the actual positions with the nominal ones.

According to one possible operating mode, said first calibration will be repeated only if the EDM machine is changed or a new machining fixture 112 is being used.

According to one possible operating mode, each time the machining fixture 112, loaded with the workpieces 117, is secured to the vise of the EDM machine before a cut, a second calibration procedure is foreseen, or a cut calibration, performed only on the calibration rod 118.

This cut calibration process eliminates geometric offset and errors related to the manual fastening of the fixture and identifies the origin of the machine reference system with respect to the axis of the reference rod.

According to one possible operating mode, to allow the correct fastening of the machining fixture 112 to the vise of the EDM machine, said machining fixture 112 has at least a pair of fastening or fixing surfaces 113, 114, opposite and parallele to each other, and rectified, meant to be gripped by the jaws of the vise, and a flat posterior X-Z surface, rectified and orthogonal to the fixing surfaces 113, 114, meant to be flush with an reference surface of the machine, orthogonal to the vise's clamp.

According to one possible operating mode, by not using rotary table in the EDM machine, it is necessary that the machining fixture 112 have a pair of fixing surfaces 113, 114 that are flat, parallel and rectified, opposite to each other for each cut plane provisioned for the fabrication of the microcomponents.

According to one possible operating mode, other cutting planes can be produced by appropriately modifying the machining fixture 112.

According to one possible operating mode, to machine in a third orthogonal plane, it is necessary to provision openings 125 in the machining fixture that allow the cutting wire 115 to be inserted on the inside of the machining fixture and hence avoid the cutting of portions of the machining fixture 112, for example. Several independent cutting profiles must be used however without requiring further calibrations. Nevertheless, at the end of every cutting profile 110 in said plane, the cutting wire 115 must be cut and reinserted in the next opening 125.

According to one possible operating mode, the fabrication process used for the fabrication of parts of a jointed device 70, provisions the insertion of four workpieces 117 composed of metallic cylinders made of tool steel, into member holes 116 on the front side of said machining fixture 112 and then their fastening with grub screws of M2 size.

According to one possible operating mode, all three-dimensional micro-part that form the jointed device 70 for micro-medical applications, are machined from metallic workpieces 117, in particular steel cylinders of 3 millimeter outer diameter and 12 millimeter length, that are machined by wire EDM on two planes, X-Y and Y-Z.

According to one possible operating mode, the machining fixture 112 loaded with the workpieces 117 is secured on the vise of the EDM machine by using the fixing surfaces 113, 114 as reference planes for the fastening and then the calibration in the X-Y plane is performed using the axis of the reference rod 118, rigidly attached to the machining fixture 112, as a reference. The first cutting profile 110 is performed, machining all the workpieces 117 fastened to the machining fixture 112, in the X-Y plane.

According to one possible operating mode, the machining fixture 112 is then removed from the machine and remounted, rotated by 90° to machine along said second plane Y-Z of the machining fixture 112.

According to one possible operating mode, a second calibration for the second work plane Y-Z is performed and then the cut of the second cut profile 210 is carried out.

According to one possible operating mode, by equipping the EDM machine with a rotating or orientable table, it is possible to perform the cut calibration process just once and rotate the work plane as necessary between one cut profile and the next.

According to one possible operating mode, at the end of the second cut profile 210 the components produced are completely detached from the workpiece and can be collected in the EDM machine bath.

Due to the provision of a robotic assembly, according to one aspect of the invention, it is possible to control the positioning and motion of at least one jointed medical instrument within a work volume, in a reliable, precise and easily controllable manner.

Due to the provision of a robotic assembly, according to one aspect of the invention it is possible to control the positioning and simultaneous motion of at least two jointed medical instruments, each comprising one jointed device operative within a workspace, in a reliable, precise and easily controllable manner, potentially reaching every body part of the patient with the terminal portions of said medical instruments.

Due to the provision of a robotic assembly according to one aspect of the invention, comprising an image capturing system, but lacking an integrated microscope, it is possible to limit the cost as well as the physical volume of said assembly, resulting in a compact platform compatible with the installation of a pre-existing microscope, hence allowing retro-fitting operations.

Due to the provision of a robotic assembly according to one aspect of the invention, having as few moving parts as possible that require a large range of movement during the movement of the terminal portion of the medical instrument, it is possible to provide a microsurgical robotic assembly of low encumbrance, improving the comfort of the microsurgeon, who can, for example, tele-operate while being in the immediate vicinity of the operating table and hence can see and directly access the operating field, as well as improving the overall working conditions of the surgical team, by, for example, avoiding collisions with mobile parts of the robot while accessing the operating field, as well as simplifying the transport of the robotic assembly, or the flow of people or air around the robotic assembly. Equally, it becomes possible to use two or more robotic assemblies simultaneously on one patient.

Due to the provision of a control device according to one aspect of the invention, it is possible to simplify the teleoperation master interface and make it more intuitive and comfortable, without limiting its functionality. At the same time, the training time required by a surgeon, not necessarily specialized in microsurgical procedures, to achieve a sufficient level of mastery of the control device, is reduced.

Due to the provision of a microsurgical robotic assembly, according to one aspect of the invention, comprising a control instrument suitable to replicate the shape of a traditional surgical or microsurgical instrument, it is possible to provide a familiar master interface for teleoperation to the surgeon, without compromising the accuracy of the manipulation.

At the same time, according to one aspect of the invention, due to the provision of at least one sensor coupled to an electromagnetic 3 D tracking device, said control instrument is also suitable to replicate the functionality of traditional surgical or microsurgical instruments, while allowing a complete freedom of movement in the three dimensions of space and allowing easy repositioning of the control device, for example between the operating table and the microscope, still guaranteeing good performance of the robotic system in terms of response time.

At the same time, according to one aspect of the invention, due to the provision of a compact control device and at least one sensor, suitable for relating the robotic assembly and the detection device to a common reference system, it is possible to freely position said control device in a simple manner, for example said control device can be positioned next to the operating table, or on a support table close to the microscope, or in a position deemed ergonomic for the surgeon looking into the microscope.

Due to the provision of a control instrument according to an embodiment, which replicates the shape of a traditional microsurgical instrument having at least one joint at its tip, such as for example tweezers of forceps, equipped with at least one aperture sensor, it is possible to control the opening and closing, as well as grip movements of a jointed medical device in a familiar and precise manner.

The provision of a medical instrument comprising a jointed device moved by tendons according to an embodiment, reduces the complexity of its machining, for example by eliminating the provision of channels or sheaths, allowing extreme miniaturization of the medical instrument, without reducing its reliability during use or assembly.

Due to the provision of a jointed device according to an embodiment, comprising actuation cables, or tendons, made of non-metallic material, for example polymeric material, it is possible to reduce the curvature radius of said tendons, as well as the friction coefficient of said tendons and consequently miniaturize further the jointed device. Due to the provision of a jointed device according to an embodiment, comprising ruled surfaces with all parallel generatrices for the sliding of said tendons as well as tendon termination features arranged in a specific geometrical relationship to said surfaces, it is possible to do without tendon guide channels or sheaths, still guaranteeing parallelism of the tendons and hence allowing an extreme miniaturization of the jointed device.

Due to the provision of a fabrication method according to an embodiment, as well as a machining fixture, suitable to guarantee the simultaneous positioning of several workpieces in a manner that permits to their cutting lines to remain parallel to each other, it is possible to obtain a single cut path by a EDM cutting wire for each cutting plane, on a plurality of workpieces. In this way, it is possible to generate parallel surface on said pieces, with high tolerances, even in cases where very detailed, small shapes are machined.

Due to the provision of a fabrication method according to an embodiment, it is possible to produce micromechanical parts guaranteeing a high degree of precision as well as surfaces suitable for medical and/or surgical applications.

Due to the provision of a fabrication method, according to an embodiment, it is possible to produce a medical instrument more rapidly with respect to known solutions, and as a consequence, more cost-efficiently.

Due to the provision of a machining fixture, as well as a fabrication method, according to an embodiment, it is possible to obtain a fast and efficient process, even for repeated positioning of the workpieces within the machine.

Due to the provision of an improved machining fixture for EDM according to an embodiment, which accelerates the cutting process on a plurality of cut planes, it is possible to reduce the number and duration of the phases dedicated to calibrating the machine.

Due to the provision of a fabrication method for electro-erosion according to an embodiment, which permits the machining of micromechanical parts comprising cavities and ridges, that, even when leaving a groove between two prongs 81 of material, are suitable to form pin holding features without having to machine holes, it is possible to significantly reduce the machining time.

Due to the provision of a tendon drive system according to an embodiment, it is possible to guarantee the movement of said tendons exclusively by a pusher assembly, suitable to push the tendons and produce tensile load on at least a portion of said tendon. In this way the drive system avoids pulling on the tendons, for example by clinging to a portion of the tendon or by wrapping a portion of the tendon around a winch.

Due to the provision of a tendon drive system according to an embodiment, the number and complexity of the components of said drive are reduced and any backlash of the parts when they are not loaded can be avoided, making the system suitable for extreme miniaturization, without diminishing its reliability or its precision.

The provision of a tendon according to an embodiment, allows the reduction of an outer diameter dimension of said tendon and as a consequence, of the medical instrument, without reducing its performance in terms of durability or reliability.

Due to the provision of a tendon according to an embodiment, it is possible to guarantee improved performance in term of sliding friction of said tendon on at least a portion of said medical instrument, with respect to known solutions.

Due to the provision of a tendon, as well as a tendon replacement method, according to an embodiment, it is possible to increase the working lifespan of said instrument with respect to known solutions.

Due to the provision of a tendon according to an embodiment, produced of non-metallic material, for example polymeric material, it is possible to reduce the curvature radius of said tendon, as well as the friction coefficient of said tendon, and consequently increase the miniaturization of the medical instrument that comprises said tendon.

Due to the provision of a tendon according to an embodiment, it is possible to do without the provision of tendon guide canals or sheaths in the medical instrument, still guaranteeing the parallelism between a plurality of tendons and hence allowing an extreme miniaturization of the medical instrument.

Due to the provision of a tendon 90 comprising a second tendon endpoint 92 as described above, it is possible to obtain a jointed device 70 in which its members do not require tendon guides or channels to facilitate the tendon 90 routing, without said tendons 90 interfering with each other. In fact, the geometric location of said tendon endpoints 92 is chosen in a way that said tendons 90 run substantially parallel to each other and parallel to said sliding surface 40, 80.

Due to the provision of a sliding surface, for example lateral sliding surfaces 40 and joint sliding surfaces 80, as previously described, it is possible to for said tendons to slide over the jointed device with low friction.

Due to the cooperation between said sliding surfaces 40, 80 and the geometric location of said first tendon endpoints 91 and said second tendon endpoints 92 it is possible to guarantee that the friction forces between the tendon and the sliding surface, as well as the fastening reactions at the first and second tendon endpoints 91 and 92 are substantially parallel to each other and along a same axis.

Due to cooperation between said sliding surfaces 40, 80 and the geometric location of said first tendon endpoints 91 and said second tendon endpoints 92, it is possible to obtain an extreme miniaturization of said medical instrument 60. For example, in this way it is possible to do without pulleys and/or other tendon guides, which are not suitable to be miniaturized beyond a certain threshold. For example, according to an embodiment, the shaft 65 of said medical instrument can measure 3 millimeter in outer diameter.

Due to the provision of tendons 90 sustaining a curvature radius smaller than or substantially equal to 1 millimeters, it is possible to design a tendon path T-T, that at least partially wraps around said members 71, 72, 73, 74, 75, 77, 78, 177, 277 of said jointed device 70, such as to avoid the formation of loops, when for example at last a portion of said jointed device 70 moves with respect to an axis of movement P-P, Y-Y.

Due to the provision of said tendon drive system 50, as well as a tendon 90, 190 having said first tendon endpoint 91 and said second tendon endpoint 92, being a boss, and/or a knot, and/or glued as previously described, it is possible to mount as well as easily replace a tendon 90, 190 with high precision, prolonging the working lifespan of said medical instrument 60.

Furthermore, due to the provision of tendons made of polymeric material, the members of said jointed device 70 are not damaged during working conditions.

Due to the provision of a tendon drive system 50 comprising at least a pusher assembly 94 suitable to push, while resting on a tendon deflectable portion 93 of a tendon 90, it is possible to actuate said tendons without squeezing them or wrapping them around a capstan.

In this way it is possible to avoid damaging them when in working conditions, and hence increase the lifespan of said tendons, as well as of said medical instrument 60, diminishing maintenance costs.

Due to the provision of a tendon drive system 50 as previously described, it is possible to reduce to a minimum the backlash within the tendon drive system 50, always providing a defined preload.

Due to the provision of a substantially linear pusher assembly, it is possible to integrate micrometric actuation systems, such as slides and piezoelectric actuators, to control the tensile load of the tendons, as well as to release and pull exact lengths of tendon, allowing to move at least a portion of said medical instrument by a desired amount, for example around a movement axis.

The provision of a tendon drive system suitable for cooperating with a jointed device across a sterile barrier allows the production of a medical instrument, which is highly reliable and sterile.

Due to the provision of a fabrication method based on EDM as previously described, it is possible to fabricate an entire jointed device with only one placement step in a machine, decreasing the fabrication time and cost, without decreasing the reliability or precision of machining.

Due to the provision of a fabrication method according to an embodiment, it is possible to produce joint members of a jointed device having ruled surfaces with parallel generatrices, such as to allow a tendon sliding over them maintain a stationary path with respect to said joint member. This allows the friction between the tendon and the sliding surface of the joint member to be reduced to a minimum, facilitating the miniaturization of the jointed device.

Due to the provision of a fabrication method based on EDM as previously described, suitable to transfer only thermal stimulation to the workpieces, it is possible to obtain parts of submillimeter dimensions, allowing an extreme miniaturization of said medical instrument 60, still maintaining a satisfying cut precision due to the provision of cutting on a plurality of workpieces in a single passing.

Due to the provision of a tool, as well as a method of EDM according to an embodiment, suitable for performing, with a single wire passing, the cut of parts in a plurality of workpieces which will be assembled together after machining, it is possible to obtain matings with millimetric precision, particularly suitable for building rotational joints features such as prongs, pivot holes, profiles of joint members, allowing hence to reliably mount pieces by snap-fit, or with controlled backlash between the same parts.

Due to the provision of a robotic assembly 100, comprising at least one control instrument that replicates a traditional surgical instrument as well as a control device comprising an ergonomic support element for the operator, it is possible to improve the familiarity and ergonomics of the surgeon, improving the outcome of the surgical operation and patient comfort as a consequence.

Due to the provision of a robotic assembly according to one aspect of the invention, comprising a macro-positioning arm having a mechanical structure of arm members, as well as highly rigid joints, it is possible to avoid structural mechanical vibrations at the terminal portion of the instrument, and hence facilitate the surgeon's work.

Although some combinations of embodiments described above can be seen in the attached figures, an expert of the field will also be able to configure combinations not shown in the figures, without departing from the scope of the following claims.

To satisfy specific and temporary needs, a person skilled in the art can carry out a number of modifications, adaptations and substitutions of elements with other functionally equivalent elements, without departing from the scope of the following claims.

REFERENCE LIST 7 work volume, or common workspace volume
9 tendon
16 point of intersection
18 proximal tendon portion
19 distal tendon portion
20 control device
21 control instrument
22 detection device
23 connection cable
24 communication and power cable
25 operator support surface
26 status signal light
27 operator support element
28 position sensor
29 tip sensor
30 macro-positioning arm
31 first arm member
32 second arm member
33 third arm member
34 fourth arm member
35 release button, or brake release button
36 linear sliding guide
37 manual knob
38 support member
39 attachment feature
40 sliding surface
41 micro-positioning device
43 rotation dial nut
45 video camera
46 motorized rotary joint
47 base portion
48 plunger locking hole
49 machining groove
50 tendon drive system
51 first motorized slide, or first motorized micro-slide
52 second motorized slide, or second motorized micro-slide
53 third motorized slide, or third motorized micro-slide
54 first slide rail
55 second slide rail
56 third slide rail
57 frame
58 first frame portion, or upper frame
59 second frame portion, drum, or lower frame
60 medical instrument or micro-instrument or surgical micro-instrument
61 motor box
62 mechanical transmission box
63 sharp edge of lateral sliding surface
64 continuity surface of lateral gliding surface
65 shaft, or hollow shaft
67 control device base structure
68 tip portion of control device
69 forceps articulation of control device
70 jointed or articulated device
71 first member or first joint member, or first link
72 second member or second joint member, or second link
73 third member or third joint member, or third link
74 fourth member or fourth joint member, or fourth link
75 elbow member, or elbow link
76 fastening pin
77 terminal device, or terminal member, or terminal portion
78 wrist member or wrist joint member
79 pin hole
80 sliding surface or joint sliding surface
81 prong
82 tendon termination feature, or tendon fastening point.
83 surface
84 tendon fastening surface
86 winding surface, or ruled winding surface
87 sterile barrier
88 shoulder surface
89 tendon guide element
90 tendon, or actuation cable, or tendon of a first pair of tendons 91 first endpoint or first tendon endpoint, or proximal tendon endpoint, or first tendon termination
92 second endpoint or second tendon endpoint, or distal tendon endpoint, or second tendon termination
93 tendon deflectable portion or deflectable portion
94 pusher assembly or pushing means
95 pushing element, piston, actuation piston or linear actuation piston.
96 plunger or sliding shaft
97 guiding elements, or tendon guiding elements, or guiding pulleys
98 plunger idle pulley
99 tensioning element, or oretensioning element, or spring
100 robotic assembly, or robotic surgical assembly, or surgical robotic assembly, robotic assembly for micro-surgery or microsurgical robotic assembly
102 operating table
103 vision system, microscope, or surgical microscope
104 support or cart
105 foot platform
106 retractable handle
107 power cable
108 control panel
109 communication cable
110 cutting profile, or cutting line
111 display
112 machining fixture
113 first fixing surface of the first pair of fixin surfaces
114 second fixing surface of the first pair of fixing surfaces
115 cutting wire, or EDM wire, or electrical discharge machine wire
116 member holes or member seats
117 workpieces or pieces to be machined
118 reference rod
120 first control device
122 first rod portion
123 second rod portion
125 guide hole or opening
134 first fixing surface of the second pair of fixing surfaces
135 second fixing surface of the second pair of fixing surfaces
141 first micro-positioning device
145 first portion of plunger
146 second portion of plunger
147 pushing surface
148 reciprocal pushing surface
150 sensor
151 force sensor
152 pressure sensor
153 proximity sensor
160 first medical instrument
170 first jointed device
171 rotational joint
172 jointing portion
173 spherical joint
177 first portion of terminal member
190 opposite tendon, or opposite tendon of a first pair of tendons
191 tendon of a second pair of tendons
192 opposite tendon of a second pair of tendons
194 opposite pusher assembly or opposite pushing means
197 first guiding element, or first guiding pulleys
199 opposite tensioning element, opposite pretensioning element, or opposite spring
210 second cut profile
220 second control device
221 second control instrument
50 241 second micro-positioning device
260 second medical instrument
270 second jointed device
277 second portion of terminal member
297 second tendon guiding element, or second tendon guiding pulley
397 third tendon guiding element, or third tendon guiding pulley.
497 fourth tendon guiding element, or fourth tendon guiding pulley.
200 surgeon, or microsurgeon
201 patient
202 surgical needle
341 third micro-positioning device
360 third medical instrument
T-T tendon direction or tendon path
X-X longitudinal shaft direction, or instrument axis
P-P pitch axis, or first axis of joint movement
Y-Y yaw axis, or second axis of joint movement
a-a first axis of arm movement
b-b second axis of arm movement
c-c third axis of arm movement
d-d fourth axis of arm movement
e-e longitudinal axis of base portion of macropositioning arm
f-f first slide direction
g-g second slide direction
h-h third slide direction
r-r longitudinal axis of rotation
X-Y first cutting plane
Y-Z second cutting plane
X-Z third cutting plane
θ shaft angle

The invention claimed is:
1. A robotic surgical assembly comprising:
a support;
a macro-positioning arm, connected to said support and having a plurality of degrees of freedom, said macro-positioning arm comprising a support member;
at least two micro-positioning devices comprising a first micro-positioning device and a second micro-positioning device, each of said at least two micro-positioning devices having a plurality of motorized degrees of freedom, said at least two micro-positioning devices being connected in cascade to said support member of said macro-positioning arm;
wherein each of said micro-positioning device comprises:
a first motorized slide movable in a first slide rail along a first slide direction;
a second motorized slide movable in a second slide rail along a second slide direction;
a third motorized slide movable in a third slide rail along a third slide direction;
wherein said slides are orthogonally connected to each other;
at least two medical instruments comprising a first medical instrument and a second medical instrument, said first medical instrument being connected in cascade to said first micro-positioning device, said second medical instrument being connected in cascade to said second micro-positioning device;
wherein:
each of said at least two medical instruments comprises a jointed device, having a plurality of motorized degrees of freedom including a plurality of rotational joints and a shaft for distancing said jointed device from said micro-positioning devices by a predetermined distance in a shaft direction; and said first micro-positioning device provides at least three motorized degrees of freedom of translational motion to said shaft of said first medical instrument;

said second micro-positioning device provides at least three motorized degrees of freedom of translational motion to said shaft of said second medical instrument;

said robotic surgical assembly rigidly couples said shaft direction of the shaft of said first medical instrument and said shaft direction of the shaft of said second medical instrument; and the shaft angle between the shaft direction of the shaft of said first medical instrument and the shaft direction of the shaft of said second medical instrument is constant during any motion of any of said plurality of motorized degrees of freedom of said micro-positioning devices.

2. The robotic surgical assembly according to claim 1, wherein said at least two micro-positioning devices are rigidly attached to said support member so that said first medical instrument and said second medical instrument both reach a common workspace volume.

3. The robotic surgical assembly according to claim 1, wherein said first micro-positioning device rigidly blocks the shaft direction of said first medical instrument and said second micro-positioning device rigidly blocks the shaft direction of said first medical instrument.

4. The robotic surgical assembly according to claim 1, wherein said predetermined distance is equal to at least five times the longitudinal extension of said jointed device.

5. The robotic surgical assembly according to claim 1, wherein said medical instrument comprises a motor compartment suitable to accommodate at least one driving means of at least said jointed device of said medical instrument.

6. The robotic surgical assembly according to claim 1, comprising at least two control devices suitable to determine actuation of said micro-positioning devices and said medical instrument, according to a master-slave type communication.

7. The robotic surgical assembly according to claim 1, wherein said macro-positioning arm comprises:

a first arm member, connected to said support and movable with respect to said support along a linear sliding guide;

a second arm member, connected to said first arm member and movable with respect to said first arm member around a first arm movement axis.

8. The robotic surgical assembly according to claim 7, wherein said macro-positioning arm further comprises a third arm member, connected to said second arm member and movable with respect to said second arm member around a second arm movement axis; and/or wherein said macro-positioning arm further comprises a fourth arm member, connected to said third arm member and movable with respect to said third arm member around a third arm movement axis; and/or wherein said first arm movement axis, said second arm movement axis and said third arm movement axis, are substantially parallel to each other.

9. The robotic surgical assembly according to claim 8, wherein said macro-positioning arm comprises at least one locking system, suitable to prevent relative movement of at least two of said first arm member, said second arm member, said third arm member, and said fourth arm member.

10. The robotic surgical assembly according to claim 1, wherein said macro-positioning arm is a passive robot.

11. The robotic surgical assembly according to claim 1, wherein said macro-positioning arm includes motorized degrees of freedom.

12. The robotic surgical assembly according to claim 1, wherein said macro-positioning arm is an active anthropomorphic robot.

13. The robotic surgical assembly according to claim 1, wherein said first slide direction, said second slide directions and said third slide direction are orthogonal directions.

14. The robotic surgical assembly according to claim 1, wherein at least one of said micro-positioning devices comprises a motorized rotary joint, suitable to move the medical instrument around a longitudinal axis of rotation.

15. The robotic surgical assembly according to claim 14, wherein said longitudinal axis of rotation is substantially coincident with said direction of the shaft of the respective medical instrument.

16. The robotic surgical assembly according to claim 1, wherein the end portions of said first medical instrument and said second medical instrument reach the common workspace volume having a predetermined fixed size, and wherein said macro-positioning arm allows repositioning said common workspace volume in a desired position over patient anatomy.

17. The robotic surgical assembly according to claim 1, wherein said robotic surgical assembly is suitable to cooperate with a vision system, associated with said robotic surgical assembly.

18. The robotic surgical assembly according to claim 17, wherein said vision system is removably attached to said support member.

19. The robotic surgical assembly according to claim 17, wherein said vision system comprises a digital camera, and/or wherein said vision system comprises a digital microscope; and/or wherein said vision system comprises an endoscope; and/or wherein said endoscope is suitable to be used as a microscope; and/or wherein said vision system includes 3D digital microscope.

20. The robotic surgical assembly according to claim 17, wherein the common working volume is within a viewing field of said at least one vision system.

21. The robotic surgical assembly according to claim 17, wherein said vision system is integral with said support member.

22. The robotic surgical assembly according to claim 1, wherein said support member comprises a vision system seat suitable to house at least a vision system associated to said robotic surgical assembly.

23. The robotic surgical assembly according to claim 22, wherein the spatial orientation of said vision system seat of said support member is rigidly locked with respect to the spatial orientation of said at least two micro-positioning devices.

24. The robotic surgical assembly according to claim 1, wherein said macro-positioning arm comprises at least one unlocking button, the at least one unlocking button being switchable between a brake or locked position and a release or unlocked position.

25. The robotic surgical assembly according to claim 1, wherein said macro-positioning arm further comprises at least one rotation dial nut, said dial nut being movable around an arm movement axis and suitable to be manipulated for moving said support member around said arm movement axis.

\* \* \* \* \*